United States Patent
Nagase et al.

[11] Patent Number: 5,849,731
[45] Date of Patent: Dec. 15, 1998

[54] INDOLE DERIVATIVES AND MEDICAL APPLICATION THEREOF

[75] Inventors: Hiroshi Nagase; Koji Kawai, both of Kamakura; Takashi Endo, Chigasaki; Shinya Ueno, Kamakura; Masayuki Maeda, Kamakura; Satoshi Sakami, Kamakura, all of Japan

[73] Assignee: Toray Industries, Inc., Tokyo, Japan

[21] Appl. No.: 836,742

[22] PCT Filed: Sep. 26, 1996

[86] PCT No.: PCT/JP96/02791

§ 371 Date: May 16, 1997

§ 102(e) Date: May 16, 1997

[87] PCT Pub. No.: WO97/11948

PCT Pub. Date: Apr. 3, 1997

[30] Foreign Application Priority Data

Sep. 26, 1995 [JP] Japan ..................... 7-247472

[51] Int. Cl.[6] ............ C07D 491/22; A61K 31/475
[52] U.S. Cl. ............... 514/183; 514/214; 514/224.5; 514/229.5; 514/279; 540/476; 540/477; 540/577; 540/578; 540/579; 544/14; 544/56; 544/99; 546/27; 546/28; 546/29; 546/31; 546/34; 546/35
[58] Field of Search ................... 514/123, 214, 514/224.5, 229.5, 279; 540/476, 477, 577, 578, 579; 544/14, 56, 99; 546/27, 28, 29, 31, 34, 35

[56] References Cited

U.S. PATENT DOCUMENTS 4,816,586  3/1989  Portoghese ..................... 544/340
5,223,625  6/1993  Van Wijngaarden et al. ............ 546/70
5,225,417  7/1993  Dappen et al. ..................... 514/279
5,354,863  10/1994  Dappen et al. ..................... 546/35
5,411,965  5/1995  Reid et al. ..................... 514/279
5,457,208  10/1995  Portoghese et al. ..................... 546/35
5,631,263  5/1997  Portoghese et al. ..................... 514/279

FOREIGN PATENT DOCUMENTS

0636371A1  2/1995  European Pat. Off. .
95/31463A1  11/1995  WIPO .
95/31464A1  11/1995  WIPO .

*Primary Examiner*—Mukund J. Shah
*Assistant Examiner*—Deepak R. Rao
*Attorney, Agent, or Firm*—Birch, Stewart, Kolasch & Birch, LLP

[57] ABSTRACT

The present invention relates to indole derivatives represented by the following compound 1 and the pharmacologically acceptable acid addition salt thereof.

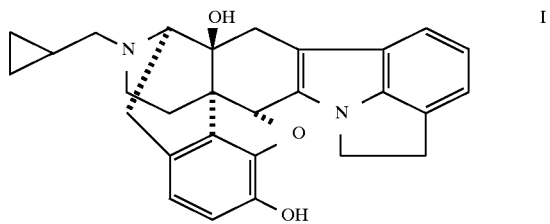

The compounds of the present invention were found to exhibit strong antitussive and analgesic actions as a result of pharmacological evaluation, and can be used in the pharmaceutical field as effective antitussives and analgesics.

13 Claims, No Drawings

INDOLE DERIVATIVES AND MEDICAL APPLICATION THEREOF

This application is a 371 of PCT/JP96/02791 filed Sep. 26, 1996.

TECHNICAL FIELD

The present invention relates to novel indole derivatives and medical applications thereof.

BACKGROUND ART

Nowadays, opioid receptors are classified into three types, μ, δ, and κ. Among these, δ opioid receptors have been researched only for a short time, and ligands selective to this receptor, especially alkaloid agonists have not yet been found and developed. Accordingly, δ opioid receptors have been lacking in research as compared with the other opioid receptors. Recently, among pharmacological actions relating to δ opioid receptors, antitussive action and analgesic action are attracting attentions.

Codeine, which is known as a typical antitussive capable of surely stopping coughing, acts on μ opioid receptors while essentially causing severe side effects such as drug dependence, respiratory depression, constipation, and suppression of CNS. There is, therefore, a demand for highly active antitussives which are free from μ opioidergic side effects as shown in codeine, and can be safely used. In recent years, although some κ opioid agonists were reported as showing antitussive activity, removal of aversion and psychotomimetic could not be achieved in many cases. Additionally, due to their agonistic properties on the opioid receptors, removal of suppression of CNS is still a problem to be solved. Lately, although some δ opioid antagonists were also reported as showing antitussive activity, they required improvement in antitussive activity for practical use.

Meanwhile, μ opioid agonists represented by morphine have been used as analgesics. The use of such agonists is, however, allowed only under strict management in view of the above-mentioned side effects. Further, in κ agonists, the above-mentioned side effects, i.e. aversion and psychotomimetic are also problems to be solved. Moreover, no alkaloid δ agonist has yet been developed, and its potential as an analgesic has not yet been clarified.

DISCLOSURE OF INVENTION

Accordingly, the object of the present invention is to provide δ opioid ligands (agonists and antagonists) which have a novel chemical structure, can be used as antitussives and analgesics, and are free from the above-described severe side effects such as drug dependence, respiratory depression, constipation, and suppression of CNS.

The Inventors earnestly conducted research to obtain the above-mentioned ideal δ ligands, and found that indole derivatives represented by the following general formula (I) and pharmacologically acceptable acid addition salts thereof exhibit strong antitussive or analgesic activities as δ ligands.

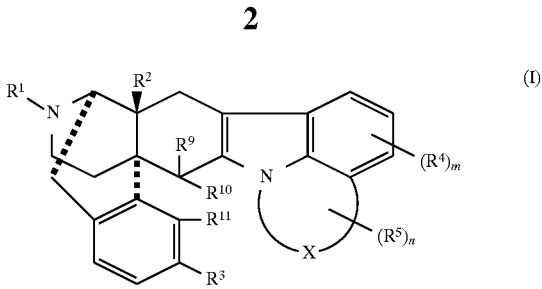

[In the above formula:

$R^1$ is hydrogen, an alkyl having 1 to 5 carbon atoms, a cycloalkylalkyl having 4 to 7 carbon atoms, a cycloalkenylalkyl having 5 to 7 carbon atoms, an aryl having 6 to 12 carbon atoms, an aralkyl having 7 to 13 carbon atoms (herein, "aralkyl" stands for "arylalkyl" and "arylalkenyl"), an alkenyl having 3 to 7 carbon atoms, a furan-2-yl-alkyl (herein, the alkyl has 1 to 5 carbon atoms), or a thiophene-2-yl-alkyl (herein, the alkyl has 1 to 5 carbon atoms);

$R^2$ is hydrogen, hydroxy, an alkoxy having 1 to 5 carbon atoms, or an alkanoyloxy having 1 to 5 carbon atoms;

$R^3$ is hydrogen, hydroxy, an alkoxy having 1 to 5 carbon atoms, an alkanoyloxy having 1 to 5 carbon atoms, or an aralkyloxy having 7 to 13 carbon atoms;

—X— is a crosslinkage comprising 2 to 5 carbon atoms (herein, at least one of the carbon atoms may be replaced with a nitrogen atom, an oxygen atom, or a sulfur atom);

m is an integer from 0 to 3;

n is an integer from 0 to 10;

each of m $R^4$ groups and n $R^5$ groups is individually fluoro, chloro, bromo, iodo, nitro, an alkyl having 1 to 5 carbon atoms, an alkoxy having 1 to 5 carbon atoms, trifluoromethyl, trifluoromethoxy, cyano, phenyl, a hydroxyalkyl having 1 to 3 carbon atoms, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH^2)_pN(R^7)COR^8$ (wherein p is an integer from 0 to 5; $R^6$ is an alkyl having 1 to 5 carbon atoms; each of $R^7$ and $R^8$ is individually hydrogen, an alkyl having 1 to 5 carbon atoms, or a cycloalkylalkyl having 4 to 7 carbon atoms; and among the above m $R^4$ groups and n $R^5$ groups, at least one pair of adjacent $R^4$ groups, adjacent $R^5$ groups, and one $R^4$ and one $R^5$ groups may be linked to form a benzene, pyridine, cyclopentane, cyclohexane, or cycloheptane condensed ring);

$R^9$ is hydrogen, an alkyl having 1 to 5 carbon atoms, an alkenyl having 1 to 5 carbon atoms, an aralkyl having 7 to 13 carbon atoms, a hydroxyalkyl having 1 to 3 carbon atoms, $(CH_2)_pOR^6$, or $(CH_2)_pCO_2R^6$ (herein, definitions of p and $R^6$ are the same as above);

$R^{10}$ and $R^{11}$ are linked to form an —O—, —S—, or —CH$_2$— group; or $R^{10}$ is hydrogen while $R^{11}$ is independently hydrogen, hydroxy, an alkoxy having 1 to 5 carbon atoms, or an alkanoyloxy having 1 to 5 carbon atoms; and (+) form, (−) form, and (±) form are included.]

BEST MODE FOR CARRYING OUT THE INVENTION

Preferred examples of $R^1$ include hydrogen, an alkyl having 1 to 5 carbon atoms, a cycloalkylmethyl having 4 to 7 carbon atoms, a cycloalkenylmethyl having 5 to 7 carbon atoms, phenyl, naphthyl, a phenylalkyl having 7 to 13 carbon atoms, a phenylalkenyl having 7 to 13 carbon atoms, an alkenyl having 3 to 7 carbon atoms, a furan-2-yl-(C1 to C5)alkyl, and a thiophene-2-yl-(C1 to C5)alkyl. Especially preferred are hydrogen, methyl, ethyl, propyl, butyl, cyclopropylmethyl, cyclobutylmethyl, cyclopentylmethyl, cyclohexylmethyl, cyclopentenylmethyl, cyclohexenylmehtyl, benzyl, phenethyl, cinnamyl, 3-butenyl, trans-2-butenyl, prenyl, allyl, furan-2-ylmethyl, furan-2-ylethyl, thiophene-2-ylmethyl, and thiophene-2-ylethyl.

Preferred examples of $R^2$ are hydrogen, hydroxy, acetoxy, propionoxy, methoxy, and ethoxy, while especially preferred are hydrogen, hydroxy, acetoxy, and methoxy.

Preferred examples of $R^3$ are hydrogen, hydroxy, acetoxy, propionoxy, methoxy, ethoxy, and benzyloxy, while especially preferred are hydrogen, hydroxy, acetoxy, methoxy, and benzyloxy.

As the linkage —X—, an alkylene having 2 to 5 carbon atoms is preferred wherein one carbon atom may be replaced with a nitrogen atom, an oxygen atom, or a sulfur atom. Especially preferred are an alkylene having 2 to 5 carbon atoms, —(CH$_2$)$_2$—O—, and —(CH$_2$)$_2$—S—.

Preferred examples of $R^4$ and $R^5$ include fluoro, chloro, bromo, iodo, nitro, an alkyl having 1 to 5 carbon atoms, an alkoxy having 1 to 5 carbon atoms, trifluoromethyl, trifluoromethoxy, cyano, phenyl, a hydroxyalkyl having 1 to 3 carbon atoms, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, and $(CH_2)_pN(R^7)COR^8$, wherein p is an integer from 0 to 5; $R^6$ is an alkyl having 1 to 5 carbon atoms; each of $R^7$ and $R^8$ is individually hydrogen, an alkyl having 1 to 5 carbon atoms, or a cycloalkylalkyl having 4 to 7 carbon atoms. Especially preferred are fluoro, chloro, bromo, iodo, nitro, methyl, methoxy, trifluoromethyl, trifluoromethoxy, cyano, phenyl, hydroxymethyl, hydroxyethyl, isothiocyanato, methylthio, methylsulfinyl, methylsulfonyl, methoxymethyl, ethoxymethyl, methoxyethyl, methoxycarbonyl, ethoxycarbonyl, methoxycarbonylmethyl, ethoxycarbonylmethyl, sulfamoyl, dimethylsulfamoyl, dimethylcarbamoyl, dimethylamino, dimethylaminomethyl, dimethylaminoethyl, and amino. As a matter of course, it is also preferred that both m and n are 0, namely, no substitution is made concerning $R^4$ and $R^5$. Additionally, at least one pair of adjacent $R^4$ groups, adjacent $R^5$ groups, and one $R^4$ and one $R^5$ groups may be linked to form a benzene, pyridine, cyclopentane, cyclohexane, or cycloheptane condensed ring, while a benzene condensed ring is especially preferred.

As the group $R^9$, preferred examples are hydrogen, an alkyl having 1 to 5 carbon atoms, allyl, and benzyl, while especially preferred are hydrogen and methyl.

As to the groups $R^{10}$ and $R^{11}$, preferably, these are linked to form an —O— group, or $R^{10}$ is hydrogen while $R^{11}$ is hydrogen, hydroxy or methoxy. Especially preferably, these are linked to form an —O— group.

Needless to say, the present invention is not limited to the above-described examples. Meanwhile, examples of pharmacologically acceptable acid addition salts of the above-described indole derivatives include inorganic acid salts such as hydrochloride, sulfate, nitrate, hydrobromide, hydroiodide, and phosphate; carboxylates such as acetate, lactate, citrate, oxalate, glutaric acid salts, malate, tartarate, fumarate, mandelate, maleate, benzoate, and phthalate; and sulfonates such as methanesulfonate, ethanesulfonate, benzenesulfonate, p-toluenesulfonate, and camphorsulfonate. In particular, hydrochloride, hydrobromide, phosphate, tartarate, methanesulfonate, and others are preferably used. Also, the present invention is not limited to these examples.

Among the compounds represented by general formula (I), the compound in which $R^1$ is cyclopropylmethyl, $R^2$ and $R^3$ are hydroxy, —X— is ethylene, m and n are 0, $R^9$ is hydrogen, $R^{10}$ and $R^{11}$ together are —O—, that is, the compound 1

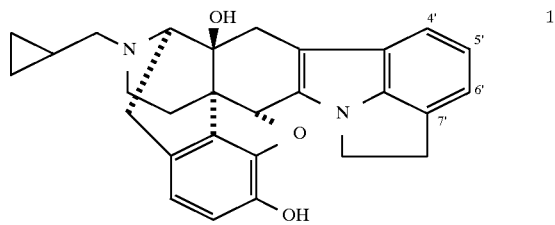

is named 17-cyclopropylmethyl-6,7-didehydro-4,5α-epoxy-3,14β-dihydroxy-1',7'-ethylene-6,7,2',3'-indolomorphinan. According to this nomenclature, specific examples of the compounds employed in the present invention include 17-allyl-6,7-didehydro-4,5α-epoxy-3,14β-dihydroxy-1',7'-ethylene-6,7,2',3'-indolomorphinan, 17-cyclopropylmethyl-6,7-didehydro-4,5α-epoxy-3-hydroxy-14β-methoxy-1',7'-ethylene-6,7,2',3'-indolomorphinan, 17-allyl-6,7-didehydro-4,5α-epoxy-3-hydroxy-14β-methoxy-1',7'-ethylene-6,7,2',3'-indolomorphinan, 17-cyclopropylmethyl-6,7-didehydro-4,5α-epoxy-3-methoxy-14β-hydroxy-1',7'-ethylene-6,7,2',3'-indolomorphinan, 17-allyl-6,7-didehydro-4,5α-epoxy-3-methoxy-14β-hydroxy-1',7'-ethylene-6,7,2',3'-indolomorphinan, 17-cyclopropylmethyl-6,7-didehydro-4,5α-epoxy-3,14β-dimethoxy-1',7'-ethylene-6,7,2',3'-indolomorphinan, 17-allyl-6,7-didehydro-4,5α-epoxy-3,14β-dimethoxy-1',7'-ethylene-6,7,2',3'-indolomorphinan, 17-cyclopropylmethyl-6,7-didehydro-4,5α-epoxy-3,14β-dihydroxy-1',7'-ethylene-4'-fluoro-6,7,2',3'-indolomorphinan, 17-allyl-6,7-didehydro-4,5α-epoxy-3,14β-dihydroxy-1',7'-ethylene-4'-fluoro-6,7,2',3'-indolomorphinan, 17-cyclopropylmethyl-6,7-didehydro-4,5α-epoxy-3-hydroxy-14β-methoxy-1',7'-ethylene-4'-fluoro-6,7,2',3'-indolomorphinan, 17-allyl-6,7-didehydro-4,5α-epoxy-3-hydroxy-14β-methoxy-1',7'-ethylene-4'-fluoro-6,7,2',3'-indolomorphinan, 17-cyclopropylmethyl-6,7-didehydro-4,5α-epoxy-3-methoxy-14β-hydroxy-1',7'-ethylene-4'-fluoro-6,7,2',3'-indolomorphinan, 17-allyl-6,7-didehydro-4,5α-epoxy-3-methoxy-14β-hydroxy-1',7'-ethylene-4'-fluoro-6,7,2',3'-indolomorphinan, 17-cyclopropylmethyl-6,7-didehydro-4,5α-epoxy-3,14β-dimethoxy-1',7'-ethylene-4'-fluoro-6,7,2',3'-indolomorphinan, 17-allyl-6,7-didehydro-4,5α-epoxy-3,14β-dimethoxy-1',7'-ethylene-4'-fluoro-6,7,2',3'-indolomorphinan, 17-cyclopropylmethyl-6,7-didehydro-4,5α-epoxy-3,14β-dihydroxy-1',7'-ethylene-5'-fluoro-6,7,2',3'-indolomorphinan, 17-allyl-6,7-didehydro-4,5α-epoxy-3,14β-dihydroxy-1',7'-ethylene-5'-fluoro-6,7,2',3'-indolomorphinan, 17-cyclopropylmethyl-6,7-didehydro-4,5α-epoxy-3-hydroxy- 14β-methoxy-1',7'-ethylene-5'-fluoro-6,7,2',3'-indolomorphinan, 17-allyl-6,7-didehydro-4,5α-epoxy-3-hydroxy-14β-methoxy-1',7'-ethylene-5'-fluoro-6,7,2',3'-indolomorphinan, 17-cyclopropylmethyl-6,7-didehydro-4,5α-epoxy-3-methoxy-14β-hydroxy-1',7'-ethylene-5'-fluoro-6,7,2',3'-indolomorphinan, 17-allyl-6,7-didehydro-4,5α-epoxy-3-methoxy-14β-hydroxy-1',7'-ethylene-5'-fluoro-6,7,2',3'-indolomorphinan, 17-cyclopropylmethyl-6,7-didehydro-4,5α-epoxy-3,14β-dimethoxy-1',7'-ethylene-5'-fluoro-6,7,2',3'- indolomorphinan, 17-allyl-6,7-didehydro-4,5α-epoxy-3,14β-dimethoxy-1',7'-ethylene-5'-fluoro-6,7,2',3'-indolomorphinan, 17-cyclopropylmethyl-6,7-didehydro-4,5α-epoxy-3,14β-dihydroxy-1',7'-ethylene-6'-fluoro-6,7,2',3'-indolomorphinan, 17-allyl-6,7-didehydro-4,5α-epoxy-3,14β-dihydroxy-1',7'-ethylene-6'-fluoro-6,7,2',3'-indolomorphinan, 17-cyclopropylmethyl-6,7-didehydro-4,5α-epoxy-3-hydroxy-14β-methoxy-1',7'-ethylene-6'-fluoro-6,7,2',3'-indolomorphinan, 17-allyl-6,7-didehydro-4,5α-epoxy-3-hydroxy-14β-methoxy-1',7'-ethylene-6'-fluoro-6,7,2',3'-indolomorphinan, 17-cyclopropylmethyl-6,7-didehydro-4,5α-epoxy-3-methoxy-14β-hydroxy-1',7'-ethylene-6'-fluoro-6,7,2',3'-indolomorphinan, 17-allyl-6,7-didehydro-4,5α-epoxy-3-methoxy-14β-hydroxy-1',7'-ethylene-6'-fluoro-6,7,2',3'-indolomorphinan, 17-cyclopropylmethyl-6,7-didehydro-4,5α-epoxy-3,14β-dimethoxy-1',7'-ethylene-6'-fluoro-6,7,2',3'-indolomorphinan, 17-allyl- 6,7-didehydro-4,5α-epoxy-3,14β-dimethoxy-1',7'-ethylene-6'-fluoro-6,7,2',3'-indolomorphinan, 17-cyclopropylmethyl-6,7-didehydro-4,5α-epoxy-3,14β-dihydroxy-1',7'-ethylene-4'-chloro-6,7,2',3'-indolomorphinan, 17-allyl-6,7-didehydro-4,5α-epoxy-3,14β-dihydroxy-1',7'-ethylene-4'-chloro-6,7,2',3'-indolomorphinan, 17-cyclopropylmethyl-6,7-didehydro-4,5α-epoxy-3-hydroxy-14β-methoxy-1',7'-ethylene-4'-chloro-6,7,2',3'-indolomorphinan, 17-allyl-6,7-didehydro-4,5α-epoxy-3-hydroxy-14β-methoxy-1',7'-ethylene-4'-chloro-6,7,2',3'-indolomorphinan, 17-cyclopropylmethyl-6,7-didehydro-4,5α-epoxy-3-methoxy-14β-hydroxy-1',7'-ethylene-4'-chloro-6,7,2',3'-indolomorphinan, 17-allyl-6,7-didehydro-4,5α-epoxy-3-methoxy-14β-hydroxy-1',7'-ethylene-4'-chloro-6,7,2',3'-indolomorphinan, 17-cyclopropylmethyl-6,7-didehydro-4,5α-epoxy-3,14β-dimethoxy-1',7'-ethylene-4'-chloro-6,7,2',3'-indolomorphinan, 17-allyl-6,7-didehydro-4,5α-epoxy-3,14β-dimethoxy-1',7'-ethylene-4'-chloro-6,7,2',3'-indolomorphinan, 17-cyclopropylmethyl-6,7-didehydro-4,5α-epoxy-3,14β-dihydroxy-1',7'-ethylene-5'-chloro-6,7,2',3'-indolomorphinan, 17-allyl-6,7-didehydro-4,5α-epoxy-3,14β-dihydroxy-1',7'-ethylene-5'-chloro-6,7,2',3'-indolomorphinan, 17-cyclopropylmethyl-6,7-didehydro-4,5α-epoxy-3-hydroxy-14β-methoxy-1',7'-ethylene-5'-chloro-6,7,2',3'-indolomorphinan, 17-allyl-6,7-didehydro-4,5α-epoxy-3-hydroxy-14β-methoxy-1',7'-ethylene-5'-chloro-6,7,2',3'-indolomorphinan, 17-cyclopropylmethyl-6,7-didehydro-4,5α-epoxy-3-methoxy-14β-hydroxy-1',7'-ethylene-5'-chloro-6,7,2',3'-indolomorphinan, 17-allyl-6,7-didehydro-4,5α-epoxy-3-methoxy-14β-hydroxy-1',7'-ethylene-5'-chloro-6,7,2',3'-indolomorphinan, 17-cyclopropylmethyl-6,7-didehydro-4,5α-epoxy-3,14β-dimethoxy-1',7'-ethylene-5'-chloro-6,7,2',3'-indolomorphinan, 17-allyl-6,7-didehydro-4,5α-epoxy-3,14β-dimethoxy-1',7'-ethylene-5'-chloro-6,7,2',3'-indolomorphinan, 17-cyclopropylmethyl-6,7-didehydro-4,5α-epoxy-3,14β-dihydroxy-1',7'-ethylene-6'-chloro-6,7,2',3'-indolomorphinan, 17-allyl-6,7-didehydro-4,5α-epoxy-3,14β-dihydroxy-1',7'-ethylene-6'-chloro-6,7,2',3'-indolomorphinan, 17-cyclopropylmethyl-6,7-didehydro-4,5α-epoxy-3-hydroxy-14β-methoxy-1',7'-ethylene-6'-chloro-6,7,2',3'-indolomorphinan, 17-allyl-6,7-didehydro-4,5α-epoxy-3-hydroxy-14β-methoxy-1',7'-ethylene-6'-chloro-6,7,2',3'-indolomorphinan, 17-cyclopropylmethyl-6,7-didehydro-4,5α-epoxy-3-methoxy-14β-hydroxy-1',7'-ethylene-6'-chloro-6,7,2',3'-indolomorphinan, 17-allyl-6,7-didehydro-4,5α-epoxy-3-methoxy-14β-hydroxy-1',7'-ethylene-6'-chloro-6,7,2',3'-indolomorphinan, 17-cyclopropylmethyl-6,7-didehydro-4,5α-epoxy-3,14β-dimethoxy-1',7'-ethylene-6'-chloro-6,7,2',3'-indolomorphinan, 17-allyl-6,7-didehydro-4,5α-epoxy-3,14β-dimethoxy-1',7'-ethylene-6'-chloro-6,7,2',3'-indolomorphinan, 17-cyclopropylmethyl-6,7-didehydro-4,5α-epoxy-3,14β-dihydroxy-1',7'-ethylene-4'-bromo- 6,7,2',3'-indolomorphinan, 17-allyl-6,7-didehydro-4,5α-epoxy-3,14β-dihydroxy-1',7'-ethylene-4'-bromo-6,7,2',3'-indolomorphinan, 17-cyclopropylmethyl-6,7-didehydro-4,5α-epoxy-3-hydroxy-14β-methoxy-1',7'-ethylene-4'-bromo-6,7,2',3'-indolomorphinan, 17-allyl-6,7-didehydro-4,5α-epoxy-3-hydroxy-14β-methoxy-1',7'-ethylene-4'-bromo-6,7,2',3'-indolomorphinan, 17-cyclopropylmethyl-6,7-didehydro-4,5α-epoxy-3-methoxy-14β-hydroxy-1',7'-ethylene-4'-bromo-6,7,2',3'-indolomorphinan, 17-allyl-6,7-didehydro-4,5α-epoxy-3-methoxy-14β-hydroxy-1',7'-ethylene-4'-bromo-6,7,2',3'-indolomorphinan, 17-cyclopropylmethyl-6,7-didehydro-4,5α-epoxy-3,14β-dimethoxy-1',7'-ethylene-4'-bromo-6,7,2',3'-indolomorphinan, 17-allyl-6,7-didehydro-4,5α-epoxy-3,14β-dimethoxy-1',7'-ethylene-4'-bromo-6,7,2',3'-indolomorphinan, 17-cyclopropylmethyl-6,7-didehydro-4,5α-epoxy-3,14β-dihydroxy-1',7'-ethylene-5'-bromo-6,7,2',3'-indolomorphinan, 17-allyl-6,7-didehydro-4,5α-epoxy-3,14β-dihydroxy-1',7'-ethylene-5'-bromo-6,7,2',3'-indolomorphinan, 17-cyclopropylmethyl-6,7-didehydro-4,5α-epoxy-3-hydroxy-14β-methoxy-1',7'-ethylene-5'-bromo-6,7,2',3'-indolomorphinan, 17-allyl-6,7-didehydro-4,5α-epoxy-3-hydroxy-14β-methoxy-1',7'-ethylene-5'-bromo-6,7,2',3'-indolomorphinan, 17-cyclopropylmethyl-6,7-didehydro-4,5α-epoxy-3-methoxy-14β-hydroxy-1',7'-ethylene-5'-bromo-6,7,2',3'-indolomorphinan, 17-allyl-6,7-didehydro-4,5α-epoxy-3-methoxy-14β-hydroxy- 1',7'-ethylene-5'-bromo-6,7,2',3'-indolomorphinan, 17-cyclopropylmethyl-6,7-didehydro-4,5α-epoxy-3,14β-dimethoxy-1',7'-ethylene-5'-bromo-6,7,2',3'-indolomorphinan, 17-allyl-6,7-didehydro-4,5α-epoxy-3,14β-dimethoxy-1',7'-ethylene-5'-bromo-6,7,2',3'-indolomorphinan, 17-cyclopropylmethyl-6,7-didehydro-4,5α-epoxy-3,14β-dihydroxy-1',7'-ethylene-6'-bromo-6,7,2',3'-indolomorphinan, 17-allyl-6,7-didehydro-4,5α-epoxy-3,14β-dihydroxy-1',7'-ethylene-6'-bromo-6,7,2',3'-indolomorphinan, 17-cyclopropylmethyl-6,7-didehydro-4,5α-epoxy-3-hydroxy-14β-methoxy-1',7'-ethylene-6'-bromo-6,7,2',3'-indolomorphinan, 17-allyl-6,7-didehydro-4,5α-epoxy-3-hydroxy-14β-methoxy-1',7'-ethylene-6'-bromo-6,7,2',3'-indolomorphinan, 17-cyclopropylmethyl-6,7-didehydro-4,5α-epoxy-3-methoxy-14β-hydroxy-1',7'-ethylene-6'-bromo-6,7,2',3'-indolomorphinan, 17-allyl-6,7-didehydro-4,5α-epoxy-3-methoxy-14β-hydroxy-1',7'-ethylene-6'-bromo-6,7,2',3'-indolomorphinan, 17-cyclopropylmethyl-6,7-didehydro-4,5α-epoxy-3,14β-dimethoxy-1',7'-ethylene-6'-bromo-6,7,2',3'-indolomorphinan, 17-allyl-6,7-didehydro-4,5α-epoxy-3,14β-dimethoxy-1',7'-ethylene-6'-bromo-6,7,2',3'-indolomorphinan, 17-cyclopropylmethyl-6,7-didehydro-4,5α-epoxy-3,14β-dihydroxy-1',7'-ethylene-4'-methyl-6,7,2',3'-indolomorphinan, 17-allyl-6,7-didehydro-4,5α-epoxy-3,14β-dihydroxy-1',7'-ethylene-4'-methyl-6,7,2',3'-indolomorphinan, 17-cyclopropylmethyl-6,7-didehydro-4,5α-epoxy-3-hydroxy- 14β-methoxy-1',7'-ethylene-4'-methyl-6,7,2',3'-indolomorphinan, 17-allyl-6,7-didehydro-4,5α-epoxy-3-hydroxy-14β-methoxy-1',7'-ethylene-4'-methyl-6,7,2',3'-indolomorphinan, 17-cyclopropylmethyl-6,7-didehydro-4,5α-epoxy-3-methoxy-14β-hydroxy-1',7'-ethylene-4'-methyl-6,7,2',3'-indolomorphinan, 17-allyl-6,7-didehydro-4,5α-epoxy-3-methoxy-14β-hydroxy-1',7'-ethylene-4'-methyl-6,7,2',3'-indolomorphinan, 17-cyclopropylmethyl-6,7-didehydro-4,5α-epoxy-3,14β-dimethoxy-1',7'-ethylene-4'-methyl-6,7,2',3'-indolomorphinan, 17-allyl-6,7-didehydro-4,5α-epoxy-3,14β-dimethoxy-1',7'-ethylene-4'-methyl-6,7,2',3'-indolomorphinan, 17-cyclopropylmethyl-6,7-didehydro-4,5α-epoxy-3,14β-dihydroxy-1',7'-ethylene-5'-methyl-6,7,2',3'-indolomorphinan, 17-allyl-6,7-didehydro-4,5α-epoxy-3,14β-dihydroxy-1',7'-ethylene-5'-methyl-6,7,2',3'-indolomorphinan, 17-cyclopropylmethyl-6,7-didehydro-4,5α-epoxy-3-hydroxy-14β-methoxy-1',7'-ethylene-5'-methyl-6,7,2',3'-indolomorphinan, 17-allyl-6,7-didehydro-4,5α-epoxy-3-hydroxy-14β-methoxy-1',7'-ethylene-5'-methyl-6,7,2',3'-indolomorphinan, 17-cyclopropylmethyl-6,7-didehydro-4,5α-epoxy-3-methoxy-14β-hydroxy-1',7'-ethylene-5'-methyl-6,7,2',3'-indolomorphinan, 17-allyl-6,7-didehydro-4,5α-epoxy-3-methoxy-14β-hydroxy-1',7'-ethylene-5'-methyl-6,7,2',3'-indolomorphinan, 17-cyclopropylmethyl-6,7-didehydro-4,5α-epoxy-3,14β-dimethoxy-1',7'-ethylene-5'-methyl-6,7,2',3'-indolomorphinan, 17-allyl-6,7-didehydro-4,5α-epoxy-3,14β-dimethoxy-1',7'-ethylene-5'-methyl-6,7,2',3'-indolomorphinan, 17-cyclopropylmethyl-6,7-didehydro-4,5α-epoxy-3,14β-dihydroxy-1',7'-ethylene-6'-methyl-6,7,2',3'-indolomorphinan, 17-allyl-6,7-didehydro-4,5α-epoxy-3,14β-dihydroxy-1',7'-ethylene-6'-methyl-6,7,2',3'-indolomorphinan, 17-cyclopropylmethyl-6,7-didehydro-4,5α-epoxy-3-hydroxy-14β-methoxy-1',7'-ethylene-6'-methyl-6,7,2',3'-indolomorphinan, 17-allyl-6,7-didehydro-4,5α-epoxy-3-hydroxy-14β-methoxy-1',7'-ethylene-6'-methyl-6,7,2',3'-indolomorphinan, 17-cyclopropylmethyl-6,7-didehydro-4,5α-epoxy-3-methoxy-14β-hydroxy-1',7'-ethylene-6'-methyl-6,7,2',3'-indolomorphinan, 17-allyl-6,7-didehydro-4,5α-epoxy-3-methoxy-14β-hydroxy-1',7'-ethylene-6'-methyl-6,7,2',3'-indolomorphinan, 17-cyclopropylmethyl-6,7-didehydro-4,5α-epoxy-3,14β-dimethoxy-1',7'-ethylene-6'-methyl-6,7,2',3'-indolomorphinan, 17-allyl-6,7-didehydro-4,5α-epoxy-3,14β-dimethoxy-1',7'-ethylene-6'-methyl-6,7,2',3'-indolomorphinan, 17-cyclopropylmethyl-6,7-didehydro-4,5α-epoxy-3,14β-dihydroxy-1',7'-ethylene-4'-methoxy-6,7,2',3'-indolomorphinan, 17-allyl-6,7-didehydro-4,5α-epoxy-3,14β-dihydroxy-1',7'-ethylene-4'-methoxy-6,7,2',3'-indolomorphinan, 17-cyclopropylmethyl-6,7-didehydro-4,5α-epoxy-3-hydroxy-14β-methoxy-1',7'-ethylene-4'-methoxy-6,7,2',3'-indolomorphinan, 17-allyl-6,7-didehydro-4,5α-epoxy-3-hydroxy-14β-methoxy-1',7'-ethylene-4'-methoxy-6,7,2',3'-indolomorphinan, 17-cyclopropylmethyl-6,7-didehydro-4,5α-epoxy-3-methoxy-14β-hydroxy-1',7'-ethylene-4'-methoxy-6,7,2',3'-indolomorphinan, 17-allyl-6,7-didehydro-4,5α-epoxy-3-methoxy-14β-hydroxy-1',7'-ethylene-4'-methoxy-6,7,2',3'-indolomorphinan, 17-cyclopropylmethyl-6,7-didehydro-4,5α-epoxy-3,14β-dimethoxy-1',7'-ethylene-4'-methoxy-6,7,2',3'-indolomorphinan, 17-allyl-6,7-didehydro-4,5α-epoxy-3,14β-dimethoxy-1',7'-ethylene-4'-methoxy-6,7,2',3'-indolomorphinan, 17-cyclopropylmethyl-6,7-didehydro-4,5α-epoxy-3,14β-dihydroxy-1',7'-ethylene-5'-methoxy-6,7,2',3'-indolomorphinan, 17-allyl-6,7-didehydro-4,5α-epoxy-3,14β-dihydroxy-1',7'-ethylene-5'-methoxy-6,7,2',3'-indolomorphinan, 17-cyclopropylmethyl-6,7-didehydro-4,5α-epoxy-3-hydroxy-14β-methoxy-1',7'-ethylene-5'-methoxy-6,7,2',3'-indolomorphinan, 17-allyl-6,7-didehydro-4,5α-epoxy-3-hydroxy-14β-methoxy-1',7'-ethylene-5'-methoxy-6,7,2',3'-indolomorphinan, 17-cyclopropylmethyl-6,7-didehydro-4,5α-epoxy-3-methoxy-14β-hydroxy-1',7'-ethylene-5'-methoxy-6,7,2',3'-indolomorphinan, 17-allyl-6,7-didehydro-4,5α-epoxy-3-methoxy-14β-hydroxy-1',7'-ethylene-5'-methoxy-6,7,2',3'-indolomorphinan, 17-cyclopropylmethyl-6,7-didehydro-4,5α-epoxy-3,14β-dimethoxy-1',7'-ethylene-5'-methoxy-6,7,2',3'-indolomorphinan, 17-allyl-6,7-didehydro-4,5α-epoxy-3,14β-dimethoxy-1',7'-ethylene-5'-methoxy-6,7,2',3'-indolomorphinan, 17-cyclopropylmethyl-6,7-didehydro-4,5α-epoxy-3,14β-dihydroxy-1',7'-ethylene-6'-methoxy-6,7,2',3'-indolomorphinan, 17-allyl-6,7-didehydro-4,5α-epoxy-3,14β-dihydroxy-1',7'-ethylene-6'-methoxy-6,7,2',3'-indolomorphinan, 17-cyclopropylmethyl-6,7-didehydro-4,5α-epoxy-3-hydroxy-14β-methoxy-1',7'-ethylene-6'-methoxy-6,7,2',3'-indolomorphinan, 17-allyl-6,7-didehydro-4,5α-epoxy-3-hydroxy-14β-methoxy-1',7'-ethylene-6'-methoxy-6,7,2',3'-indolomorphinan, 17-cyclopropylmethyl-6,7-didehydro-4,5α-epoxy-3-methoxy-14β-hydroxy-1',7'-ethylene-6'-methoxy-6,7,2',3'-indolomorphinan, 17-allyl-6,7-didehydro-4,5α-epoxy-3-methoxy-14β-hydroxy-1',7'-ethylene-6'-methoxy-6,7,2',3'-indolomorphinan, 17-cyclopropylmethyl-6,7-didehydro-4,5α-epoxy-3,14β-dimethoxy-1',7'-ethylene-6'-methoxy-6,7,2',3'-indolomorphinan, 17-allyl-6,7-didehydro-4,5α-epoxy-3,14β-dimethoxy-1',7'-ethylene-6'-methoxy-6,7,2',3'-indolomorphinan, 17-cyclopropylmethyl-6,7-didehydro-4,5α-epoxy-3,14β-dihydroxy-1',7'-ethylene-4'-nitro-6,7,2',3'-indolomorphinan, 17-allyl-6,7-didehydro-4,5α-epoxy-3,14β-dihydroxy-1',7'-ethylene-4'-nitro-6,7,2',3'-indolomorphinan, 17-cyclopropylmethyl-6,7-didehydro-4,5α-epoxy-3-hydroxy-14β-methoxy-1',7'-ethylene-4'-nitro-6,7,2',3'-indolomorphinan, 17-allyl-6,7-didehydro-4,5α-epoxy-3-hydroxy-14β-methoxy-1',7'-ethylene-4'-nitro-6,7,2',3'-indolomorphinan, 17-cyclopropylmethyl-6,7-didehydro-4,5α-epoxy-3-methoxy-14β-hydroxy-1',7'-ethylene-4'-nitro-6,7,2',3'-indolomorphinan, 17-allyl-6,7-didehydro-4,5α-epoxy-3-methoxy-14β-hydroxy-1',7'-ethylene-4'-nitro-6,7,2',3'-indolomorphinan, 17-cyclopropylmethyl-6,7-didehydro-4,5α-epoxy-3,14β-dimethoxy-1',7'-ethylene-4'-nitro-6,7,2',3'-indolomorphinan, 17-allyl-6,7-didehydro-4,5α-epoxy-3,14β-dimethoxy-1',7'-ethylene-4'-nitro-6,7,2',3'-indolomorphinan, 17-cyclopropylmethyl-6,7-didehydro-4,5α-epoxy-3,14β-dihydroxy-1',7'-ethylene-5'-nitro-6,7,2',3'-indolomorphinan, 17-allyl-6,7-didehydro-4,5α-epoxy-3,14β-dihydroxy-1',7'-ethylene-5'-nitro-6,7,2',3'-indolomorphinan, 17-cyclopropylmethyl-6,7-didehydro-4,5α-epoxy-3-hydroxy-14β-methoxy-1',7'-ethylene-5'-nitro-6,7,2',3'-indolomorphinan, 17-allyl-6,7-didehydro-4,5α-epoxy-3-hydroxy-14β-methoxy-1',7'-ethylene-5'-nitro-6,7,2',3'-indolomorphinan, 17-cyclopropylmethyl-6,7-didehydro-4,5α-epoxy-3-methoxy-14β-hydroxy-1',7'-ethylene-5'-nitro-6,7,2',3'-indolomorphinan, 17-allyl-6,7-didehydro-4,5α-epoxy-3-methoxy-14β-hydroxy-1',7'-ethylene-5'-nitro-6,7,2',3'-indolomorphinan, 17-cyclopropylmethyl-6,7-didehydro-4,5α-epoxy-3,14β-dimethoxy-1',7'-ethylene-5'-nitro-6,7,2',3'-indolomorphinan, 17-allyl-6,7-didehydro-4,5α-epoxy-3,14β-dimethoxy-1',7'-ethylene-5'-nitro-6,7,2',3'-indolomorphinan, 17-cyclopropylmethyl-6,7-didehydro-4,5α-epoxy-3,14β-dihydroxy-1',7'-ethylene-6'-nitro-6,7,2',3'-indolomorphinan, 17-allyl-6,7-didehydro-4,5α-epoxy-3,14β-dihydroxy-1',7'-ethylene-6'-nitro- 6,7,2',3'-indolomorphinan, 17-cyclopropylmethyl-6,7-didehydro-4,5α-epoxy-3-hydroxy-14β-methoxy-1',7'-ethylene-6'-nitro-6,7,2',3'-indolomorphinan, 17-allyl-6,7-didehydro-4,5α-epoxy-3-hydroxy-14β-methoxy-1',7'-ethylene-6'-nitro-6,7,2',3'-indolomorphinan, 17-cyclopropylmethyl-6,7-didehydro-4,5α-epoxy-3-methoxy-14β-hydroxy-1',7'-ethylene-6'-nitro-6,7,2',3'-indolomorphinan, 17-allyl-6,7- didehydro-4,5α-epoxy-3-methoxy-14β-hydroxy-1',7'-ethylene-6'-nitro-6,7,2',3'-indolomorphinan, 17-cyclopropylmethyl-6,7-didehydro-4,5α-epoxy-3,14β-dimethoxy-1',7'-ethylene-6'-nitro-6,7,2',3'-indolomorphinan, 17-allyl-6,7-didehydro-4,5α-epoxy-3,14β-dimethoxy-1',7'-ethylene-6'-nitro-6,7,2',3'-indolomorphinan, 17-cyclopropylmethyl-6,7-didehydro-4,5α-epoxy-3,14β-dihydroxy-1',7'-trimethylene-6,7,2',3'-indolomorphinan, 17-allyl-6,7-didehydro-4,5α-epoxy-3,14β-dihydroxy-1',7'-trimethylene-6,7,2',3'-indolomorphinan, 17-cyclopropylmethyl-6,7-didehydro-4,5α-epoxy-3-hydroxy-14β-methoxy-1',7'-trimethylene-6,7,2',3'-indolomorphinan, 17-allyl-6,7-didehydro-4,5α-epoxy-3-hydroxy-14β-methoxy-1',7'-trimethylene-6,7,2',3'-indolomorphinan, 17-cyclopropylmethyl-6,7-didehydro-4,5α-epoxy-3-methoxy-14β-hydroxy-1',7'-trimethylene-6,7,2',3'-indolomorphinan, 17-allyl-6,7-didehydro-4,5α-epoxy-3-methoxy-14β-hydroxy-1',7'-trimethylene-6,7,2',3'-indolomorphinan, 17-cyclopropylmethyl-6,7-didehydro-4,5α-epoxy-3,14β-dimethoxy-1',7'-trimethylene-6,7,2',3'-indolomorphinan, 17-allyl-6,7-didehydro-4,5α-epoxy-3,14β-dimethoxy-1',7'-trimethylene-6,7,2',3'-indolomorphinan, 17-cyclopropylmethyl-6,7-didehydro-4,5α-epoxy-3,14β-dihydroxy-1',7'-trimethylene-4'-fluoro-6,7,2',3'-indolomorphinan, 17-allyl-6,7-didehydro-4,5α-epoxy-3,14β-dihydroxy-1',7'-trimethylene-4'-fluoro-6,7,2',3'-indolomorphinan, 17-cyclopropylmethyl-6,7-didehydro-4,5α-epoxy-3-hydroxy-14β-methoxy-1',7'-trimethylene-4'-fluoro-6,7,2',3'-indolomorphinan, 17-allyl-6,7-didehydro-4,5α-epoxy-3-hydroxy-14β-methoxy-1',7'-trimethylene-4'-fluoro-6,7,2',3'-indolomorphinan, 17-cyclopropylmethyl-6,7-didehydro-4,5α-epoxy-3-methoxy-14β-hydroxy-1',7'-trimethylene-4'-fluoro-6,7,2',3'-indolomorphinan, 17-allyl-6,7-didehydro-4,5α-epoxy-3-methoxy-14β-hydroxy-1',7'-trimethylene-4'-fluoro-6,7,2',3'-indolomorphinan, 17-cyclopropylmethyl-6,7-didehydro-4,5α-epoxy-3,14β-dimethoxy-1',7'-trimethylene-4'-fluoro-6,7,2',3'-indolomorphinan, 17-allyl-6,7-didehydro-4,5α-epoxy-3,14β-dimethoxy-1',7'-trimethylene-4'-fluoro-6,7,2',3'-indolomorphinan, 17-cyclopropylmethyl-6,7-didehydro-4,5α-epoxy-3,14β-dihydroxy-1',7'-trimethylene-5'-fluoro-6,7,2',3'-indolomorphinan, 17-allyl-6,7-didehydro-4,5α-epoxy-3,14β-dihydroxy-1',7'-trimethylene-5'-fluoro-6,7,2',3'-indolomorphinan, 17-cyclopropylmethyl-6,7-didehydro-4,5α-epoxy-3-hydroxy-14β-methoxy-1',7'-trimethylene-5'-fluoro-6,7,2',3'-indolomorphinan, 17-allyl-6,7-didehydro-4,5α-epoxy-3-hydroxy-14β-methoxy-1',7'-trimethylene-5'-fluoro-6,7,2',3'-indolomorphinan, 17-cyclopropylmethyl-6,7-didehydro-4,5α-epoxy-3-methoxy-14β-hydroxy-1',7'-trimethylene-5'-fluoro-6,7,2',3'-indolomorphinan, 17-allyl-6,7-didehydro-4,5α-epoxy-3-methoxy-14β-hydroxy-1',7'-trimethylene-5'-fluoro-6,7,2',3'-indolomorphinan, 17-cyclopropylmethyl-6,7-didehydro-4,5α-epoxy-3,14β-dimethoxy-1',7'-trimethylene-5'-fluoro-6,7,2',3'-indolomorphinan, 17-allyl-6,7-didehydro-4,5α-epoxy-3,14β-dimethoxy-1',7'-trimethylene-5'-fluoro-6,7,2',3'-indolomorphinan, 17-cyclopropylmethyl-6,7-didehydro-4,5α-epoxy-3,14β-dihydroxy-1',7'-trimethylene-6'-fluoro-6,7,2',3'-indolomorphinan, 17-allyl-6,7-didehydro-4,5α-epoxy-3,14β-dihydroxy-1',7'-trimethylene-6'-fluoro-6,7,2',3'-indolomorphinan, 17-cyclopropylmethyl-6,7-didehydro-4,5α-epoxy-3-hydroxy-14β-methoxy-1',7'-trimethylene-6'-fluoro-6,7,2',3'-indolomorphinan, 17-allyl-6,7-didehydro-4,5α-epoxy-3-hydroxy-14β-methoxy-1',7'-trimethylene-6'-fluoro-6,7,2',3'-indolomorphinan, 17-cyclopropylmethyl-6,7-didehydro-4,5α-epoxy-3-methoxy-14β-hydroxy-1',7'-trimethylene-6'-fluoro-6,7,2',3'-indolomorphinan, 17-allyl-6,7-didehydro-4,5α-epoxy-3-methoxy-14β-hydroxy-1',7'-trimethylene-6'-fluoro-6,7,2',3'-indolomorphinan, 17-cyclopropylmethyl-6,7-didehydro-4,5α-epoxy-3,14β-dimethoxy-1',7'-trimethylene-6'-fluoro-6,7,2',3'-indolomorphinan, 17-allyl-6,7-didehydro-4,5α-epoxy-3,14β-dimethoxy-1',7'-trimethylene-6'-fluoro- 6,7,2',3'-indolomorphinan, 17-cyclopropylmethyl-6,7-didehydro-4,5α-epoxy-3,14β-dihydroxy-1',7'-trimethylene-4'-chloro-6,7,2',3'-indolomorphinan, 17-allyl-6,7-didehydro-4,5α-epoxy-3,14β-dihydroxy-1',7'-trimethylene-4'-chloro-6,7,2',3'-indolomorphinan, 17-cyclopropylmethyl-6,7-didehydro-4,5α-epoxy-3-hydroxy-14β-methoxy-1',7'-trimethylene-4'-chloro-6,7,2',3'-indolomorphinan, 17-allyl-6,7-didehydro-4,5α-epoxy-3-hydroxy-14β-methoxy-1',7'-trimethylene-4'-chloro-6,7,2',3'-indolomorphinan, 17-cyclopropylmethyl-6,7-didehydro-4,5α-epoxy-3-methoxy-14β-hydroxy-1',7'-trimethylene-4'-chloro-6,7,2',3'-indolomorphinan, 17-allyl-6,7-didehydro-4,5α-epoxy-3-methoxy-14β-hydroxy-1',7'-trimethylene-4'-chloro-6,7,2',3'-indolomorphinan, 17-cyclopropylmethyl-6,7-didehydro-4,5α-epoxy-3,14β-dimethoxy-1',7'-trimethylene-4'-chloro-6,7,2',3'-indolomorphinan, 17-allyl-6,7-didehydro-4,5α-epoxy-3,14β-dimethoxy-1',7'-trimethylene-4'-chloro-6,7,2',3'-indolomorphinan, 17-cyclopropylmethyl-6,7-didehydro-4,5α-epoxy-3,14β-dihydroxy-1',7'-trimethylene-5'-chloro-6,7,2',3'-indolomorphinan, 17-allyl-6,7-didehydro-4,5α-epoxy-3,14β-dihydroxy-1',7'-trimethylene-5'-chloro-6,7,2',3'-indolomorphinan, 17-cyclopropylmethyl-6,7-didehydro-4,5α-epoxy-3-hydroxy-14β-methoxy-1',7'-trimethylene-5'-chloro-6,7,2',3'-indolomorphinan, 17-allyl-6,7-didehydro-4,5α-epoxy-3-hydroxy-14β-methoxy-1',7'-trimethylene-5'-chloro-6,7,2',3'-indolomorphinan, 17-cyclopropylmethyl-6,7-didehydro- 4,5α-epoxy-3-methoxy-14β-hydroxy-1',7'-trimethylene-5'-chloro-6,7,2',3'-indolomorphinan, 17-allyl-6,7-didehydro-4,5α-epoxy-3-methoxy-14β-hydroxy-1',7'-trimethylene-5'-chloro-6,7,2',3'-indolomorphinan, 17-cyclopropylmethyl-6,7-didehydro-4,5α-epoxy-3,14β-dimethoxy-1',7'-trimethylene-5'-chloro-6,7,2',3'-indolomorphinan, 17-allyl-6,7-didehydro-4,5α-epoxy-3,14β-dimethoxy-1',7'-trimethylene-5'-chloro-6,7,2',3'-indolomorphinan, 17-cyclopropylmethyl-6,7-didehydro-4,5α-epoxy-3,14β-dihydroxy-1',7'-trimethylene-6'-chloro-6,7,2',3'-indolomorphinan, 17-allyl-6,7-didehydro-4,5α-epoxy-3,14β-dihydroxy-1',7'-trimethylene-6'-chloro-6,7,2',3'-indolomorphinan, 17-cyclopropylmethyl-6,7-didehydro-4,5α-epoxy-3-hydroxy-14β-methoxy-1',7'-trimethylene-6'-chloro-6,7,2',3'-indolomorphinan, 17-allyl-6,7-didehydro-4,5α-epoxy-3-hydroxy-14β-methoxy-1',7'-trimethylene-6'-chloro-6,7,2',3'-indolomorphinan, 17-cyclopropylmethyl-6,7-didehydro-4,5α-epoxy-3-methoxy-14β-hydroxy-1',7'-trimethylene-6'-chloro-6,7,2',3'-indolomorphinan, 17-allyl-6,7-didehydro-4,5α-epoxy-3-methoxy-14β-hydroxy-1',7'-trimethylene-6'-chloro-6,7,2',3'-indolomorphinan, 17-cyclopropylmethyl-6,7-didehydro-4,5α-epoxy-3,14β-dimethoxy-1',7'-trimethylene-6'-chloro-6,7,2',3'-indolomorphinan, 17-allyl-6,7-didehydro-4,5α-epoxy-3,14β-dimethoxy-1',7'-trimethylene-6'-chloro-6,7,2',3'-indolomorphinan, 17-cyclopropylmethyl-6,7-didehydro-4,5α-epoxy-3,14β-dihydroxy-1',7'-trimethylene-4'-bromo-6,7,2',3'-indolomorphinan, 17-allyl-6,7-didehydro-4,5α-epoxy-3,14β-dihydroxy-1',7'-trimethylene-4'-bromo-6,7,2',3'-indolomorphinan, 17-cyclopropylmethyl-6,7-didehydro-4,5α-epoxy-3-hydroxy-14β-methoxy-1',7'-trimethylene-4'-bromo-6,7,2',3'-indolomorphinan, 17-allyl-6,7-didehydro-4,5α-epoxy-3-hydroxy-14β-methoxy-1',7'-trimethylene-4'-bromo-6,7,2',3'-indolomorphinan, 17-cyclopropylmethyl-6,7-didehydro-4,5α-epoxy-3-methoxy-14β-hydroxy-1',7'- trimethylene-4'-bromo-6,7,2',3'-indolomorphinan, 17-allyl-6,7-didehydro-4,5α-epoxy-3-methoxy-14β-hydroxy-1',7'-trimethylene-4'-bromo-6,7,2',3'-indolomorphinan, 17-cyclopropylmethyl-6,7-didehydro-4,5α-epoxy-3,14β-dimethoxy-1',7'-trimethylene-4'-bromo-6,7,2',3'-indolomorphinan, 17-allyl-6,7-didehydro-4,5α-epoxy-3,14β-dimethoxy-1',7'-trimethylene-4'-bromo-6,7,2',3'-indolomorphinan, 17-cyclopropylmethyl-6,7-didehydro-4,5α-epoxy-3,14β-dihydroxy-1',7'-trimethylene-5'-bromo-6,7,2',3'-indolomorphinan, 17-allyl-6,7-didehydro-4,5α-epoxy-3,14β-dihydroxy-1',7'-trimethylene-5'-bromo-6,7,2',3'-indolomorphinan, 17-cyclopropylmethyl-6,7-didehydro-4,5α-epoxy-3-hydroxy-14β-methoxy-1',7'-trimethylene-5'-bromo-6,7,2',3'-indolomorphinan, 17-allyl-6,7-didehydro-4,5α-epoxy-3-hydroxy-14β-methoxy-1',7'-trimethylene-5'-bromo-6,7,2',3'-indolomorphinan, 17-cyclopropylmethyl-6,7-didehydro-4,5α-epoxy-3-methoxy-14β-hydroxy-1',7'-trimethylene-5'-bromo-6,7,2',3'-indolomorphinan, 17-allyl-6,7-didehydro-4,5α-epoxy-3-methoxy-14β-hydroxy-1',7'-trimethylene-5'-bromo-6,7,2',3'-indolomorphinan, 17-cyclopropylmethyl-6,7-didehydro-4,5α-epoxy-3,14β-dimethoxy-1',7'-trimethylene-5'-bromo-6,7,2',3'-indolomorphinan, 17-allyl-6,7-didehydro-4,5α-epoxy-3,14β-dimethoxy-1',7'-trimethylene-5'-bromo-6,7,2',3'-indolomorphinan, 17-cyclopropylmethyl-6,7-didehydro-4,5α-epoxy-3,14β-dihydroxy-1',7'-trimethylene-6'-bromo-6,7,2',3'-indolomorphinan, 17-allyl-6,7-didehydro-4,5α-epoxy-3,14β-dihydroxy-1',7'-trimethylene-6'-bromo-6,7,2',3'-indolomorphinan, 17-cyclopropylmethyl-6,7-didehydro-4,5α-epoxy-3-hydroxy-14β-methoxy-1',7'-trimethylene-6'-bromo-6,7,2',3'-indolomorphinan, 17-allyl-6,7-didehydro-4,5α-epoxy-3-hydroxy-14β-methoxy-1',7'-trimethylene-6'-bromo-6,7,2',3'-indolomorphinan, 17-cyclopropylmethyl-6,7-didehydro-4,5α-epoxy-3-methoxy-14β-hydroxy-1',7'-trimethylene-6'-bromo-6,7,2',3'-indolomorphinan, 17-allyl-6,7-didehydro-4,5α-epoxy-3-methoxy-14β-hydroxy-1',7'-trimethylene-6'-bromo-6,7,2',3'-indolomorphinan, 17-cyclopropylmethyl-6,7-didehydro-4,5α-epoxy-3,14β-dimethoxy-1',7'-trimethylene-6'-bromo-6,7,2',3'-indolomorphinan, 17-allyl-6,7-didehydro-4,5α-epoxy-3,14β-dimethoxy-1',7'-trimethylene-6'-bromo-6,7,2',3'-indolomorphinan, 17-cyclopropylmethyl-6,7-didehydro-4,5α-epoxy-3,14β-dihydroxy-1',7'-trimethylene-4'-methyl-6,7,2',3'-indolomorphinan, 17-allyl-6,7-didehydro-4,5α-epoxy-3,14β-dihydroxy-1',7'-trimethylene-4'-methyl-6,7,2',3'-indolomorphinan, 17-cyclopropylmethyl-6,7-didehydro-4,5α-epoxy-3-hydroxy-14β-methoxy-1',7'-trimethylene-4'-methyl-6,7,2',3'-indolomorphinan, 17-allyl-6,7-didehydro-4,5α-epoxy-3-hydroxy-14β-methoxy-1',7'-trimethylene-4'-methyl-6,7,2',3'-indolomorphinan, 17-cyclopropylmethyl-6,7-didehydro-4,5α-epoxy-3-methoxy-14β-hydroxy-1',7'-trimethylene-4'-methyl-6,7,2',3'-indolomorphinan, 17-allyl-6,7-didehydro-4,5α-epoxy-3-methoxy-14β-hydroxy-1',7'-trimethylene-4'-methyl-6,7,2',3'-indolomorphinan, 17-cyclopropylmethyl-6,7-didehydro-4,5α-epoxy-3,14β-dimethoxy-1',7'-trimethylene-4'-methyl-6,7,2',3'-indolomorphinan, 17-allyl-6,7-didehydro-4,5α-epoxy-3,14β-dimethoxy-1',7'-trimethylene-4'-methyl-6,7,2',3'-indolomorphinan, 17-cyclopropylmethyl-6,7-didehydro-4,5α-epoxy-3,14β-dihydroxy-1',7'-trimethylene-5'-methyl-6,7,2',3'-indolomorphinan, 17-allyl-6,7-didehydro-4,5α-epoxy-3,14β-dihydroxy-1',7'-trimethylene-5'-methyl-6,7,2',3'-indolomorphinan, 17-cyclopropylmethyl-6,7-didehydro-4,5α-epoxy-3-hydroxy-14β-methoxy-1',7'-trimethylene-5'-methyl-6,7,2',3'-indolomorphinan, 17-allyl-6,7-didehydro-4,5α-epoxy-3-hydroxy-14β-methoxy-1',7'-trimethylene-5'-methyl-6,7,2',3'-indolomorphinan, 17-cyclopropylmethyl-6,7-didehydro-4,5α-epoxy-3-methoxy-14β-hydroxy-1',7'-trimethylene-5'-methyl-6,7,2',3'-indolomorphinan, 17-allyl-6,7-didehydro-4,5α-epoxy-3-methoxy-14β-hydroxy-1',7'-trimethylene-5'-methyl-6,7,2',3'-indolomorphinan, 17-cyclopropylmethyl-6,7-didehydro-4,5α-epoxy-3,14β-dimethoxy-1',7'-trimethylene-5'-methyl-6,7,2',3'-indolomorphinan, 17-allyl-6,7-didehydro-4,5α-epoxy-3,14β-dimethoxy-1',7'-trimethylene-5'-methyl-6,7,2',3'-indolomorphinan, 17-cyclopropylmethyl-6,7-didehydro-4,5α-epoxy-3,14β-dihydroxy-1',7'-trimethylene-6'-methyl-6,7,2',3'-indolomorphinan, 17-allyl-6,7-didehydro-4,5α-epoxy-3,14β-dihydroxy-1',7'-trimethylene-6'-methyl-6,7,2',3'-indolomorphinan, 17-cyclopropylmethyl-6,7-didehydro-4,5α-epoxy-3-hydroxy-14β-methoxy-1',7'-trimethylene-6'-methyl-6,7,2',3'-indolomorphinan, 17-allyl-6,7-didehydro-4,5α-epoxy-3-hydroxy-14β-methoxy-1',7'-trimethylene-6'-methyl-6,7,2',3'-indolomorphinan, 17-cyclopropylmethyl-6,7-didehydro-4,5α-epoxy-3-methoxy-14β-hydroxy-1',7'-trimethylene-6'-methyl-6,7,2',3'-indolomorphinan, 17-allyl-6,7-didehydro-4,5α-epoxy-3-methoxy-14β-hydroxy-1',7'-trimethylene-6'-methyl-6,7,2',3'-indolomorphinan, 17-cyclopropylmethyl-6,7-didehydro-4,5α-epoxy-3,14β-dimethoxy-1',7'-trimethylene-6'-methyl-6,7,2',3'-indolomorphinan, 17-allyl-6,7-didehydro-4,5(α-epoxy-3,14β-dimethoxy-1',7'-trimethylene-6'-methyl-6,7,2',3'-indolomorphinan, 17-cyclopropylmethyl-6,7-didehydro-4,5α-epoxy-3,14β-dihydroxy-1',7'-trimethylene-4'-methoxy-6,7,2',3'-indolomorphinan, 17-allyl-6,7-didehydro-4,5α-epoxy-3,14β-dihydroxy-1',7'-trimethylene-4'-methoxy-6,7,2',3'-indolomorphinan, 17-cyclopropylmethyl-6,7-didehydro-4,5α-epoxy-3-hydroxy-14β-methoxy-1',7'-trimethylene-4'-methoxy-6,7,2',3'-indolomorphinan, 17-allyl-6,7-didehydro-4,5α-epoxy-3-hydroxy-14β-methoxy-1',7'-trimethylene-4'-methoxy-6,7,2',3'-indolomorphinan, 17-cyclopropylmethyl-6,7-didehydro-4,5α-epoxy-3-methoxy-14β-hydroxy-1',7'-trimethylene-4'-methoxy-6,7,2',3'-indolomorphinan, 17-allyl-6,7-didehydro-4,5α-epoxy-3-methoxy-14β-hydroxy-1',7'-trimethylene-4'-methoxy-6,7,2',3'-indolomorphinan, 17-cyclopropylmethyl-6,7-didehydro-4,5α-epoxy-3,14β-dimethoxy-1',7'-trimethylene-4'-methoxy-6,7,2',3'-indolomorphinan, 17-allyl-6,7-didehydro-4,5α-epoxy-3,14β-dimethoxy-1',7'-trimethylene-4'-methoxy-6,7,2',3'-indolomorphinan, 17-cyclopropylmethyl-6,7-didehydro-4,5α-epoxy-3,14β-dihydroxy-1',7'-trimethylene-5'-methoxy-6,7,2',3'-indolomorphinan, 17-allyl-6,7-didehydro-4,5α-epoxy-3,14β-dihydroxy-1',7'-trimethylene-5'-methoxy-6,7,2',3'-indolomorphinan, 17-cyclopropylmethyl-6,7-didehydro-4,5α-epoxy-3-hydroxy-14β-methoxy-1',7'-trimethylene-5'-methoxy-6,7,2',3'-indolomorphinan, 17-allyl-6,7-didehydro-4,5α-epoxy-3-hydroxy-14β-methoxy-1',7'-trimethylene-5'-methoxy-6,7,2',3'-indolomorphinan, 17-cyclopropylmethyl-6,7-didehydro-4,5α-epoxy-3-methoxy-14β-hydroxy-1',7'-trimethylene-5'-methoxy-6,7,2',3'-indolomorphinan, 17-allyl-6,7-didehydro-4,5α-epoxy-3-methoxy-14β-hydroxy-1',7'-trimethylene-5'-methoxy-6,7,2',3'-indolomorphinan, 17-cyclopropylmethyl-6,7-didehydro-4,5α-epoxy-3,14β-dimethoxy-1',7'-trimethylene- 5'-methoxy-6,7,2',3'-indolomorphinan, 17-allyl-6,7-didehydro-4,5α-epoxy-3,14β-dimethoxy-1',7'-trimethylene-5'-methoxy-6,7,2',3'-indolomorphinan, 17-cyclopropylmethyl-6,7-didehydro-4,5α-epoxy-3,14β-dihydroxy-1',7'-trimethylene-6'-methoxy-6,7,2',3'-indolomorphinan, 17-allyl-6,7-didehydro-4,5α-epoxy-3,14β-dihydroxy-1',7'-trimethylene-6'-methoxy-6,7,2',3'-indolomorphinan, 17-cyclopropylmethyl-6,7-didehydro-4,5α-epoxy-3-hydroxy-14β-methoxy-1',7'- trimethylene-6'-methoxy-6,7,2',3'-indolomorphinan, 17-allyl-6,7-didehydro-4,5α-epoxy-3-hydroxy-14β-methoxy-1',7'-trimethylene-6'-methoxy-6,7,2',3'-indolomorphinan, 17-cyclopropylmethyl-6,7-didehydro-4,5α-epoxy-3-methoxy-14β-hydroxy-1',7'-trimethylene-6'-methoxy-6,7,2',3'-indolomorphinan, 17-allyl-6,7-didehydro-4,5α-epoxy-3-methoxy-14β-hydroxy-1',7'-trimethylene-6'-methoxy-6,7,2',3'-indolomorphinan, 17-cyclopropylmethyl-6,7-didehydro-4,5α-epoxy-3,14β-dimethoxy-1',7'-trimethylene-6'-methoxy-6,7,2',3'-indolomorphinan, 17-allyl-6,7-didehydro-4,5α-epoxy-3,14β-dimethoxy-1',7'-trimethylene-6'-methoxy-6,7,2',3'-indolomorphinan, 17-cyclopropylmethyl-6,7-didehydro-4,5α-epoxy-3,14β-dihydroxy-1',7'-trimethylene-4'-nitro-6,7,2',3'-indolomorphinan, 17-allyl-6,7-didehydro-4,5α-epoxy-3,14β-dihydroxy-1',7'-trimethylene-4'-nitro-6,7,2',3'-indolomorphinan, 17-cyclopropylmethyl-6,7-didehydro-4,5α-epoxy-3-hydroxy-14β-methoxy-1',7'-trimethylene-4'-nitro-6,7,2',3'-indolomorphinan, 17-allyl-6,7-didehydro-4,5α-epoxy-3-hydroxy-14β-methoxy-1',7'-trimethylene-4'-nitro-6,7,2',3'-indolomorphinan, 17-cyclopropylmethyl-6,7-didehydro-4,5α-epoxy-3-methoxy-14β-hydroxy-1',7'-trimethylene-4'-nitro-6,7,2',3'-indolomorphinan, 17-allyl-6,7-didehydro-4,5α-epoxy-3-methoxy-14β-hydroxy-1',7'-trimethylene-4'-nitro-6,7,2',3'-indolomorphinan, 17-cyclopropylmethyl-6,7-didehydro-4,5α-epoxy-3,14β-dimethoxy-1',7'-trimethylene-4'-nitro-6,7,2',3'-indolomorphinan, 17-allyl-6,7-didehydro-4,5α-epoxy-3,14β-dimethoxy-1',7'-trimethylene-4'-nitro-6,7,2',3'-indolomorphinan, 17-cyclopropylmethyl-6,7-didehydro-4,5α-epoxy-3,14β-dihydroxy-1',7'-trimethylene-5'-nitro-6,7,2',3'-indolomorphinan, 17-allyl-6,7-didehydro-4,5α-epoxy-3,14β-dihydroxy-1',7'-trimethylene-5'-nitro-6,7,2',3'-indolomorphinan, 17-cyclopropylmethyl-6,7-didehydro-4,5α-epoxy-3-hydroxy-14β-methoxy-1',7'-trimethylene-5'-nitro-6,7,2',3'-indolomorphinan, 17-allyl-6,7-didehydro-4,5α-epoxy-3-hydroxy-14β-methoxy-1',7'-trimethylene-5'-nitro-6,7,2',3'-indolomorphinan, 17-cyclopropylmethyl-6,7-didehydro-4,5α-epoxy-3-methoxy-14β-hydroxy-1',7'-trimethylene-5'-nitro-6,7,2',3'-indolomorphinan, 17-allyl-6,7-didehydro-4,5α-epoxy-3-methoxy-14β-hydroxy-1',7'-trimethylene-5'-nitro-6,7,2',3'-indolomorphinan, 17-cyclopropylmethyl-6,7-didehydro-4,5α-epoxy-3,14β-dimethoxy-1',7'-trimethylene-5'-nitro-6,7,2',3'-indolomorphinan, 17-allyl-6,7-didehydro-4,5α-epoxy-3,14β-dimethoxy-1',7'-trimethylene-5'-nitro-6,7,2',3'-indolomorphinan, 17-cyclopropylmethyl-6,7-didehydro-4,5α-epoxy-3,14β-dihydroxy-1',7'-trimethylene-6'-nitro-6,7,2',3'-indolomorphinan, 17-allyl-6,7-didehydro-4,5α-epoxy-3,14β-dihydroxy-1',7'-trimethylene-6'-nitro-6,7,2',3'-indolomorphinan, 17-cyclopropylmethyl-6,7-didehydro-4,5α-epoxy-3-hydroxy-14β-methoxy-1',7'-trimethylene-6'-nitro-6,7,2',3'-indolomorphinan, 17-allyl-6,7-didehydro-4,5α-epoxy-3-hydroxy-14β-methoxy-1',7'-trimethylene-6'-nitro-6,7,2',3'-indolomorphinan, 17-cyclopropylmethyl-6,7-didehydro-4,5α-epoxy-3-methoxy-14β-hydroxy-1',7'-trimethylene-6'-nitro-6,7,2',3'-indolomorphinan, 17-allyl-6,7-didehydro-4,5α-epoxy-3-methoxy-14β-hydroxy-1',7'-trimethylene-6'-nitro-6,7,2',3'-indolomorphinan, 17-cyclopropylmethyl-6,7-didehydro-4,5α-epoxy-3,14β-dimethoxy-1',7'-trimethylene-6'-nitro-6,7,2',3'-indolomorphinan, 17-allyl-6,7-didehydro-4,5α-epoxy-3,14β-dimethoxy-1',7'-trimethylene-6'-nitro-6,7,2',3'-indolomorphinan, 17-cyclopropylmethyl-6,7-didehydro-4,5α-epoxy-3,14β-dihydroxy-1',7'-tetramethylene-6,7,2',3'-indolomorphinan, 17-allyl-6,7-didehydro-4,5α-epoxy-3,14β-dihydroxy-1',7'-tetramethylene-6,7,2',3'-indolomorphinan, 17-cyclopropylmethyl-6,7-didehydro-4,5α-epoxy-3-hydroxy-14β-methoxy-1',7'-tetramethylene-6,7,2',3'-indolomorphinan, 17-allyl-6,7-didehydro-4,5α-epoxy-3-hydroxy-14β-methoxy-1',7'-tetramethylene-6,7,2',3'-indolomorphinan, 17-cyclopropylmethyl-6,7-didehydro-4,5α-epoxy-3-methoxy-14β-hydroxy-1',7'-tetramethylene-6,7,2',3'-indolomorphinan, 17-allyl-6,7-didehydro-4,5α-epoxy-3-methoxy-14β-hydroxy-1',7'-tetramethylene-6,7,2',3'-indolomorphinan, 17-cyclopropylmethyl-6,7-didehydro-4,5α-epoxy-3,14β-dimethoxy-1',7'-tetramethylene-6,7,2',3'-indolomorphinan, 17-allyl-6,7-didehydro-4,5α-epoxy-3,14β-dimethoxy-1',7'-tetramethylene-6,7,2',3'-indolomorphinan, 17-cyclopropylmethyl-6,7-didehydro-4,5α-epoxy-3,14β-dihydroxy-1',7'-tetramethylene-4'-fluoro-6,7,2',3'-indolomorphinan, 17-allyl-6,7-didehydro-4,5α-epoxy-3,14β-dihydroxy-1',7'-tetramethylene-4'-fluoro-6,7,2',3'-indolomorphinan, 17-cyclopropylmethyl-6,7-didehydro-4,5α-epoxy-3-hydroxy-14β-methoxy-1',7'-tetramethylene-4'-fluoro-6,7,2',3'-indolomorphinan, 17-allyl-6,7-didehydro-4,5α-epoxy-3-hydroxy-14β-methoxy-1',7'-tetramethylene-4'-fluoro-6,7,2',3'-indolomorphinan, 17-cyclopropylmethyl-6,7-didehydro-4,5α-epoxy-3-methoxy-14β-hydroxy-1',7'-tetramethylene-4'-fluoro-6,7,2',3'-indolomorphinan, 17-allyl-6,7-didehydro-4,5α-epoxy-3-methoxy-14β-hydroxy-1',7'-tetramethylene-4'-fluoro-6,7,2',3'-indolomorphinan, 17-cyclopropylmethyl-6,7-didehydro-4,5α-epoxy-3,14β-dimethoxy-1',7'-tetramnethylene-4'-fluoro-6,7,2',3'-indolomorphinan, 17-allyl-6,7-didehydro-4,5α-epoxy-3,14β-dimethoxy-1',7'-tetramethylene-4'-fluoro-6,7,2',3'-indolomorphinan, 17-cyclopropylmethyl-6,7-didehydro-4,5α-epoxy-3,14β-dihydroxy-1',7'-tetramethylene-5'-fluoro-6,7,2',3'-indolomorphinan, 17-allyl-6,7-didehydro-4,5α-epoxy-3,14β-dihydroxy-1',7'-tetramethylene-5'-fluoro-6,7,2',3'-indolomorphinan, 17-cyclopropylmethyl-6,7-didehydro-4,5α-epoxy-3-hydroxy-14β-methoxy-1',7'-tetramethylene-5'-fluoro-6,7,2',3'-indolomorphinan, 17-allyl-6,7-didehydro-4,5α-epoxy-3-hydroxy-14β-methoxy-1',7'-tetramethylene-5'-fluoro-6,7,2',3'-indolomorphinan, 17-cyclopropylmethyl-6,7-didehydro-4,5α-epoxy-3-methoxy-14β-hydroxy-1',7'-tetramethylene-5'-fluoro-6,7,2',3'-indolomorphinan, 17-allyl-6,7-didehydro-4,5α-epoxy-3-methoxy-14β-hydroxy-1',7'-tetramethylene-5'-fluoro-6,7,2',3'-indolomorphinan, 17-cyclopropylmethyl-6,7-didehydro-4,5α-epoxy-3,14β-dimethoxy-1',7'-tetramethylene-5'-fluoro-6,7,2',3'-indolomorphinan, 17-allyl-6,7-didehydro-4,5α-epoxy-3,14β-dimethoxy-1',7'-tetramethylene-5'-fluoro-6,7,2',3'-indolomorphinan, 17-cyclopropylmethyl-6,7-didehydro-4,5α-epoxy-3,14β-dihydroxy-1',7'-tetramethylene-6'-fluoro-6,7,2',3'-indolomorphinan, 17-allyl-6,7-didehydro-4,5α-epoxy-3,14β-dihydroxy-1',7'-tetramethylene-6'-fluoro-6,7,2',3'-indolomorphinan, 17-cyclopropylmethyl-6,7-didehydro-4,5α-epoxy-3-hydroxy-14β-methoxy-1',7'-tetramethylene-6'-fluoro-6,7,2',3'-indolomorphinan, 17-allyl-6,7-didehydro-4,5α-epoxy-3-hydroxy-14β-methoxy-1',7'-tetramethylene-6'-fluoro-6,7,2',3'-indolomorphinan, 17-cyclopropylmethyl-6,7-didehydro-4,5α-epoxy-3-methoxy-14β-hydroxy-1',7'-tetramethylene-6'-fluoro-6,7,2',3'-indolomorphinan, 17-allyl-6,7-didehydro-4,5α-epoxy-3-methoxy-14β-hydroxy-1',7'-tetramethylene-6'-fluoro-6,7,2',3'-indolomorphinan, 17-cyclopropylmethyl-6,7-didehydro-4,5α-epoxy-3,14β-dimethoxy-1',7'-tetramethylene-6'-fluoro-6,7,2',3'-indolomorphinan, 17-allyl-6,7-didehydro-4,5α-epoxy-3,14β-dimethoxy-1',7'-tetramethylene-6'-fluoro-6,7,2',3'-indolomorphinan, 17-cyclopropylmethyl-6,7-didehydro-4,5α-epoxy-3,14β-dihydroxy-1',7'-tetramethylene-4'-chloro-6,7,2',3'- indolomorphinan, 17-allyl-6,7-didehydro-4,5α-epoxy-3,14β-dihydroxy-1',7'-tetramethylene-4'-chloro-6,7,2',3'-indolomorphinan, 17-cyclopropylmethyl-6,7-didehydro-4,5α-epoxy-3-hydroxy-14β-methoxy-1',7'-tetramethylene-4'-chloro-6,7,2',3'-indolomorphinan, 17-allyl-6,7-didehydro-4,5α-epoxy-3-hydroxy-14β-methoxy-1',7'-tetramethylene-4'-chloro-6,7,2',3'-indolomorphinan, 17-cyclopropylmethyl-6,7-didehydro-4,5α-epoxy-3-methoxy-14β-hydroxy-1',7'-tetramethylene-4'-chloro-6,7,2',3'-indolomorphinan, 17-allyl-6,7-didehydro-4,5α-epoxy-3-methoxy-14β-hydroxy-1',7'-tetramethylene-4'-chloro-6,7,2',3'-indolomorphinan, 17-cyclopropylmethyl-6,7-didehydro-4,5α-epoxy-3,14β-dimethoxy-1',7'-tetramethylene-4'-chloro-6,7,2',3'-indolomorphinan, 17-allyl-6,7-didehydro-4,5α-epoxy-3,14β-dimethoxy-1',7'-tetramethylene-4'-chloro-6,7,2',3'-indolomorphinan, 17-cyclopropylmethyl-6,7-didehydro-4,5α-epoxy-3,14β-dihydroxy-1',7'-tetramethylene-5'-chloro-6,7,2',3'-indolomorphinan, 17-allyl-6,7-didehydro-4,5α-epoxy-3,14β-dihydroxy-1',7'-tetramethylene-5'-chloro-6,7,2',3'-indolomorphinan, 17-cyclopropylmethyl-6,7-didehydro-4,5α-epoxy-3-hydroxy-14β-methoxy-1',7'-tetramethylene-5'-chloro-6,7,2',3'-indolomorphinan, 17-allyl-6,7-didehydro-4,5α-epoxy-3-hydroxy-14β-methoxy-1',7'-tetramethylene-5'-chloro-6,7,2',3'-indolomorphinan, 17-cyclopropylmethyl-6,7-didehydro-4,5α-epoxy-3-methoxy-14β-hydroxy-1',7'-tetramethylene-5'-chloro-6,7,2',3'-indolomorphinan, 17-allyl-6,7-didehydro-4,5α-epoxy-3-methoxy-14β-hydroxy-1',7'-tetramethylene-5'-chloro-6,7,2',3'-indolomorphinan, 17-cyclopropylmethyl-6,7-didehydro-4,5α-epoxy-3,14β-dimethoxy-1',7'-tetramethylene-5'-chloro-6,7,2',3'-indolomorphinan, 17-allyl-6,7-didehydro-4,5α-epoxy-3,14β-dimethoxy-1',7'-tetramethylene-5'-chloro-6,7,2',3'-indolomorphinan, 17-cyclopropylmethyl-6,7-didehydro-4,5α-epoxy-3,14β-dihydroxy-1',7'-tetramethylene-6'-chloro-6,7,2',3'-indolomorphinan, 17-allyl-6,7-didehydro-4,5α-epoxy-3,14β-dihydroxy-1',7'-tetramethylene-6'-chloro-6,7,2',3'-indolomorphinan, 17-cyclopropylmethyl-6,7-didehydro-4,5α-epoxy-3-hydroxy-14β-methoxy-1',7'-tetramethylene-6'-chloro-6,7,2',3'-indolomorphinan, 17-allyl-6,7-didehydro-4,5α-epoxy-3-hydroxy-14β-methoxy-1',7'-tetramethylene-6'-chloro-6,7,2',3'-indolomorphinan, 17-cyclopropylmethyl-6,7-didehydro-4,5α-epoxy-3-methoxy-14β-hydroxy-1',7'-tetramethylene-6'-chloro-6,7,2',3'-indolomorphinan, 17-allyl-6,7-didehydro-4,5α-epoxy-3-methoxy-14β-hydroxy-1',7'-tetramethylene-6'-chloro-6,7,2',3'-indolomorphinan, 17-cyclopropylmethyl-6,7-didehydro-4,5α-epoxy-3,14β-dimethoxy-1',7'-tetramethylene-6'-chloro-6,7,2',3'-indolomorphinan, 17-allyl-6,7-didehydro-4,5α-epoxy-3,14β-dimethoxy-1',7'-tetramethylene-6'-chloro-6,7,2',3'-indolomorphinan, 17-cyclopropylmethyl-6,7-didehydro-4,5α-epoxy-3,14β-dihydroxy-1',7'-tetramethylene-4'-bromo-6,7,2',3'-indolomorphinan, 17-allyl-6,7-didehydro-4,5α-epoxy-3,14β-dihydroxy-1',7'-tetramethylene-4'-bromo-6,7,2',3'-indolomorphinan, 17-cyclopropylmethyl-6,7-didehydro-4,5α-epoxy-3-hydroxy-14β-methoxy-1',7'-tetramethylene-4'-bromo-6,7,2',3'-indolomorphinan, 17-allyl-6,7-didehydro-4,5α-epoxy-3-hydroxy-14β-methoxy-1',7'-tetramethylene-4'-bromo-6,7,2',3'-indolomorphinan, 17-cyclopropylmethyl-6,7-didehydro-4,5α-epoxy-3-methoxy-14β-hydroxy-1',7'-tetramethylene-4'-bromo-6,7,2',3'-indolomorphinan, 17-allyl-6,7-didehydro-4,5α-epoxy-3-methoxy-14β-hydroxy-1',7'-tetramethylene-4'-bromo-6,7,2',3'-indolomorphinan, 17-cyclopropylmethyl-6,7-didehydro-4,5α-epoxy-3,14β-dimethoxy-1',7'-tetramethylene-4'-bromo-6,7,2',3'-indolomorphinan, 17-allyl-6,7-didehydro-4,5α-epoxy-3,14β-dimethoxy-1',7'-tetramethylene-4'-bromo-6,7,2',3'-indolomorphinan, 17-cyclopropylmethyl-6,7-didehydro-4,5α-epoxy-3,14β-dihydroxy-1',7'-tetramethylene-5'-bromo-6,7,2',3'-indolomorphinan, 17-allyl-6,7-didehydro-4,5α-epoxy-3,14β-dihydroxy-1',7'-tetramethylene-5'-bromo-6,7,2',3'-indolomorphinan, 17-cyclopropylmethyl-6,7-didehydro-4,5α-epoxy-3-hydroxy-14β-methoxy-1',7'-tetramethylene-5'-bromo-6,7,2',3'-indolomorphinan, 17-allyl-6,7-didehydro-4,5α-epoxy-3-hydroxy-14β-methoxy-1',7'-tetramethylene-5'-bromo-6,7,2',3'-indolomorphinan, 17-cyclopropylmethyl-6,7-didehydro-4,5α-epoxy-3-methoxy-14β-hydroxy-1',7'-tetramethylene-5'-bromo-6,7,2',3'-indolomorphinan, 17-allyl-6,7-didehydro-4,5α-epoxy-3-methoxy-14β-hydroxy-1',7'-tetramethylene-5'-bromo-6,7,2',3'-indolomorphinan, 17-cyclopropylmethyl-6,7-didehydro-4,5α-epoxy-3,14β-dimethoxy-1',7'-tetramethylene-5'-bromo-6,7,2',3'-indolomorphinan, 17-allyl-6,7-didehydro-4,5α-epoxy-3,14β-dimethoxy-1',7'-tetramethylene-5'-bromo-6,7,2',3'-indolomorphinan, 17-cyclopropylmethyl-6,7-didehydro-4,5α-epoxy-3,14βdihydroxy-1',7'-tetramethylene-6'-bromo-6,7,2',3'-indolomorphinan, 17-allyl-6,7-didehydro-4,5α-epoxy-3,14β-dihydroxy-1',7'-tetramethylene-6'-bromo-6,7,2',3'-indolomorphinan, 17-cyclopropylmethyl-6,7-didehydro-4,5α-epoxy-3-hydroxy-14β-methoxy-1',7'-tetramethylene-6'-bromo-6,7,2',3'-indolomorphinan, 17-allyl-6,7-didehydro-4,5α-epoxy-3-hydroxy-14β-methoxy-1',7'-tetramethylene-6'-bromo-6,7,2',3'-indolomorphinan, 17-cyclopropylmethyl-6,7-didehydro-4,5α-epoxy-3-methoxy-14β-hydroxy-1',7'-tetramethylene-6'-bromo-6,7,2',3'-indolomorphinan, 17-allyl-6,7-didehydro-4,5α-epoxy-3-methoxy-14β-hydroxy-1',7'-tetramethylene-6'-bromo-6,7,2',3'-indolomorphinan, 17-cyclopropylmethyl-6,7-didehydro-4,5α-epoxy-3,14β-dimethoxy-1',7'-tetramethylene-6'-bromo-6,7,2',3'-indolomorphinan, 17-allyl-6,7-didehydro-4,5α-epoxy-3,14β-dimethoxy-1',7'-tetramethylene-6'-bromo-6,7,2',3'-indolomorphinan, 17-cyclopropylmethyl-6,7-didehydro-4,5α-epoxy-3,14β-dihydroxy-1',7'-tetramethylene-4'-methyl-6,7,2',3'-indolomorphinan, 17-allyl-6,7-didehydro-4,5α-epoxy-3,14β-dihydroxy-1',7'-tetramethylene-4'-methyl-6,7,2',3'-indolomorphinan, 17-cyclopropylmethyl-6,7-didehydro-4,5α-epoxy-3-hydroxy-14β-methoxy-1',7'-tetramethylene-4'-methyl-6,7,2',3'-indolomorphinan, 17-allyl-6,7-didehydro-4,5α-epoxy-3-hydroxy-14β-methoxy-1',7'-tetramethylene-4'-methyl-6,7,2',3'-indolomorphinan, 17-cyclopropylmethyl-6,7-didehydro-4,5α-epoxy-3-methoxy-14β-hydroxy-1',7'-tetramethylene-4'-methyl-6,7,2',3'-indolomorphinan, 17-allyl-6,7-didehydro-4,5α-epoxy-3-methoxy-14β-hydroxy-1',7'-tetramethylene-4'-methyl-6,7,2',3'-indolomorphinan, 17-cyclopropylmethyl-6,7-didehydro-4,5α-epoxy-3,14β-dimethoxy-1',7'-tetramethylene-4'-methyl-6,7,2',3'-indolomorphinan, 17-allyl-6,7-didehydro-4,5α-epoxy-3,14β-dimethoxy-1',7'-tetramethylene-4'-methyl-6,7,2',3'-indolomorphinan, 17-cyclopropylmethyl-6,7-didehydro-4,5α-epoxy-3,14β-dihydroxy-1',7'-tetramethylene-5'-methyl-6,7,2',3'-indolomorphinan, 17-allyl-6,7-didehydro-4,5α-epoxy-3,14β-dihydroxy-1',7'-tetramethylene-5'-methyl-6,7,2',3'-indolomorphinan, 17-cyclopropylmethyl-6,7-didehydro-4,5α-epoxy-3-hydroxy-14β-methoxy-1',7'-tetramethylene-5'-methyl-6,7,2',3'-indolomorphinan, 17-allyl-6,7-didehydro-4,5α-epoxy-3-hydroxy-14β-methoxy-1',7'-tetramethylene-5'-methyl-6,7,2',3'-indolomorphinan, 17-cyclopropylmethyl-6,7-didehydro-4,5α-epoxy-3-methoxy-14β-hydroxy-1',7'-tetramethylene-5'-methyl-6,7,2',3'-indolomorphinan, 17-allyl-6,7-didehydro-4,5α-epoxy- 3-methoxy-14β-hydroxy-1',7'-tetramethylene-5'-methyl-6,7,2',3'-indolomorphinan, 17-cyclopropylmethyl-6,7-didehydro-4,5α-epoxy-3,14β-dimethoxy-1',7'-tetramethylene-5'-methyl-6,7,2',3'-indolomorphinan, 17-allyl-6,7-didehydro-4,5α-epoxy-3,14β-dimethoxy-1',7'-tetramethylene-5'-methyl-6,7,2',3'-indolomorphinan, 17-cyclopropylmethyl-6,7-didehydro-4,5α-epoxy-3,14β-dihydroxy-1',7'-tetramethylene-6'-methyl-6,7,2',3'-indolomorphinan, 17-allyl-6,7-didehydro-4,5α-epoxy-3,14β-dihydroxy-1',7'-tetramethylene-6'-methyl-6,7,2',3'-indolomorphinan, 17-cyclopropylmethyl-6,7-didehydro-4,5α-epoxy-3-hydroxy-14β-methoxy-1',7'-tetramethylene-6'-methyl-6,7,2',3'-indolomorphinan, 17-allyl-6,7-didehydro-4,5α-epoxy-3-hydroxy-14β-methoxy-1',7'-tetramethylene-6'-methyl-6,7,2',3'-indolomorphinan, 17-cyclopropylmethyl-6,7-didehydro-4,5α-epoxy-3-methoxy-14β-hydroxy-1',7'-tetramethylene-6'-methyl-6,7,2',3'-indolomorphinan, 17-allyl-6,7-didehydro-4,5α-epoxy-3-methoxy-14β-hydroxy-1',7'-tetramethylene-6'-methyl-6,7,2',3'-indolomorphinan, 17-cyclopropylmethyl-6,7-didehydro-4,5α-epoxy-3,14β-dimethoxy-1',7'-tetramethylene-6'-methyl-6,7,2',3'-indolomorphinan, 17-allyl-6,7-didehydro-4,5α-epoxy-3,14β-dimethoxy-1',7'-tetramethylene-6'-methyl-6,7,2',3'-indolomorphinan, 17-cyclopropylmethyl-6,7-didehydro-4,5α-epoxy-3,14β-dihydroxy-1',7'-tetramethylene-4'-methoxy-6,7,2',3'-indolomorphinan, 17-allyl-6,7-didehydro-4,5α-epoxy-3,14β-dihydroxy-1',7'-tetramethylene-4'-methoxy-6,7,2',3'-indolomorphinan, 17-cyclopropylmethyl-6,7-didehydro-4,5α-epoxy-3-hydroxy-14β-methoxy-1',7'-tetramethylene-4'-methoxy-6,7,2',3'-indolomorphinan, 17-allyl-6,7-didehydro-4,5α-epoxy-3-hydroxy-14β-methoxy-1',7'-tetramethylene-4'-methoxy-6,7,2',3'-indolomorphinan, 17-cyclopropylmethyl-6,7-didehydro-4,5α-epoxy-3-methoxy-14β-hydroxy-1',7'-tetramethylene-4'-methoxy-6,7,2',3'-indolomorphinan, 17-allyl-6,7-didehydro-4,5α-epoxy-3-methoxy-14β-hydroxy-1',7'-tetramethylene-4'-methoxy-6,7,2',3'-indolomorphinan, 17-cyclopropylmethyl-6,7-didehydro-4,5α-epoxy-3,14β-dimethoxy-1',7'-tetramethylene-4'-methoxy-6,7,2',3'-indolomorphinan, 17-allyl-6,7-didehydro-4,5α-epoxy-3,14β-dimethoxy-1',7'-tetramethylene-4'-methoxy-6,7,2',3'-indolomorphinan, 17-cyclopropylmethyl-6,7-didehydro-4,5α-epoxy-3,14β-dihydroxy-1',7'-tetramethylene-5'-methoxy-6,7,2',3'-indolomorphinan, 17-allyl-6,7-didehydro-4,5α-epoxy-3,14β-dihydroxy-1',7'-tetramethylene-5'-methoxy-6,7,2',3'-indolomorphinan, 17-cyclopropylmethyl-6,7-didehydro-4,5α-epoxy-3-hydroxy-14β-methoxy-1',7'-tetramethylene-5'-methoxy-6,7,2',3'-indolomorphinan, 17-allyl-6,7-didehydro-4,5α-epoxy-3-hydroxy-14β-methoxy-1',7'-tetramethylene-5'-methoxy-6,7,2',3'-indolomorphinan, 17-cyclopropylmethyl-6,7-didehydro-4,5α-epoxy-3-methoxy-14β-hydroxy-1',7'-tetramethylene-5'-methoxy-6,7,2',3'-indolomorphinan, 17-allyl-6,7-didehydro-4,5α-epoxy-3-methoxy-14β-hydroxy-1',7'-tetramethylene-5'-methoxy-6,7,2',3'-indolomorphinan, 17-cyclopropylmethyl-6,7-didehydro-4,5α-epoxy-3,14β-dimethoxy-1',7'-tetramethylene-5'-methoxy-6,7,2',3'-indolomorphinan, 17-allyl-6,7-didehydro-4,5α-epoxy-3,14β-dimethoxy-1',7'-tetramethylene-5'-methoxy-6,7,2',3'-indolomorphinan, 17-cyclopropylmethyl-6,7-didehydro-4,5α-epoxy-3,14β-dihydroxy-1',7'-tetramethylene-6'-methoxy-6,7,2',3'-indolomorphinan, 17-allyl-6,7-didehydro-4,5α-epoxy-3,14β-dihydroxy-1',7'-tetramethylene-6'-methoxy-6,7,2',3'-indolomorphinan, 17-cyclopropylmethyl-6,7-didehydro-4,5α-epoxy-3-hydroxy-14β-methoxy-1',7'-tetramethylene-6'-methoxy-6,7,2',3'-indolomorphinan, 17-allyl-6,7-didehydro-4,5α-epoxy-3-hydroxy-14β-methoxy-1',7'-tetramethylene-6'-methoxy-6,7,2',3'-indolomorphinan, 17-cyclopropylmethyl-6,7-didehydro-4,5α-epoxy-3-methoxy-14β-hydroxy-1',7'-tetramethylene-6'-methoxy-6,7,2',3'-indolomorphinan, 17-allyl-6,7-didehydro-4,5α-epoxy-3-methoxy-14β-hydroxy-1',7'-tetramethylene-6'-methoxy-6,7,2',3'-indolomorphinan, 17-cyclopropylmethyl-6,7-didehydro-4,5α-epoxy-3,14β-dimethoxy-1',7'-tetramethylene-6'-methoxy-6,7,2',3'-indolomorphinan, 17-allyl-6,7-didehydro-4,5α-epoxy-3,14β-dimethoxy-1',7'-tetramethylene-6'-methoxy-6,7,2',3'-indolomorphinan, 17-cyclopropylmethyl-6,7-didehydro-4,5α-epoxy-3,14β-dihydroxy-1',7'-tetramethylene-4'-nitro-6,7,2',3'-indolomorphinan, 17-allyl-6,7-didehydro-4,5α-epoxy-3,14β-dihydroxy-1',7'-tetramethylene-4'-nitro-6,7,2',3'-indolomorphinan, 17-cyclopropylmethyl-6,7-didehydro-4,5α-epoxy-3-hydroxy-14β-methoxy-1',7'-tetramethylene-4'-nitro-6,7,2',3'-indolomorphinan, 17-allyl-6,7-didehydro-4,5α-epoxy-3-hydroxy-14β-methoxy-1',7'-tetramethylene-4'-nitro-6,7,2',3'-indolomorphinan, 17-cyclopropylmethyl-6,7-didehydro-4,5α-epoxy-3-methoxy-14β-hydroxy-1',7'-tetramethylene-4'-nitro-6,7,2',3'-indolomorphinan, 17-allyl-6,7-didehydro-4,5α-epoxy-3-methoxy-14β-hydroxy-1',7'-tetramethylene-4'-nitro-6,7,2',3'-indolomorphinan, 17-cyclopropylmethyl-6,7-didehydro-4,5α-epoxy-3,14β-dimethoxy-1',7'-tetramethylene-4'-nitro-6,7,2',3'-indolomorphinan, 17-allyl-6,7-didehydro-4,5α-epoxy-3,14β-dimethoxy-1',7'-tetramethylene-4'-nitro-6,7,2',3'-indolomorphinan, 17-cyclopropylmethyl-6,7-didehydro-4,5α-epoxy-3,14β-dihydroxy-1',7'-tetramethylene-5'-nitro-6,7,2',3'-indolomorphinan, 17-allyl-6,7-didehydro-4,5α-epoxy-3,14β-dihydroxy-1',7'-tetramethylene-5'-nitro-6,7,2',3'-indolomorphinan, 17-cyclopropylmethyl-6,7-didehydro-4,5α-epoxy-3-hydroxy-14β-methoxy-1',7'-tetramethylene-5'-nitro-6,7,2',3'-indolomorphinan, 17-allyl-6,7-didehydro-4,5α-epoxy-3-hydroxy-14β-methoxy-1',7'-tetramethylene-5'-nitro-6,7,2',3'-indolomorphinan, 17-cyclopropylmethyl-6,7-didehydro-4,5α-epoxy-3-methoxy-14β-hydroxy-1',7'-tetramethylene-5'-nitro-6,7,2',3'-indolomorphinan, 17-allyl-6,7-didehydro-4,5α-epoxy-3-methoxy-14β-hydroxy-1',7'-tetramethylene-5'-nitro-6,7,2',3'-indolomorphinan, 17-cyclopropylmethyl-6,7-didehydro-4,5α-epoxy-3,14β-dimethoxy-1',7'-tetramethylene-5'-nitro-6,7,2',3'-indolomorphinan, 17-allyl-6,7-didehydro-4,5α-epoxy-3,14β-dimethoxy-1',7'-tetramethylene-5'-nitro-6,7,2',3'-indolomorphinan, 17-cyclopropylmethyl-6,7-didehydro-4,5α-epoxy-3,14β-dihydroxy-1',7'-tetramethylene-6'-nitro-6,7,2',3'-indolomorphinan, 17-allyl-6,7-didehydro-4,5α-epoxy-3,14β-dihydroxy-1',7'-tetramethylene-6'-nitro-6,7,2',3'-indolomorphinan, 17-cyclopropylmethyl-6,7-didehydro-4,5α-epoxy-3-hydroxy-14β-methoxy-1',7'-tetramethylene-6'-nitro-6,7,2',3'-indolomorphinan, 17-allyl-6,7-didehydro-4,5α-epoxy-3-hydroxy-14β-methoxy-1',7'-tetramethylene-6'-nitro-6,7,2',3'-indolomorphinan, 17-cyclopropylmethyl-6,7-didehydro-4,5α-epoxy-3-methoxy-14β-hydroxy-1',7'-tetramethylene-6'-nitro-6,7,2',3'-indolomorphinan, 17-allyl-6,7-didehydro-4,5α-epoxy-3-methoxy-14β-hydroxy-1',7'-tetramethylene-6'-nitro-6,7,2',3'-indolomorphinan, 17-cyclopropylmethyl-6,7-didehydro-4,5α-epoxy-3,14β-dimethoxy-1',7'-tetramethylene-6'-nitro-6,7,2',3'-indolomorphinan, 17-allyl-6,7-didehydro-4,5α-epoxy-3,14β-dimethoxy-1',7'-tetramethylene-6'-nitro-6,7,2',3'-indolomorphinan, 6,7-didehydro-4,5α-epoxy-3,14β-dihydroxy-1',7'-ethylene-6,7,2',3'-indolomorphinan, 17-methyl-6,7-didehydro-4,5α-epoxy-3,14β-dihydroxy-1',7'-ethylene-6,7,2',3'-indolomorphinan, 17-cyclobutylmethyl-6,7-didehydro-4,5α-epoxy-3,14β- dihydroxy-1',7'-ethylene-6,7,2',3'-indolomorphinan, 17-(3-butenyl)-6,7-didehydro-4,5α-epoxy-3,14β-dihydroxy-1',7'-ethylene-6,7,2',3'-indolomorphinan, 17-phenethyl-6,7-didehydro-4,5α-epoxy-3,14β-dihydroxy-1',7'-ethylene-6,7,2',3'-indolomorphinan, 17-benzyl-6,7-didehydro-4,5α-epoxy-3,14β-dihydroxy-1',7'-ethylene-6,7,2',3'-indolomorphinan, 17-butyl-6,7-didehydro-4,5α-epoxy-3,14β-dihydroxy-1',7'-ethylene-6,7,2',3'-indolomorphinan, 17-(furan-2-ylmethyl)-6,7-didehydro-4,5α-epoxy-3,14β-dihydroxy-1',7'-ethylene-6,7,2',3'-indolomorphinan, 17-cinnamyl-6,7-didehydro-4,5α-epoxy-3,14β-dihydroxy-1',7'-ethylene-6,7,2',3'-indolomorphinan, 17-cyclohexylmethyl-6,7-didehydro-4,5α-epoxy-3,14β-dihydroxy-1',7'-ethylene- 6,7,2',3'-indolomorphinan, 17-(thiophene-2-ylethyl)-6,7-didehydro-4,5α-epoxy-3,14β-dihydroxy-1',7'-ethylene-6,7,2',3'-indolomorphinan, 17-prenyl-6,7-didehydro-4,5α-epoxy-3,14β-dihydroxy-1',7'-ethylene-6,7,2',3'-indolomorphinan, 6,7-didehydro-4,5α-epoxy-3-hydroxy-14β-methoxy-1',7'-ethylene-6,7,2',3'-indolomorphinan, 17-methyl-6,7-didehydro-4,5α-epoxy-3-hydroxy-14β-methoxy-1',7'-ethylene-6,7,2',3'-indolomorphinan, 17-cyclobutylmethyl-6,7-didehydro-4,5α-epoxy-3-hydroxy-14β-methoxy-1',7'-ethylene-6,7,2',3'-indolomorphinan, 17-(3-butenyl)-6,7-didehydro-4,5α-epoxy-3-hydroxy-14β-methoxy-1',7'-ethylene-6,7,2',3'-indolomorphinan, 17-phenethyl-6,7-didehydro-4,5α-epoxy-3-hydroxy-14β-methoxy-1',7'-ethylene-6,7,2',3'-indolomorphinan, 17-benzyl-6,7-didehydro-4,5α-epoxy-3-hydroxy-14β-methoxy-1',7'-ethylene-6,7,2',3'-indolomorphinan, 17-butyl-6,7-didehydro-4,5α-epoxy-3-hydroxy-14β-methoxy-1',7'-ethylene-6,7,2',3'-indolomorphinan, 17-(furan-2-ylmthyl)-6,7-didehydro-4,5α-epoxy-3-hydroxy-14β-methoxy-1',7'-ethylene-6,7,2',3'-indolomorphinan, 17-cinnamyl-6,7-didehydro-4,5α-epoxy-3-hydroxy-14β-methoxy-1',7'-ethylene-6,7,2',3'-indolomorphinan, 17-cyclohexylmethyl-6,7-didehydro-4,5α-epoxy-3-hydroxy-14β-methoxy-1',7'-ethylene-6,7,2',3'-indolomorphinan, 17-(thiophene-2-ylethyl)-6,7-didehydro-4,5α-epoxy-3-hydroxy-14β-methoxy-1',7'-ethylene-6,7,2',3'-indolomorphinan, 17-prenyl-6,7-didehydro-4,5α-epoxy-3-hydroxy-14β-methoxy- 1',7'-ethylene-6,7,2',3'-indolomorphinan, 6,7-didehydro-4,5α-epoxy-3-methoxy-14β-hydroxy-1',7'-ethylene-6,7,2',3'-indolomorphinan, 17-methyl-6,7-didehydro-4,5α-epoxy-3-methoxy-14β-hydroxy-1',7'-ethylene-6,7,2',3'-indolomorphinan, 17-cyclobutylmethyl-6,7-didehydro-4,5α-epoxy-3-methoxy-14β-hydroxy-1',7'-ethylene-6,7,2',3'-indolomorphinan, 17-(3-butenyl)-6,7-didehydro-4,5α-epoxy-3-methoxy-14β-hydroxy-1',7'-ethylene-6,7,2',3'-indolomorphinan, 17-phenethyl-6,7-didehydro-4,5α-epoxy-3-methoxy-14β-hydroxy-1',7'-ethylene-6,7,2',3'-indolomorphinan, 17-benzyl-6,7-didehydro-4,5α-epoxy-3-methoxy-14β-hydroxy-1',7'-ethylene-6,7,2',3'-indolomorphinan, 17-butyl-6,7-didehydro-4,5α-epoxy-3-methoxy-14β-hydroxy-1',7'-ethylene-6,7,2',3'-indolomorphinan, 17-(furan-2-ylmthyl)-6,7-didehydro-4,5α-epoxy-3-methoxy-14β-hydroxy-1',7'-ethylene-6,7,2',3'-indolomorphinan, 17-cinnamyl-6,7-didehydro-4,5α-epoxy-3-methoxy-14β-hydroxy-1',7'-ethylene-6,7,2',3'-indolomorphinan, 17-cyclohexylmethyl-6,7-didehydro-4,5α-epoxy-3-methoxy-14β-hydroxy-1',7'-ethylene-6,7,2',3'-indolomorphinan, 17-(thiophene-2-ylethyl)-6,7-didehydro-4,5α-epoxy-3-methoxy-14β-hydroxy-1',7'-ethylene-6,7,2',3'-indolomorphinan, 17-prenyl-6,7-didehydro-4,5α-epoxy-3-methoxy-14β-hydroxy-1',7'-ethylene-6,7,2',3'-indolomorphinan, 6,7-didehydro-4,5α-epoxy-3,14β-dimethoxy-1',7'-ethylene-6,7,2',3'-indolomorphinan, 17-methyl-6,7-didehydro-4,5α-epoxy-3,14β-dimethoxy-1',7'-ethylene-6,7,2',3'-indolomorphinan, 17-cyclobutylmethyl-6,7-didehydro-4,5α-epoxy-3,14β-dimethoxy-1',7'-ethylene-6,7,2',3'-indolomorphinan, 17-(3-butenyl)-6,7-didehydro-4,5α-epoxy-3,14β-dimethoxy-1',7'-ethylene-6,7,2',3'-indolomorphinan, 17-phenethyl-6,7-didehydro-4,5α-epoxy-3,14β-dimethoxy-1',7'-ethylene-6,7,2',3'-indolomorphinan, 17-benzyl-6,7-didehydro-4,5α-epoxy-3,14β-dimethoxy-1',7'-ethylene-6,7,2',3'-indolomorphinan, 17-butyl-6,7-didehydro-4,5α-epoxy-3,14β-dimethoxy-1',7'-ethylene-6,7,2',3'-indolomorphinan, 17-(furan-2-ylmthyl)-6,7-didehydro-4,5α-epoxy-3,14β-dimethoxy-1',7'-ethylene-6,7,2',3'-indolomorphinan, 17-cinnamyl-6,7-didehydro-4,5α-epoxy-3,14β-dimethoxy-1',7'-ethylene-6,7,2',3'-indolomorphinan, 17-cyclohexylmethyl-6,7-didehydro-4,5α-epoxy-3,14β-dimethoxy-1',7'-ethylene-6,7,2',3'-indolomorphinan, 17-(thiophene-2-ylethyl)-6,7-didehydro-4,5α-epoxy-3,14β-dimethoxy-1',7'-ethylene-6,7,2',3'-indolomorphinan, 17-prenyl-6,7-didehydro-4,5α-epoxy-3,14β-dimethoxy-1',7'-ethylene-6,7,2',3'-indolomorphinan, 6,7-didehydro-4,5α-epoxy-3,14β-dihydroxy-1',7'-trimethylene-6,7,2',3'-indolomorphinan, 17-methyl-6,7-didehydro-4,5α-epoxy-3,14β-dihydroxy-1',7'-trimethylene-6,7,2',3'-indolomorphinan, 17-cyclobutylmethyl-6,7-didehydro-4,5α-epoxy-3,14β-dihydroxy-1',7'-trimethylene-6,7,2',3'-indolomorphinan, 17-(3-butenyl)-6,7-didehydro-4,5α-epoxy-3,14β-dihydroxy-1',7'-trimethylene-6,7,2',3'-indolomorphinan, 17-phenethyl-6,7-didehydro-4,5α-epoxy-3,14β-dihydroxy-1',7'-trimethylene-6,7,2',3'-indolomorphinan, 17-benzyl-6,7-didehydro-4,5α-epoxy-3,14β-dihydroxy-1',7'-trimethylene-6,7,2',3'-indolomorphinan, 17-butyl-6,7-didehydro-4,5α-epoxy-3,14β-dihydroxy-1',7'-trimethylene-6,7,2',3'-indolomorphinan, 17-(furan-2-ylmthyl)-6,7-didehydro-4,5α-epoxy-3,14β-dihydroxy-1',7'-trimethylene-6,7,2',3'-indolomorphinan, 17-cinnamyl-6,7-didehydro-4,5α-epoxy-3,14β-dihydroxy-1',7'-trimethylene-6,7,2',3'-indolomorphinan, 17-cyclohexylmethyl-6,7-didehydro-4,5α-epoxy-3,14β-dihydroxy-1',7'-trimethylene-6,7,2',3'-indolomorphinan, 17-(thiophene-2-ylethyl)-6,7-didehydro-4,5α-epoxy-3,14β-dihydroxy-1',7'-trimethylene-6,7,2',3'-indolomorphinan, 17-prenyl-6,7-didehydro-4,5α-epoxy-3,14β-dihydroxy-1',7'-trimethylene-6,7,2',3'-indolomorphinan, 6,7-didehydro-4,5α-epoxy-3-hydroxy-14β-methoxy-1',7'-trimethylene-6,7,2',3'-indolomorphinan, 17-methyl-6,7-didehydro-4,5α-epoxy-3-hydroxy-14β-methoxy-1',7'-trimethylene-6,7,2',3'-indolomorphinan, 17-cyclobutylmethyl-6,7-didehydro-4,5α-epoxy-3-hydroxy-14β-methoxy-1',7'-trimethylene-6,7,2',3'-indolomorphinan, 17-(3-butenyl)-6,7-didehydro-4,5α-epoxy-3-hydroxy-14β-methoxy-1',7'-trimethylene-6,7,2',3'-indolomorphinan, 17-phenethyl-6,7-didehydro-4,5α-epoxy-3-hydroxy-14β-methoxy-1',7'-trimethylene-6,7,2',3'-indolomorphinan, 17-benzyl-6,7-didehydro-4,5α-epoxy-3-hydroxy-14β-methoxy-1',7'-trimethylene-6,7,2',3'-indolomorphinan, 17-butyl-6,7-didehydro-4,5α-epoxy-3-hydroxy-14β-methoxy-1',7'-trimethylene-6,7,2',3'-indolomorphinan, 17-(furan-2-ylmthyl)-6,7-didehydro-4,5α-epoxy-3-hydroxy-14β-methoxy-1',7'-trimethylene-6,7,2',3'-indolomorphinan, 17-cinnamyl-6,7-didehydro-4,5α-epoxy-3-hydroxy-14β-methoxy-1',7'-trimethylene-6,7,2',3'-indolomorphinan, 17-cyclohexylmethyl-6,7-didehydro-4,5α-epoxy-3-hydroxy-14β-methoxy-1',7'-trimethylene-6,7,2',3'-indolomorphinan, 17-(thiophene-2-ylethyl)-6,7-didehydro-4,5α-epoxy-3-hydroxy-14β-methoxy-1',7'-trimethylene-6,7,2',3'-indolomorphinan, 17-prenyl-6,7- didehydro-4,5α-epoxy-3-hydroxy-14β-methoxy-1',7'-trimethylene-6,7,2',3'-indolomorphinan, 6,7-didehydro-4,5α-epoxy-3-methoxy-14β-hydroxy-1',7'-trimethylene-6,7,2',3'-indolomorphinan, 17-methyl-6,7-didehydro-4,5α-epoxy-3-methoxy-14β-hydroxy-1',7'-trimethylene-6,7,2',3'-indolomorphinan, 17-cyclobutylmethyl-6,7-didehydro-4,5α-epoxy-3-methoxy-14β-hydroxy-1',7'-trimethylene-6,7,2',3'-indolomorphinan, 17-(3-butenyl)-6,7-didehydro-4,5α-epoxy-3-methoxy-14β-hydroxy-1',7'-trimethylene-6,7,2',3'-indolomorphinan, 17-phenethyl-6,7-didehydro-4,5α-epoxy-3-methoxy-14β-hydroxy-1',7'-trimethylene-6,7,2',3'-indolomorphinan, 17-benzyl-6,7-didehydro-4,5α-epoxy-3-methoxy-14β-hydroxy-1',7'-trimethylene-6,7,2',3'-indolomorphinan, 17-butyl-6,7-didehydro-4,5α-epoxy-3-methoxy-14β-hydroxy-1',7'-trimethylene-6,7,2',3'-indolomorphinan, 17-(furan-2-ylmthyl)-6,7-didehydro-4,5α-epoxy-3-methoxy-14β-hydroxy-1',7'-trimethylene-6,7,2',3'-indolomorphinan, 17-cinnamyl-6,7-didehydro-4,5α-epoxy-3-methoxy-14β-hydroxy-1',7'-trimethylene-6,7,2',3'-indolomorphinan, 17-cyclohexylmethyl-6,7-didehydro-4,5α-epoxy-3-methoxy-14β-hydroxy-1',7'-trimethylene-6,7,2',3'-indolomorphinan, 17-(thiophene-2-ylethyl)-6,7-didehydro-4,5α-epoxy-3-methoxy-14β-hydroxy-1',7'-trimethylene-6,7,2',3'-indolomorphinan, 17-prenyl-6,7-didehydro-4,5α-epoxy-3-methoxy-14β-hydroxy-1',7'-trimethylene-6,7,2',3'-indolomorphinan, 6,7-didehydro-4,5α-epoxy-3,14β-dimethoxy-1',7'-trimethylene-6,7,2',3'-indolomorphinan, 17-methyl-6,7-didehydro-4,5α-epoxy-3,14β-dimethoxy-1',7'-trimethylene-6,7,2',3'-indolomorphinan, 17-cyclobutylmethyl-6,7-didehydro-4,5α-epoxy-3,14β-dimethoxy-1',7'-trimethylene-6,7,2',3'-indolomorphinan, 17-(3-butenyl)-6,7-didehydro-4,5α-epoxy-3,14β-dimethoxy-1',7'-trimethylene-6,7,2',3'-indolomorphinan, 17-phenethyl-6,7-didehydro-4,5α-epoxy-3,14β-dimethoxy-1',7'-trimethylene-6,7,2',3'-indolomorphinan, 17-benzyl-6,7-didehydro-4,5α-epoxy-3,14β-dimethoxy-1',7'-trimethylene-6,7,2',3'-indolomorphinan, 17-butyl-6,7-didehydro-4,5α-epoxy-3,14β-dimethoxy-1',7'-trimethylene-6,7,2',3'-indolomorphinan, 17-(furan-2-ylmthyl)-6,7-didehydro-4,5α-epoxy-3,14β-dimethoxy-1',7'-trimethylene-6,7,2',3'-indolomorphinan, 17-cinnamyl-6,7-didehydro-4,5α-epoxy-3,14β-dimethoxy-1',7'-trimethylene-6,7,2',3'-indolomorphinan, 17-cyclohexylmethyl-6,7-didehydro-4,5α-epoxy-3,14β-dimethoxy-1',7'-trimethylene-6,7,2',3'-indolomorphinan, 17-(thiophene-2-ylethyl)-6,7-didehydro-4,5α-epoxy-3,14β-dimethoxy-1',7'-trimethylene-6,7,2',3'-indolomorphinan, 17-prenyl-6,7-didehydro-4,5α-epoxy-3,14β-dimethoxy-1',7'-trimethylene-6,7,2',3'-indolomorphinan, 6,7-didehydro-4,5α-epoxy-3,14β-dihydroxy-1',7'-tetramethylene-6,7,2',3'-indolomorphinan, 17-methyl-6,7-didehydro-4,5α-epoxy-3,14β-dihydroxy-1',7'-tetramethylene-6,7,2',3'-indolomorphinan, 17-cyclobutylmethyl-6,7-didehydro-4,5α-epoxy-3,14β-dihydroxy-1',7'-tetramethylene-6,7,2',3'-indolomorphinan, 17-(3-butenyl)-6,7-didehydro-4,5α-epoxy-3,14β-dihydroxy-1',7'-tetramethylene-6,7,2',3'-indolomorphinan, 17-phenethyl-6,7-didehydro-4,5α-epoxy-3,14β-dihydroxy-1',7'-tetramethylene-6,7,2',3'-indolomorphinan, 17-benzyl-6,7-didehydro-4,5α-epoxy-3,14β-dihydroxy-1',7'-tetramethylene-6,7,2',3'-indolomorphinan, 17-butyl-6,7-didehydro-4,5α-epoxy-3,14β-dihydroxy-1',7'-tetramethylene-6,7,2',3'-indolomorphinan, 17-(furan-2-ylmthyl)-6,7-didehydro-4,5α-epoxy-3,14β-dihydroxy-1',7'-tetramethylene-6,7,2',3'-indolomorphinan, 17-cinnamyl-6,7-didehydro-4,5α-epoxy-3,14β-dihydroxy-1',7'-tetramethylene-6,7,2',3'-indolomorphinan, 17-cyclohexylmethyl-6,7-didehydro-4,5α-epoxy-3,14β-dihydroxy-1',7'-tetramethylene-6,7,2',3'-indolomorphinan, 17-(thiophene-2-ylethyl)-6,7-didehydro-4,5α-epoxy-3,14β-dihydroxy-1',7'-tetramethylene-6,7,2',3'-indolomorphinan, 17-prenyl-6,7-didehydro-4,5α-epoxy-3,14β-dihydroxy-1',7'-tetramethylene-6,7,2',3'-indolomorphinan, 6,7-didehydro-4,5α-epoxy-3-hydroxy-14β-methoxy-1',7'-tetramethylene-6,7,2',3'-indolomorphinan, 17-methyl-6,7-didehydro-4,5α-epoxy-3-hydroxy-14β-methoxy-1',7'-tetramethylene-6,7,2',3'-indolomorphinan, 17-cyclobutylmethyl-6,7-didehydro-4,5α-epoxy-3-hydroxy-14β-methoxy-1',7'-tetramethylene-6,7,2',3'-indolomorphinan, 17-(3-butenyl)-6,7-didehydro-4,5-epoxy-3-hydroxy-14β-methoxy-1',7'-tetramethylene-6,7,2',3'-indolomorphinan, 17-phenethyl-6,7-didehydro-4,5α-epoxy-3-hydroxy-14β-methoxy-1',7'-tetramethylene-6,7,2',3'-indolomorphinan, 17-benzyl-6,7-didehydro-4,5α-epoxy-3-hydroxy-14β-methoxy-1',7'-tetramethylene-6,7,2',3'-indolomorphinan, 17-butyl-6,7-didehydro-4,5α-epoxy-3-hydroxy-14β-methoxy-1',7'-tetramethylene-6,7,2',3'-indolomorphinan, 17-(furan-2-ylmthyl)-6,7-didehydro-4,5α-epoxy-3-hydroxy-14β-methoxy-1',7'-tetramethylene-6,7,2',3'-indolomorphinan, 17-cinnamyl-6,7-didehydro-4,5α-epoxy-3-hydroxy-14β-methoxy-1',7'-tetramethylene-6,7,2',3'-indolomorphinan, 17-cyclohexylmethyl-6,7-didehydro-4,5α-epoxy-3-hydroxy-14β-methoxy-1',7'-tetramethylene-6,7,2',3'-indolomorphinan, 17-(thiophene-2-ylethyl)-6,7-didehydro-4,5α-epoxy- 3-hydroxy-14β-methoxy-1',7'-tetramethylene-6,7,2',3'-indolomorphinan, 17-prenyl-6,7-didehydro-4,5α-epoxy-3-hydroxy-14β-methoxy-1',7'-tetramethylene-6,7,2',3'-indolomorphinan, 6,7-didehydro-4,5α-epoxy-3-methoxy-14β-hydroxy-1',7'-tetramethylene-6,7,2',3-indolomorphinan, 17-methyl-6,7-didehydro-4,5α-epoxy-3-methoxy-14β-hydroxy-1',7'-tetramethylene-6,7,2',3'-indolomorphinan, 17-cyclobutylmethyl-6,7-didehydro-4,5α-epoxy-3-methoxy-14β-hydroxy-1',7'-tetramethylene-6,7,2',3'-indolomorphinan, 17-(3-butenyl)-6,7-didehydro-4,5α-epoxy-3-methoxy-14β-hydroxy-1',7'-tetramethylene-6,7,2',3'-indolomorphinan, 17-phenethyl-6,7-didehydro-4,5α-epoxy-3-methoxy-14β-hydroxy-1',7'-tetramethylene-6,7,2',3'-indolomorphinan, 17-benzyl-6,7-didehydro-4,5α-epoxy-3-methoxy-14β-hydroxy-1',7'-tetramethylene-6,7,2',3'-indolomorphinan, 17-butyl-6,7-didehydro-4,5α-epoxy-3-methoxy-14β-hydroxy-1',7'-tetramethylene-6,7,2',3'-indolomorphinan, 17-(furan-2-ylmthyl)-6,7-didehydro-4,5α-epoxy-3-methoxy-14β-hydroxy-1',7'-tetramethylene-6,7,2',3'-indolomorphinan, 17-cinnamyl-6,7-didehydro-4,5α-epoxy-3-methoxy-14β-hydroxy-1',7'-tetramethylene-6,7,2',3'-indolomorphinan, 17-cyclohexylmethyl-6,7-didehydro-4,5α-epoxy-3-methoxy-14β-hydroxy-1',7'-tetramethylene-6,7,2',3'-indolomorphinan, 17-(thiophene-2-ylethyl)-6,7-didehydro-4,5α-epoxy-3-methoxy-14β-hydroxy-1',7'-tetramethylene-6,7,2',3'-indolomorphinan, 17-prenyl-6,7-didehydro-4,5α-epoxy-3-methoxy-14β-hydroxy-1',7'-tetramethylene- 6,7,2',3'-indolomorphinan, 6,7-didehydro-4,5α-epoxy-3,14β-dimethoxy-1',7'-tetramethylene-6,7,2',3'-indolomorphinan, 17-methyl-6,7-didehydro-4,5α-epoxy-3,14β-dimethoxy-1',7'-tetramethylene-6,7,2',3'-indolomorphinan, 17-cyclobutylmethyl-6,7-didehydro-4,5α-epoxy-3,14β-dimethoxy-1',7'-tetramethylene-6,7,2',3'-indolomorphinan, 17-(3-butenyl)-6,7-didehydro-4,5α-epoxy-3,14β-dimethoxy-1',7'-tetramethylene-6,7,2',3'-indolomorphinan, 17-phenethyl-6,7-didehydro-4,5α-epoxy-3,14β-dimethoxy-1',7'-tetramethylene-6,7,2',3'-indolomorphinan, 17-benzyl-6,7-didehydro-4,5α-epoxy-3,14β-dimethoxy-1',7'-tetramethylene-6,7,2',3'-indolomorphinan, 17-butyl-6,7-didehydro-4,5α-epoxy-3, 14β-dimethoxy-1',7'-tetramethylene-6,7,2',3'-indolomorphinan, 17-(furan-2-ylmthyl)-6,7-didehydro-4,5α-epoxy-3,14β-dimethoxy-1',7'-tetramethylene-6,7,2',3'-indolomorphinan, 17-cinnamyl-6,7-didehydro-4,5α-epoxy-3,14β-dimethoxy-1',7'-tetramethylene-6,7,2',3'-indolomorphinan, 17-cyclohexylmethyl-6,7-didehydro-4,5α-epoxy-3,14β-dimethoxy-1',7'-tetramethylene-6,7,2',3'-indolomorphinan, 17-(thiophene-2-ylethyl)-6,7-didehydro-4,5α-epoxy-3,14β-dimethoxy-1',7'-tetramethylene-6,7,2',3'-indolomorphinan, 17-prenyl-6,7-didehydro-4,5α-epoxy-3,14β-dimethoxy-1',7'-tetramethylene-6,7,2',3'-indolomorphinan, 17-cyclopropylmethyl-6,7-didehydro-4,5α-epoxy-3,14β-dihydroxy-1',7'-ethylene-4'-trifluoromethyl-6,7,2',3'-indolomorphinan, 17-allyl-6,7-didehydro-4,5α-epoxy-3,14β-dihydroxy-1',7'-ethylene-4'-trifluoromethyl-6,7,2',3'-indolomorphinan, 17-cyclopropylmethyl-6,7-didehydro-4,5α-epoxy-3-hydroxy-14β-methoxy-1',7'-ethylene-4'-trifluoromethyl-6,7,2',3'-indolomorphinan, 17-allyl-6,7-didehydro-4,5α-epoxy-3-hydroxy-14β-methoxy-1',7'-ethylene-4'-trifluoromethyl-6,7,2',3'-indolomorphinan, 17-cyclopropylmethyl-6,7-didehydro-4,5α-epoxy-3-methoxy-14β-hydroxy-1',7'-ethylene-4'-trifluoromethyl-6,7,2',3'-indolomorphinan, 17-allyl-6,7-didehydro-4,5α-epoxy-3-methoxy-14β-hydroxy-1',7'-ethylene-4'-trifluoromethyl-6,7,2',3'-indolomorphinan, 17-cyclopropylmethyl-6,7-didehydro-4,5α-epoxy-3,14β-dimethoxy-1',7'-ethylene-4'-trifluoromethyl-6,7,2',3'-indolomorphinan, 17-allyl-6,7-didehydro-4,5α-epoxy-3,14β-dimethoxy-1',7'-ethylene-4'-trifluoromethyl-6,7,2',3'-indolomorphinan, 17-cyclopropylmethyl-6,7-didehydro-4,5α-epoxy-3,14β-dihydroxy-1',7'-ethylene-5'-trifluoromethyl-6,7,2',3'-indolomorphinan, 17-allyl-6,7-didehydro-4,5α-epoxy-3,14β-dihydroxy-1',7'-ethylene-5'-trifluoromethyl-6,7,2',3'-indolomorphinan, 17-cyclopropylmethyl-6,7-didehydro-4,5α-epoxy-3-hydroxy-14β-methoxy-1',7'-ethylene-5'-trifluoromethyl-6,7,2',3'-indolomorphinan, 17-allyl-6,7-didehydro-4,5α-epoxy-3-hydroxy-14β-methoxy-1',7'-ethylene-5'-trifluoromethyl-6,7,2',3'-indolomorphinan, 17-cyclopropylmethyl-6,7-didehydro-4,5α-epoxy-3-methoxy-14β-hydroxy-1',7'-ethylene- 5'-trifluoromethyl-6,7,2',3'-indolomorphinan, 17-allyl-6,7-didehydro-4,5α-epoxy-3-methoxy-14β-hydroxy-1',7'-ethylene-5'-trifluoromethyl-6,7,2',3'-indolomorphinan, 17-cyclopropylmethyl-6,7-didehydro-4,5α-epoxy-3,14β-dimethoxy-1',7'-ethylene-5'-trifluoromethyl-6,7,2',3'-indolomorphinan, 17-allyl-6,7-didehydro-4,5α-epoxy-3,14β-dimethoxy-1',7'-ethylene-5'-trifluoromethyl-6,7,2',3'-indolomorphinan, 17-cyclopropylmethyl-6,7-didehydro-4,5α-epoxy-3,14β-dihydroxy-1',7'-ethylene-6'-trifluoromethyl-6,7,2',3'-indolomorphinan, 17-allyl-6,7-didehydro-4,5α-epoxy-3,14β-dihydroxy-1',7'-ethylene-6'-trifluoromethyl-6,7,2',3'-indolomorphinan, 17-cyclopropylmethyl-6,7-didehydro-4,5α-epoxy-3-hydroxy-14β-methoxy-1',7'-ethylene-6'-trifluoromethyl-6,7,2',3'-indolomorphinan, 17-allyl-6,7-didehydro-4,5α-epoxy-3-hydroxy-14β-methoxy-1',7'-ethylene-6'-trifluoromethyl-6,7,2',3'-indolomorphinan, 17-cyclopropylmethyl-6,7-didehydro-4,5α-epoxy-3-methoxy-14β-hydroxy-1',7'-ethylene-6'-trifluoromethyl-6,7,2',3'-indolomorphinan, 17-allyl-6,7-didehydro-4,5α-epoxy-3-methoxy-14β-hydroxy-1',7'-ethylene-6'-trifluoromethyl-6,7,2',3'-indolomorphinan, 17-cyclopropylmethyl-6,7-didehydro-4,5α-epoxy-3,14β-dimethoxy-1',7'-ethylene-6'-trifluoromethyl-6,7,2',3'-indolomorphinan, 17-allyl-6,7-didehydro-4,5α-epoxy-3,14β-dimethoxy-1',7'-ethylene-6'-trifluoromethyl-6,7,2',3'-indolomorphinan, 17-cyclopropylmethyl-6,7-didehydro-4,5α-epoxy- 3,14β-dihydroxy-1',7'-trimethylene-4'-trifluoromethyl-6,7,2',3'-indolomorphinan, 17-allyl-6,7-didehydro-4,5α-epoxy-3,14β-dihydroxy-1',7'-trimethylene-4'-trifluoromethyl-6,7,2',3'-indolomorphinan, 17-cyclopropylmethyl-6,7-didehydro-4,5α-epoxy-3-hydroxy-14β-methoxy-1',7'-trimethylene-4'-trifluoromethyl-6,7,2',3'-indolomorphinan, 17-allyl-6,7-didehydro-4,5α-epoxy-3-hydroxy-14β-methoxy-1',7'-trimethylene-4'-trifluoromethyl-6,7,2',3'-indolomorphinan, 17-cyclopropylmethyl-6,7-didehydro-4,5α-epoxy-3-methoxy-14β-hydroxy-1',7'-trimethylene-4'-trifluoromethyl-6,7,2',3'-indolomorphinan, 17-allyl-6,7-didehydro-4,5α-epoxy-3-methoxy-14β-hydroxy-1',7'-trimethylene-4'-trifluoromethyl-6,7,2',3'-indolomorphinan, 17-cyclopropylmethyl-6,7-didehydro-4,5α-epoxy-3,14β-dimethoxy-1',7'-trimethylene-4'-trifluoromethyl-6,7,2',3'-indolomorphinan, 17-allyl-6,7-didehydro-4,5α-epoxy-3,14β-dimethoxy-1',7'-trimethylene-4'-trifluoromethyl-6,7,2',3'-indolomorphinan, 17-cyclopropylmethyl-6,7-didehydro-4,5α-epoxy-3,14β-dihydroxy-1',7'-trimethylene-5'-trifluoromethyl-6,7,2',3'-indolomorphinan, 17-allyl-6,7-didehydro-4,5α-epoxy-3,14β-dihydroxy-1',7'-trimethylene-5'-trifluoromethyl-6,7,2',3'-indolomorphinan, 17-cyclopropylmethyl-6,7-didehydro-4,5α-epoxy-3-hydroxy-14β-methoxy-1',7'-trimethylene-5'-trifluoromethyl-6,7,2',3'-indolomorphinan, 17-allyl-6,7-didehydro-4,5α-epoxy-3-hydroxy-14β-methoxy-1',7'-trimethylene-5'-trifluoromethyl- 6,7,2',3'-indolomorphinan, 17-cyclopropylmethyl-6,7-didehydro-4,5α-epoxy-3-methoxy-14β-hydroxy-1',7'-trimethylene-5'-trifluoromethyl-6,7,2',3'-indolomorphinan, 17-allyl-6,7-didehydro-4,5α-epoxy-3-methoxy-14β-hydroxy-1',7'-trimethylene-5'-trifluoromethyl-6,7,2',3'-indolomorphinan, 17-cyclopropylmethyl-6,7-didehydro-4,5α-epoxy-3,14β-dimethoxy-1',7'-trimethylene-5'-trifluoromethyl-6,7,2',3'-indolomorphinan, 17-allyl-6,7-didehydro-4,5α-epoxy-3,14β-dimethoxy-1',7'-trimethylene-5'-trifluoromethyl-6,7,2',3'-indolomorphinan, 17-cyclopropylmethyl-6,7-didehydro-4,5α-epoxy-3,14β-dihydroxy-1',7'-trimethylene-6'-trifluoromethyl-6,7,2',3'-indolomorphinan, 17-allyl-6,7-didehydro-4,5α-epoxy-3,14β-dihydroxy-1',7'-trimethylene-6'-trifluoromethyl-6,7,2',3'-indolomorphinan, 17-cyclopropylmethyl-6,7-didehydro-4,5α-epoxy-3-hydroxy-14β-methoxy-1',7'-trimethylene-6'-trifluoromethyl-6,7,2',3'-indolomorphinan, 17-allyl-6,7-didehydro-4,5α-epoxy-3-hydroxy-14β-methoxy-1',7'-trimethylene-6'-trifluoromethyl-6,7,2',3'-indolomorphinan, 17-cyclopropylmethyl-6,7-didehydro-4,5α-epoxy-3-methoxy-14β-hydroxy-1',7'-trimethylene-6'-trifluoromethyl-6,7,2',3'-indolomorphinan, 17-allyl-6,7-didehydro-4,5α-epoxy-3-methoxy-14β-hydroxy-1',7'-trimethylene-6'-trifluoromethyl-6,7,2',3'-indolomorphinan, 17-cyclopropylmethyl-6,7-didehydro-4,5α-epoxy-3,14β-dimethoxy-1',7'-trimethylene-6'-trifluoromethyl- 6,7,2',3'-indolomorphinan, 17-allyl-6,7-didehydro-4,5α-epoxy-3,14β-dimethoxy-1',7'-trimethylene-6'-trifluoromethyl-6,7,2',3'-indolomorphinan, 17-cyclopropylmethyl-6,7-didehydro-4,5α-epoxy-3,14β-dihydroxy-1',7'-tetramethylene-4'-trifluoromethyl-6,7,2',3'-indolomorphinan, 17-allyl-6,7-didehydro-4,5α-epoxy-3,14β-dihydroxy-1',7'-tetramethylene-4'-trifluoromethyl-6,7,2',3'-indolomorphinan, 17-cyclopropylmethyl-6,7-didehydro-4,5α-epoxy-3-hydroxy-14β-methoxy-1',7'-tetramethylene-4'-trifluoromethyl-6,7,2',3'-indolomorphinan, 17-allyl-6,7-didehydro-4,5α-epoxy-3-hydroxy-14β-methoxy-1',7'-tetramethylene-4'-trifluoromethyl-6,7,2',3'-indolomorphinan, 17-cyclopropylmethyl-6,7-didehydro-4, 5α-epoxy-3-methoxy-14β-hydroxy-1',7'-tetramethylene-4'-trifluoromethyl-6,7,2',3'-indolomorphinan, 17-allyl-6,7-didehydro-4,5α-epoxy-3-methoxy-14β-hydroxy-1',7'-tetramethylene-4'-trifluoromethyl-6,7,2',3'-indolomorphinan, 17-cyclopropylmethyl-6,7-didehydro-4,5α-epoxy-3,14β-dimethoxy-1',7'-tetramethylene-4'-trifluoromethyl-6,7,2',3'-indolomorphinan, 17-allyl-6,7-didehydro-4,5α-epoxy-3,14β-dimethoxy-1',7'-tetramethylene-4'-trifluoromethyl-6,7,2',3'-indolomorphinan, 17-cyclopropylmethyl-6,7-didehydro-4,5α-epoxy-3,14β-dihydroxy-1',7'-tetramethylene-5'-trifluoromethyl-6,7,2',3'-indolomorphinan, 17-allyl-6,7-didehydro-4,5α-epoxy-3,14β-dihydroxy-1',7'-tetramethylene-5'-trifluoromethyl- 6,7,2',3'-indolomorphinan, 17-cyclopropylmethyl-6,7-didehydro-4,5α-epoxy-3-hydroxy-14β-methoxy-1',7'-tetramethylene-5'-trifluoromethyl-6,7,2',3'-indolomorphinan, 17-allyl-6,7-didehydro-4,5α-epoxy-3-hydroxy-14β-methoxy-1',7'-tetramethylene-5'-trifluoromethyl-6,7,2',3'-indolomorphinan, 17-cyclopropylmethyl-6,7-didehydro-4,5α-epoxy-3-methoxy-14β-hydroxy-1',7'-tetramethylene-5'-trifluoromethyl-6,7,2',3'-indolomorphinan, 17-allyl-6,7-didehydro-4,5α-epoxy-3-methoxy-14β-hydroxy-1',7'-tetramethylene-5'-trifluoromethyl-6,7,2',3'-indolomorphinan, 17-cyclopropylmethyl-6,7-didehydro-4,5α-epoxy-3,14β-dimethoxy-1',7'-tetramethylene-5'-trifluoromethyl-6,7,2',3'-indolomorphinan, 17-allyl-6,7-didehydro-4,5α-epoxy-3,14β-dimethoxy-1',7'-tetramethylene-5'-trifluoromethyl-6,7,2',3'-indolomorphinan, 17-cyclopropylmethyl-6,7-didehydro-4,5α-epoxy-3,14β-dihydroxy-1',7'-tetramethylene-6'-trifluoromethyl-6,7,2',3'-indolomorphinan, 17-allyl-6,7-didehydro-4,5α-epoxy-3,14'-dihydroxy-1',7'-tetramethylene-6'-trifluoromethyl-6,7,2',3'-indolomorphinan, 17-cyclopropylmethyl-6,7-didehydro-4,5α-epoxy-3-hydroxy-14β-methoxy-1',7'-tetramethylene-6'-trifluoromethyl-6,7,2',3'-indolomorphinan, 17-allyl-6,7-didehydro-4,5α-epoxy-3-hydroxy-14β-methoxy-1',7'-tetramethylene-6'-trifluoromethyl-6,7,2',3'-indolomorphinan, 17-cyclopropylmethyl-6,7-didehydro-4,5α-epoxy-3-methoxy-14β-hydroxy-1',7'-tetramethylene-6'-trifluoromethyl- 6,7,2',3'-indolomorphinan, 17-allyl-6,7-didehydro-4,5α-epoxy-3-methoxy-14β-hydroxy-1',7'-tetramethylene-6'-trifluoromethyl-6,7,2',3'-indolomorphinan, 17-cyclopropylmethyl-6,7-didehydro-4,5α-epoxy-3,14β-dimethoxy-1',7'-tetramethylene-6'-trifluoromethyl-6,7,2',3'-indolomorphinan, 17-allyl-6,7-didehydro-4,5α-epoxy-3,14β-dimethoxy-1',7'-tetramethylene-6'-trifluoromethyl-6,7,2',3'-indolomorphinan, 17-cyclopropylmethyl-6,7-didehydro-4,5α-epoxy-3,14β-dihydroxy-7',1'-epoxyethano-6,7,2',3'-indolomorphinan, 17-allyl-6,7-didehydro-4,5α-epoxy-3,14β-dihydroxy-7',1'-epoxyethano-6,7,2',3'-indolomorphinan, 17-(3-butenyl)-6,7-didehydro-4,5α-epoxy-3,14β-dihydroxy-7',1'-epoxyethano-6,7,2',3'-indolomorphinan, 17-phenethyl-6,7-didehydro-4,5α-epoxy-3,14β-dihydroxy-7',1'-epoxyethano-6,7,2',3'-indolomorphinan, 17-cyclobutylmethyl-6,7-didehydro-4,5α-epoxy-3,14β-dihydroxy-7',1'-epoxyethano-6,7,2',3'-indolomorphinan, 17-methyl-6,7-didehydro-4,5α-epoxy-3,14β-dihydroxy-7',1'-epoxyethano-6,7,2',3'-indolomorphinan, 17-cyclopropylmethyl-6,7-didehydro-4,5α-epoxy-3-hydroxy-14β-methoxy-7',1'-epoxyethano-6,7,2',3'-indolomorphinan, 17-allyl-6,7-didehydro-4,5α-epoxy-3-hydroxy-14β-methoxy-7',1'-epoxyethano-6,7,2',3'-indolomorphinan, 17-(3-butenyl)-6,7-didehydro-4,5α-epoxy-3-hydroxy-14β-methoxy-7',1'-epoxyethano-6,7,2',3'-indolomorphinan, 17-phenethyl-6,7-didehydro-4,5α-epoxy-3-hydroxy- 14β-methoxy-7',1'-epoxyethano-6,7,2',3'-indolomorphinan, 17-cyclobutylmethyl-6,7-didehydro-4,5α-epoxy-3-hydroxy-14β-methoxy-7',1'-epoxyethano-6,7,2',3'-indolomorphinan, 17-methyl-6,7-didehydro-4,5α-epoxy-3-hydroxy-14β-methoxy-7',1'-epoxyethano-6,7,2',3'-indolomorphinan, 17-cyclopropylmethyl-6,7-didehydro-4,5α-epoxy-3-methoxy-14β-hydroxy-7',1'-epoxyethano-6,7,2',3'-indolomorphinan, 17-allyl-6,7-didehydro-4,5α-epoxy-3-methoxy-14β-hydroxy-7',1'-epoxyethano-6,7,2',3'-indolomorphinan, 17-(3-butenyl)-6,7-didehydro-4,5α-epoxy-3-methoxy-14β-hydroxy-7',1'-epoxyethano-6,7,2',3'-indolomorphinan, 17-phenethyl-6,7-didehydro-4,5α-epoxy-3-methoxy-14β-hydroxy-7',1'-epoxyethano-6,7,2',3'-indolomorphinan, 17-cyclobutylmethyl-6,7-didehydro-4,5α-epoxy-3-methoxy-14β-hydroxy-7',1'-epoxyethano-6,7,2',3'-indolomorphinan, 17-methyl-6,7-didehydro-4,5α-epoxy-3-methoxy-14β-hydroxy-7',1'-epoxyethano-6,7,2',3'-indolomorphinan, 17-cyclopropylmethyl-6,7-didehydro-4,5α-epoxy-3,14β-dimethoxy-7',1'-epoxyethano-6,7,2',3'-indolomorphinan, 17-allyl-6,7-didehydro-4,5α-epoxy-3,14β-dimethoxy-7',1'-epoxyethano-6,7,2',3'-indolomorphinan, 17-(3-butenyl)-6,7-didehydro-4,5α-epoxy-3,14β-dimethoxy-7',1'-epoxyethano-6,7,2',3'-indolomorphinan, 17-phenethyl-6,7-didehydro-4,5α-epoxy-3,14β-dimethoxy-7',1'-epoxyethano-6,7,2',3'-indolomorphinan, 17-cyclobutylmethyl-6,7-didehydro-4,5α-epoxy-3,14β-dimethoxy-7',1'-epoxyethano-6,7,2',3'-indolomorphinan, 17-methyl-6,7-didehydro-4,5α-epoxy-3,14β-dimethoxy-7',1'-epoxyethano-6,7,2',3'-indolomorphinan, 17-cyclopropylmethyl-6,7-didehydro-4,5α-epoxy-3,14βdihydroxy-7',1'-epithioethano-6,7,2',3'-indolomorphinan, 17-allyl-6,7-didehydro-4,5α-epoxy-3,14β-dihydroxy-7',1'-epithioethano-6,7,2',3'-indolomorphinan, 17-(3-butenyl)-6,7-didehydro-4,5α-epoxy-3,14β-dihydroxy-7',1'-epithioethano-6,7,2',3'-indolomorphinan, 17-phenethyl-6,7-didehydro-4,5α-epoxy-3,14β-dihydroxy-7',1'-epithioethano-6,7,2',3'-indolomorphinan, 17-cyclobutylmethyl-6,7-didehydro-4,5α-epoxy-3,14β-dihydroxy-7',1'-epithioethano-6,7,2',3'-indolomorphinan, 17-methyl-6,7-didehydro-4,5α-epoxy-3,14β-dihydroxy-7',1'-epithioethano-6,7,2',3'-indolomorphinan, 17-cyclopropylmethyl-6,7-didehydro-4,5α-epoxy-3-hydroxy-14β-methoxy-7',1'-epithioethano-6,7,2',3'-indolomorphinan, 17-allyl-6,7-didehydro-4,5α-epoxy-3-hydroxy-14β-methoxy-7',1'-epithioethano-6,7,2',3'-indolomorphinan, 17-(3-butenyl)-6,7-didehydro-4,5α-epoxy-3-hydroxy-14β-methoxy-7',1'-epithioethano-6,7,2',3'-indolomorphinan, 17-phenethyl-6,7-didehydro-4,5α-epoxy-3-hydroxy-14β-methoxy-7',1'-epithioethano-6,7,2',3'-indolomorphinan, 17-cyclobutylmethyl-6,7-didehydro-4,5α-epoxy-3-hydroxy-14β-methoxy-7',1'-epithioethano-6,7,2',3'-indolomorphinan, 17-methyl-6,7-didehydro-4,5α-epoxy-3-hydroxy-14β-methoxy-7',1'-epithioethano-6,7,2',3'-indolomorphinan, 17-cyclopropylmethyl-6,7-didehydro-4,5α-epoxy-3-methoxy-14β-hydroxy-7',1'-epithioethano-6,7,2',3'-indolomorphinan, 17-allyl-6,7-didehydro-4,5α-epoxy-3-methoxy-14β-hydroxy-7',1'-epithioethano-6,7,2',3'-indolomorphinan, 17-(3-butenyl)-6,7-didehydro-4,5α-epoxy-3-methoxy-14β-hydroxy-7',1'-epithioethano-6,7,2',3'-indolomorphinan, 17-phenethyl-6,7-didehydro-4,5α-epoxy-3-methoxy-14β-hydroxy-7',1'-epithioethano-6,7,2',3'-indolomorphinan, 17-cyclobutylmethyl-6,7-didehydro-4,5α-epoxy-3-methoxy-14β-hydroxy-7',1'-epithioethano-6,7,2',3'-indolomorphinan, 17-methyl-6,7-didehydro-4,5α-epoxy-3-methoxy-14β-hydroxy-7',1'-epithioethano-6,7,2',3'-indolomorphinan, 17-cyclopropylmethyl-6,7-didehydro- 4,5α-epoxy-3,14β-dimethoxy-7',1'-epithioethano-6,7,2',3'-indolomorphinan, 17-allyl-6,7-didehydro-4,5α-epoxy-3,14β-dimethoxy-7',1'-epithioethano-6,7,2',3'-indolomorphinan, 17-(3-butenyl)-6,7-didehydro-4,5α-epoxy-3,14β-dimethoxy-7',1'-epithioethano-6,7,2',3'-indolomorphinan, 17-phenethyl-6,7-didehydro-4,5α-epoxy-3,14β-dimethoxy-7',1'-epithioethano-6,7,2',3'-indolomorphinan, 17-cyclobutylmethyl-6,7-didehydro-4,5α-epoxy-3,14β-dimethoxy-7',1'-epithioethano-6,7,2',3'-indolomorphinan, 17-methyl-6,7-didehydro-4,5α-epoxy-3,14β-dimethoxy-7',1'-epithioethano-6,7,2',3'-indolomorphinan, 17-cyclopropylmethyl-6,7-didehydro-4,5α-epoxy-3,14β-dihydroxy-1',7'-(1,1-dimethylpropano)-6,7,2',3'-indolomorphinan, 17-allyl-6,7-didehydro-4,5α-epoxy-3,14β-dihydroxy-1',7'-(1,1-dimethylpropano)-6,7,2',3'-indolomorphinan, 17-(3-butenyl)-6,7-didehydro-4,5α-epoxy-3,14β-dihydroxy-1',7'-(1,1-dimethylpropano)-6,7,2',3'-indolomorphinan, 17-phenethyl-6,7-didehydro-4,5α-epoxy-3,14β-dihydroxy-1',7'-(1,1-dimethylpropano)-6,7,2',3'-indolomorphinan, 17-cyclobutylmethyl-6,7-didehydro-4,5α-epoxy-3,14β-dihydroxy-1',7'-(1,1-dimethylpropano)-6,7,2',3'-indolomorphinan, 17-methyl-6,7-didehydro-4,5α-epoxy-3,14β-dihydroxy-1',7'-(1,1-dimethylpropano)-6,7,2',3'-indolomorphinan, 17-cyclopropylmethyl-6,7-didehydro-4,5α-epoxy-3-hydroxy-14β-methoxy-1',7'-(1,1-dimethylpropano)-6,7,2',3'-indolomorphinan, 17-allyl-6,7-didehydro-4,5α-epoxy-3-hydroxy-14β-methoxy-1',7'-(1,1-dimethylpropano)-6,7,2',3'-indolomorphinan, 17-(3-butenyl)-6,7-didehydro-4,5α-epoxy-3-hydroxy-14β-methoxy-1',7'-(1,1-dimethylpropano)-6,7,2',3'-indolomorphinan, 17-phenethyl-6,7-didehydro-4,5α-epoxy-3-hydroxy-14β-methoxy-1',7'-(1,1-dimethylpropano)-6,7,2',3'-indolomorphinan, 17-cyclobutylmethyl-6,7-didehydro-4,5α-epoxy-3-hydroxy-14β-methoxy-1',7'-(1,1-dimethylpropano)-6,7,2',3'-indolomorphinan, 17-methyl-6,7-didehydro-4,5α-epoxy-3-hydroxy-14β-methoxy-1',7'-(1,1-dimethylpropano)-6,7,2',3'-indolomorphinan, 17-cyclopropylmethyl-6,7-didehydro-4,5α-epoxy-3-methoxy-14β-hydroxy-1',7'-(1,1-dimethylpropano)-6,7,2',3'-indolomorphinan, 17-allyl-6,7-didehydro-4,5α-epoxy-3-methoxy-14β-hydroxy-1',7'-(1,1-dimethylpropano)-6,7,2',3'-indolomorphinan, 17-(3-butenyl)-6,7-didehydro-4,5α-epoxy-3-methoxy-14β-hydroxy-1',7'-(1,1-dimethylpropano)-6,7,2',3'-indolomorphinan, 17-phenethyl-6,7-didehydro-4,5α-epoxy-3-methoxy-14β-hydroxy-1',7'-(1,1-dimethylpropano)-6,7,2',3'-indolomorphinan, 17-cyclobutylmethyl-6,7-didehydro-4,5α-epoxy-3-methoxy-14β-hydroxy-1',7'-(1,1-dimethylpropano)-6,7,2',3'-indolomorphinan, 17-methyl-6,7-didehydro-4,5α-epoxy-3-methoxy-14β-hydroxy-1',7'-(1,1-dimethylpropano)-6,7,2',3'-indolomorphinan, 17-cyclopropylmethyl-6,7-didehydro-4,5α-epoxy-3,14β-dimethoxy-1',7'-(1,1-dimethylpropano)-6,7,2',3'-indolomorphinan, 17-allyl-6,7-didehydro-4,5α-epoxy-3,14β-dimethoxy-1',7'-(1,1-dimethylpropano)-6,7,2',3'-indolomorphinan, 17-(3-butenyl)-6,7-didehydro-4,5α-epoxy-3,14β-dimethoxy-1',7'-(1,1-dimethylpropano)-6,7,2',3'-indolomorphinan, 17-phenethyl-6,7-didehydro-4,5α-epoxy-3,14β-dimethoxy-1',7'-(1,1-dimethylpropano)-6,7,2',3'-indolomorphinan, 17-cyclobutylmethyl-6,7-didehydro-4,5α-epoxy-3,14β-dimethoxy-1',7'-(1,1-dimethylpropano)-6,7,2',3'-indolomorphinan, 17-methyl-6,7-didehydro-4,5α-epoxy-3,14β-dimethoxy-1',7'-(1,1-dimethylpropano)-6,7,2',3'-indolomorphinan, 17-cyclopropylmethyl-6,7-didehydro-4,5α-epoxy-3,14β-dihydroxy-1',7'-(2,2-dimethylpropano)-6,7,2',3'-indolomorphinan, 17-allyl-6,7-didehydro-4,5α-epoxy-3,14β-dihydroxy-1',7'-(2,2-dimethylpropano)-6,7,2',3'-indolomorphinan, 17-(3-butenyl)-6,7-didehydro-4,5α-epoxy-3,14β-dihydroxy-1',7'-(2,2-dimethylpropano)-6,7,2',3'-indolomorphinan, 17-phenethyl-6,7-didehydro-4,5α-epoxy-3,14β-dihydroxy-1',7'-(2,2-dimethylpropano)-6,7,2',3'-indolomorphinan, 17-cyclobutylmethyl-6,7-didehydro-4,5α-epoxy-3,14β-dihydroxy-1',7'-(2,2-dimethylpropano)-6,7,2',3'-indolomorphinan, 17-methyl-6,7-didehydro-4,5α-epoxy-3,14β-dihydroxy-1',7'-(2,2-dimethylpropano)-6,7,2',3'-indolomorphinan, 17-cyclopropylmethyl-6,7-didehydro-4,5α-epoxy-3-hydroxy-14β-methoxy-1',7'-(2,2-dimethylpropano)-6,7,2',3'-indolomorphinan, 17-allyl-6,7-didehydro-4,5α-epoxy-3-hydroxy-14β-methoxy-1',7'-(2,2-dimethylpropano)-6,7,2',3'-indolomorphinan, 17-(3-butenyl)-6,7-didehydro-4,5α-epoxy-3-hydroxy-14β-methoxy-1',7'-(2,2-dimethylpropano)-6,7,2',3'-indolomorphinan, 17-phenethyl-6,7-didehydro-4,5α-epoxy-3-hydroxy-14β-methoxy-1',7'-(2,2-dimethylpropano)-6,7,2',3'-indolomorphinan, 17-cyclobutylmethyl-6,7-didehydro-4,5α-epoxy-3-hydroxy-14β-methoxy-1',7'-(2,2-dimethylpropano)-6,7,2',3'-indolomorphinan, 17-methyl-6,7-didehydro-4,5α-epoxy-3-hydroxy-14β-methoxy-1',7'-(2,2-dimethylpropano)-6,7,2',3'-indolomorphinan, 17-cyclopropylmethyl-6,7-didehydro-4,5α-epoxy-3-methoxy-14β-hydroxy-1',7'-(2,2-dimethylpropano)-6,7,2',3'-indolomorphinan, 17-allyl-6,7-didehydro-4,5α-epoxy-3-methoxy-14β-hydroxy-1',7'-(2,2-dimethylpropano)-6,7,2',3'-indolomorphinan, 17-(3-butenyl)-6,7-didehydro-4,5α-epoxy-3-methoxy-14β-hydroxy-1',7'-(2,2-dimethylpropano)-6,7,2',3'-indolomorphinan, 17-phenethyl-6,7-didehydro-4,5α-epoxy-3-methoxy-14β-hydroxy-1',7'-(2,2-dimethylpropano)-6,7,2',3'-indolomorphinan, 17-cyclobutylmethyl-6,7-didehydro-4,5α-epoxy-3-methoxy-14β-hydroxy-1',7'-(2,2-dimethylpropano)-6,7,2',3'-indolomorphinan, 17-methyl-6,7-didehydro-4,5α-epoxy-3-methoxy-14β-hydroxy-1',7'-(2,2-dimethylpropano)-6,7,2',3'-indolomorphinan, 17-cyclopropylmethyl-6,7-didehydro-4,5α-epoxy-3,14β-dimethoxy-1',7'-(2,2-dimethylpropano)-6,7,2',3'-indolomorphinan, 17-allyl-6,7-didehydro-4,5α-epoxy-3,14β-dimethoxy-1',7'-(2,2-dimethylpropano)-6,7,2',3'-indolomorphinan, 17-(3-butenyl)-6,7-didehydro-4,5α-epoxy-3,14β-dimethoxy-1',7'-(2,2-dimethylpropano)-6,7,2',3'-indolomorphinan, 17-phenethyl-6,7-didehydro-4,5α-epoxy-3,14β-dimethoxy-1',7'-(2,2-dimethylpropano)-6,7,2',3'-indolomorphinan, 17-cyclobutylmethyl-6,7-didehydro-4,5α-epoxy-3,14β-dimethoxy-1',7'-(2,2-dimethylpropano)-6,7,2',3'-indolomorphinan, 17-methyl-6,7-didehydro-4,5α-epoxy-3,14'-dimethoxy-1',7'-(2,2-dimethylpropano)-6,7,2',3'-indolomorphinan.

And the compound wherein R4 and R5 together form the benzene ring, that is, compound 2 of the formula:

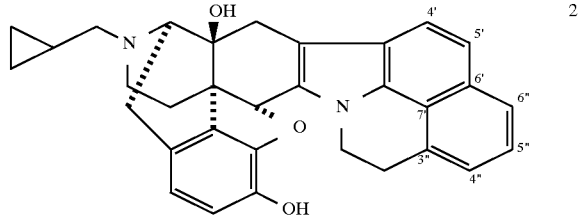

which is named according to former nomenclature 17-cyclopropylmethyl-6,7-didehydro-4,5-α-epoxy-3,14β-dihydroxy-1',3"-ethylene-6',7'-benzo-6,7,2',3'-indolomorphinan, is included in the present invention. So specific examples of the compounds employed in the present invention include 17-allyl-6,7-didehydro-4,5α-epoxy-3,14β-dihydroxy-1',3"-ethylene-6',7'-benzo-6,7,2',3'-indolomorphinan, 17-cyclopropylmethyl-6,7-didehydro-4,5α-epoxy-3-hydroxy-14β-methoxy-1',3"-ethylene-6',7'- benzo-6,7,2',3'-indolomorphinan, 17-allyl-6,7-didehydro-4,5α-epoxy-3-hydroxy-14β-methoxy-1',3"-ethylene-6',7'-benzo-6,7,2',3'-indolomorphinan, 17-cyclopropylmethyl-6,7-didehydro-4,5α-epoxy-3-methoxy-14β-hydroxy-1',3"-ethylene-6',7'-benzo-6,7,2',3'-indolomorphinan, 17-allyl-6,7-didehydro-4,5α-epoxy-3-methoxy-14β-hydroxy-1',3"-ethylene-6',7'-benzo-6,7,2',3 '-indolomorphinan, 17-cyclopropylmethyl-6,7-didehydro-4,5α-epoxy-3,14β-dihydoroxy-1',3"-ethylene-6',7'-benzo-6,7,2',3'-indolomorphinan, 17-allyl-6,7-didehydro-4,5α-epoxy-3,14β-dihydroxy-1',3"-ethylene-6',7'-benzo-6,7,2',3'-indolomorphinan, 17-cyclopropylmethyl-6,7-didehydro-4,5α-epoxy-3,14β-dihydroxy-1',3"-ethylene-5'-fluoro- 6',7'-benzo-6,7,2',3'-indolomorphinan, 17-allyl-6,7-didehydro-4,5α-epoxy-3,14β-dihydroxy-1',3"-ethylene-5'-fluoro-6',7'-benzo-6,7,2',3'-indolomorphinan, 17-cyclopropylmethyl-6,7-didehydro-4,5α-epoxy-3-hydroxy-14β-methoxy-1',3"-ethylene-5'-fluoro-6',7'-benzo-6,7,2',3'-indolomorphinan, 17-allyl-6,7-didehydro-4,5α-epoxy-3-hydroxy-14β-methoxy-1',3"-ethylene-5'-fluoro-6',7'-benzo-6,7,2',3'-indolomorphinan, 17-cyclopropylmethyl-6,7-didehydro-4,5α-epoxy-3-methoxy-14β-hydroxy-1',3"-ethylene-5'-fluoro-6',7'-benzo-6,7,2',3'-indolomorphinan, 17-allyl-6,7-didehydro-4,5α-epoxy-3-methoxy-14β-hydroxy-1',3"-ethylene-5'-fluoro-6',7'-benzo-6,7,2',3'-indolomorphinan, 17-cyclopropylmethyl-6,7-didehydro-4,5α-epoxy-3,14β-dihydroxy-1',3"-ethylene-5'-fluoro-6',7'-benzo-6,7,2',3'-indolomorphinan, 17-allyl-6,7-didehydro-4,5α-epoxy-3,14β-dihydoroxy-1',3"-ethylene-5'-fluoro-6',7'-benzo-6,7,2',3'-indolomorphinan, 17-cyclopropylmethyl-6,7-didehydro-4,5α-epoxy-3,14β-dihydroxy-1',3"-ethylene-5'-chloro-6',7'-benzo-6,7,2',3'-indolomorphinan, 17-allyl-6,7-didehydro-4,5α-epoxy-3,14β-dihydroxy-1',3"-ethylene-5'-chloro-6',7'-benzo-6,7,2',3'-indolomorphinan, 17-cyclopropylmethyl-6,7-didehydro-4,5α-epoxy-3-hydroxy-14β-methoxy-1',3"-ethylene-5'-chloro-61,7'-benzo-6,7,2',3'-indolomorphinan, 17-allyl-6,7-didehydro-4,5α-epoxy-3-hydroxy-14β-methoxy-1',3"-ethylene-5'-chloro-61,7'-benzo-6,7,2',3'-indolomorphinan, 17-cyclopropylmethyl-6,7-didehydro-4,5α-epoxy-3-methoxy- 14β-hydroxy-1',3"-ethylene-5'-chloro-6',7'-benzo-6,7,2',3'-indolomorphinan, 17-allyl-6,7-didehydro-4,5α-epoxy-3-methoxy-14β-hydroxy-1',3"-ethylene-5'-chloro-6',7'-benzo-6,7,2',3'-indolomorphinan, 17-cyclopropylmethyl-6,7-didehydro-4,5α-epoxy-3,14β-dihydroxy-1',3"-ethylene-5'-chloro-6',7'-benzo-6,7,2',3'-indolomorphinan, 17-allyl-6,7-didehydro-4,5α-epoxy-3,14β-dihydroxy-1',3"-ethylene-5'-chloro-6',7'-benzo-6,7,2',3'-indolomorphinan, 17-cyclopropylmethyl-6,7-didehydro-4,5α-epoxy-3,14β-dihydroxy-1',3"-ethylene-5'-bromo-6',7'-benzo-6,7,2',3'-indolomorphinan, 17-allyl-6,7-didehydro-4,5α-epoxy-3,14β-dihydroxy-1',3"-ethylene-5'-bromo-6',7'-benzo-6,7,2',3'-indolomorphinan, 17-cyclopropylmethyl-6,7-didehydro-4,5α-epoxy-3-hydroxy-14β-methoxy-1',3"-ethylene-5'-bromo-6',7'-benzo-6,7,2',3'-indolomorphinan, 17-allyl-6,7-didehydro-4,5α-epoxy-3-hydroxy-14β-methoxy-1',3"-ethylene-5'-bromo-6',7'-benzo-6,7,2',3'-indolomorphinan, 17-cyclopropylmethyl-6,7-didehydro-4,5α-epoxy-3-methoxy-14β-hydroxy-1',3"-ethylene-5'-bromo-6',7'-benzo-6,7,2',3'-indolomorphinan, 17-allyl-6,7-didehydro-4,5α-epoxy-3-methoxy-14β-hydroxy-1',3"-ethylene-5'-bromo-6',7'-benzo-6,7,2',3'-indolomorphinan, 17-cyclopropylmethyl-6,7-didehydro-4,5α-epoxy-3,14β-dihydroxy-1',3"-ethylene-5'-bromo-6',7'-benzo-6,7,2',3'-indolomorphinan, 17-allyl-6,7-didehydro-4,5α-epoxy-3,14β-dihydroxy-1',3"-ethylene-5'-bromo-6',7'-benzo-6,7,2',3'-indolomorphinan, 17-cyclopropylmethyl-6,7-didehydro-4,5α-epoxy-3,14β-dihydroxy-1',3"-ethylene-5'-methyl-6',7'-benzo-6,7,2',3'-indolomorphinan, 17-allyl-6,7-didehydro-4,5α-epoxy-3,14β-dihydroxy-1',3"-ethylene-5'-methyl-6',7'-benzo-6,7,2',3'-indolomorphinan, 17-cyclopropylmethyl-6,7-didehydro-4,5α-epoxy-3-hydroxy-14β-methoxy-1',3"-ethylene-5'-methyl-6',7'-benzo-6,7,2,3'-indolomorphinan, 17-allyl-6,7-didehydro-4,5α-epoxy-3-hydroxy-14β-methoxy-1',3"-ethylene-5'-methyl-6',7'-benzo-6,7,2',3'-indolomorphinan, 17-cyclopropylmethyl-6,7-didehydro-4,5α-epoxy-3-methoxy-14β-hydroxy-1',3"-ethylene-5'-methyl-6',7'-benzo-6,7,2',3'-indolomorphinan, 17-allyl-6,7-didehydro-4,5α-epoxy-3-methoxy-14β-hydroxy-1',3"-ethylene-5'-methyl-6',7'-benzo-6,7,2',3'-indolomorphinan, 17-cyclopropylmethyl-6,7-didehydro-4,5α-epoxy-3,14β-dihydroxy-1',13"-ethylene-5'-methyl-6',7'-benzo-6,7,2',3'-indolomorphinan, 17-allyl-6,7-didehydro-4,5α-epoxy-3,14β-dihydoroxy-1',3"-ethylene-5'-methyl-6',7'-benzo-6,7,2',3'-indolomorphinan, 17-cyclopropylmethyl-6,7-didehydro-4,5α-epoxy-3,14β-dihydroxy-1',3"-ethylene-5'-methoxy-6',7'-benzo-6,7,2',3'-indolomorphinan, 17-allyl-6,7-didehydro-4,5α-epoxy-3,14β-dihydroxy-1',3"-ethylene-5'-methoxy-6',7'-benzo-6,7,2',3'-indolomorphinan, 17-cyclopropylmethyl-6,7-didehydro-4,5α-epoxy-3-hydroxy-14β-methoxy-1',3"-ethylene-5'-methoxy-6',7'-benzo-6,7,2',3'-indolomorphinan, 17-allyl-6,7-didehydro-4,5α-epoxy-3-hydroxy-14β-methoxy- 1',3"-ethylene-5'-methoxy-6',7'-benzo-6,7,2',3'-indolomorphinan, 17-cyclopropylmethyl-6,7-didehydro-4,5α-epoxy-3-methoxy-14β-hydroxy-1',3"-ethylene-5'-methoxy-6',7'-benzo-6,7,2',3'-indolomorphinan, 17-allyl-6,7-didehydro-4,5α-epoxy-3-methoxy-14β-hydroxy-1',3"-ethylene-5,-methoxy-6',7'-benzo-6,7,2',3'-indolomorphinan, 17-cyclopropylmethyl-6,7-didehydro-4,5α-epoxy-3,14β-dihydroxy-1',3"-ethylene-5'-methoxy-6',7'-benzo-6,7,2',3'-indolomorphinan, 17-allyl-6,7-didehydro-4,5α-epoxy-3,14β-dihydoroxy-1',3"-ethylene-5'-methoxy-6',7'-benzo-6,7,2',3'-indolomorphinan, 17-cyclopropylmethyl-6,7-didehydro-4,5α-epoxy-3,14β-dihydroxy-1',3"-ethylene-5'-nitro-6',7'-benzo-6,7,2',3'-indolomorphinan, 17-allyl-6,7-didehydro-4,5α-epoxy-3,14β-dihydroxy-1',3"-ethylene-5'-nitro-6',7'-benzo-6,7,2',3'-indolomorphinan, 17-cyclopropylmethyl-6,7-didehydro-4,5α-epoxy-3-hydroxy-14β-methoxy-1',3"-ethylene-5'-nitro-6',7'-benzo-6,7,2',3'-indolomorphinan, 17-allyl-6,7-didehydro-4,5α-epoxy-3-hydroxy-14β-methoxy-1',3"-ethylene-5'-nitro-6',7'-benzo-6,7,2',3'-indolomorphinan, 17-cyclopropylmethyl-6,7-didehydro-4,5α-epoxy-3-methoxy-14β-hydroxy-1',3"-ethylene-5'-nitro-6',7'-benzo-6,7,2',3'-indolomorphinan, 17-allyl-6,7-didehydro-4,5α-epoxy-3-methoxy-14β-hydroxy-1',3"-ethylene-5'-nitro-6',7'-benzo-6,7,2',3'-indolomorphinan, 17-cyclopropylmethyl-6,7-didehydro-4,5α-epoxy-3,14β-dihydroxy-1',3"-ethylene-5'-nitro-6',7'-benzo-6,7,2',3'-indolomorphinan, 17-allyl-6,7-didehydro-4,5α-epoxy-3,14β-dihydoroxy-1',3"-ethylene-5'-nitro-6',7'-benzo-6,7,2',3'-indolomorphinan.

Moreover two of $R^5$ together form the benzene ring, that is, compound 3 of the formula:

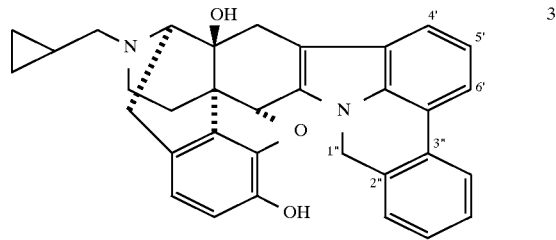

which is named according to former nomenclature 17-cyclopropylmethyl-6,7-didehydro-4,5α-epoxy-3,14β- dihydroxy-1',7'-(2",3"-benzotrimethylene)-6,7,2',3'-indolomorphinan, is included in the present invention. So specific examples of the compounds employed in the present invention include 17-allyl-6,7-didehydro-4,5α-epoxy-3,14β dihydroxy-1',7'-(2",3"-benzotrimethylene)-6,7,2',3'-indolomorphinan, 17-cyclopropylmethyl-6,7-didehydro-4,5α-epoxy-3-hydroxy-14β-methoxy-1',7'-(2",3"-benzotrimethylene)-6,7,2',3'-indolomorphinan, 17-allyl-6,7-didehydro-4,5α-epoxy-3-hydroxy-14β-methoxy-1',7'-(2",3"-benzotrimethylene)-6,7,2',3'-indolomorphinan, 17-cyclopropylmethyl-6,7-didehydro-4,5α-epoxy-3-methoxy-14β-hydroxy-1',7'-(2",3"-benzotrimethylene)-6,7,2',3'-indolomorphinan, 17-allyl-6,7-didehydro-4,5α-epoxy-3-methoxy-14β-hydroxy-1',7'-(2",3"-benzotrimethylene)-6,7,2',3'-indolomorphinan, 17-cyclopropylmethyl-6,7-didehydro- 4,5α-epoxy-3,14β-dihydroxy-1',7'-(2",3"-benzotrimethylene)-6,7,2',3'-indolomorphinan, 17-allyl-6,7-didehydro-4,5α-epoxy-3,14β-dihydroxy-1',7'-(2",3"-benzotrimethylene)-6,7,2',3'-indolomorphinan, 17-cyclopropylmethyl-6,7-didehydro-4,5α-epoxy-3,14β-dihydroxy-1',7'-(2",3"-benzotrimethylene)-5'-fluoro-6,7,2',3'-indolomorphinan, 17-allyl-6,7-didehydro-4,5α-epoxy-3,14β-dihydroxy-1',7'-(2",3"-benzotrimethylene)-5'-fluoro-6,7,2',3'-indolomorphinan, 17-cyclopropylmethyl-6,7-didehydro-4,5α-epoxy-3-hydroxy-14β-methoxy-1',7'-(2",3"-benzotrimethylene)-5'-fluoro-6,7,2',3'-indolomorphinan, 17-allyl-6,7-didehydro-4,5α-epoxy-3-hydroxy-14β-methoxy-1',7'-(2",3"-benzotrimethylene)-5'-fluoro-6,7,2',3'-indolomorphinan, 17-cyclopropylmethyl-6,7-didehydro-4,5α-epoxy-3-methoxy-14β-hydroxy-1',7'-(2",3"-benzotrimethylene)-5'-fluoro-6,7,2',3'-indolomorphinan, 17-allyl-6,7-didehydro-4,5α-epoxy-3-methoxy-14β-hydroxy-1',7'-(2",3"-benzotrimethylene)-5'-fluoro-6,7,2',3'-indolomorphinan, 17-cyclopropylmethyl-6,7-didehydro-4,5α-epoxy-3,14β-dihydroxy-1',7'-(2",3"-benzotrimethylene)-5'-fluoro-6,7,2',3'-indolomorphinan, 17-allyl-6,7-didehydro-4,5α-epoxy-3,14β-dihydroxy-1',7'-(2",3"-benzotrimethylene)-5'-fluoro-6,7,2',3'-indolomorphinan, 17-cyclopropylmethyl-6,7-didehydro-4,5α-epoxy-3,14β-dihydroxy-1',7'-(2",3"-benzotrimethylene)-5'-chloro-6,7,2',3'-indolomorphinan, 17-allyl-6,7-didehydro-4,5α-epoxy-3,14β-dihydroxy-1',7'-(2",3"-benzotrimethylene)-5'-chloro-6,7,2',3'-indolomorphinan, 17-cyclopropylmethyl-6,7-didehydro-4,5α-epoxy-3-hydroxy-14β-methoxy-1',7'-(2",3"-benzotrimethylene)-5'-chloro-6,7,2',3'-indolomorphinan, 17-allyl-6,7-didehydro-4,5α-epoxy-3-hydroxy-14β-methoxy-1',7'-(2",3"-benzotrimethylene)-5'-chloro-6,7,2',3'-indolomorphinan, 17-cyclopropylmethyl-6,7-didehydro-4,5α-epoxy-3-methoxy-14β-hydroxy-1',7'-(2",3"-benzotrimethylene)-5'-chloro-6,7,2',3'-indolomorphinan, 17-allyl-6,7-didehydro-4,5α-epoxy-3-methoxy-14β-hydroxy-1',7'-(2",3"-benzotrimethylene)-5'-chloro-6,7,2',3'-indolomorphinan, 17-cyclopropylmethyl-6,7-didehydro-4,5α-epoxy-3,14β-dihydroxy-1',7'-(2",3"-benzotrimethylene)-5'-chloro-6,7,2',3'-indolomorphinan, 17-allyl-6,7-didehydro-4,5α-epoxy-3,14β-dihydroxy-1',7'-(2",3"-benzotrimethylene)-5'-chloro-6,7,2',3'-indolomorphinan, 17-cyclopropylmethyl-6,7-didehydro-4,5α-epoxy-3,14β-dihydroxy-1',7'-(2",3"-benzotrimethylene)-5'-bromo-6,7,2',3'-indolomorphinan, 17-allyl-6,7-didehydro-4,5α-epoxy-3,14β-dihydroxy-1',7'-(2",3"-benzotrimethylene)-5'-bromo-6,7,2',3'-indolomorphinan, 17-cyclopropylmethyl-6,7-didehydro-4,5α-epoxy-3-hydroxy-14β-methoxy-1',7'-(2",3"-benzotrimethylene)-5'-bromo-6,7,2',3'-indolomorphinan, 17-allyl-6,7-didehydro-4,5α-epoxy-3-hydroxy-14β-methoxy-1',7'-(2",3"-benzotrimethylene)-5'-bromo-6,7,2',3'-indolomorphinan, 17-cyclopropylmethyl- 6,7-didehydro-4,5α-epoxy-3-methoxy-14β-hydroxy-1',7'-(2",3"-benzotrimethylene)-5'-bromo-6,7,2',3'-indolomorphinan, 17-allyl-6,7-didehydro-4,5α-epoxy-3-methoxy-14β-hydroxy-1',7'-(2",3"-benzotrimethylene)-5'-bromo-6,7,2',3'-indolomorphinan, 17-cyclopropylmethyl-6,7-didehydro-4,5α-epoxy-3,14β-dihydroxy-1',7'-(2",3"-benzotrimethylene)-5'-bromo-6,7,2',3'-indolomorphinan, 17-allyl-6,7-didehydro-4,5α-epoxy-3,14β-dihydroxy-1',7'-(2",3"-benzotrimethylene)-5'-bromo-6,7,2',3'-indolomorphinan, 17-cyclopropylmethyl-6,7-didehydro-4,5α-epoxy-3,14β-dihydroxy-1',7'-(2",3"-benzotrimethylene)-5'-methyl-6,7,2',3'-indolomorphinan, 17-allyl-6,7-didehydro-4,5α-epoxy-3,14β-dihydroxy-1',7'-(2",3"-benzotrimethylene)-5'-methyl-6,7,2',3'-indolomorphinan, 17-cyclopropylmethyl-6,7-didehydro-4,5α-epoxy-3-hydroxy-14β-methoxy-1',7'-(2",3"-benzotrimethylene)-5'-methyl-6,7,2',3'-indolomorphinan, 17-allyl-6,7-didehydro-4,5α-epoxy-3-hydroxy-14β-methoxy-1',7'-(2",3"-benzotrimethylene)-5'-methyl-6,7,2',3'-indolomorphinan, 17-cyclopropylmethyl-6,7-didehydro-4,5α-epoxy-3-methoxy-14β-hydroxy-1',7'-(2",3"-benzotrimethylene)-5'-methyl-6,7,2',3'-indolomorphinan, 17-allyl-6,7-didehydro-4,5α-epoxy-3-methoxy-14β-hydroxy-1',7'-(2",3"-benzotrimethylene)-5'-methyl-6,7,2',3'-indolomorphinan, 17-cyclopropylmethyl-6,7-didehydro-4,5α-epoxy-3,14β-dihydroxy-1',7'-(2",3"-benzotrimethylene)-5'-methyl-6,7,2',3'-indolomorphinan, 17-allyl-6,7-didehydro-4,5α-epoxy-3,14β-dihydroxy- 1',7'-(2",3"-benzotrimethylene)-5'-methyl-6,7,2',3'-indolomorphinan, 17-cyclopropylmethyl-6,7-didehydro-4,5α-epoxy-3,14βdihydroxy-1',7'-(2",3"-benzotrimethylene)-5'-methoxy-6,7,2',3'-indolomorphinan, 17-allyl-6,7-didehydro-4,5α-epoxy-3,14β-dihydroxy-1',7'-(2",3"-benzotrimethylene)-5'-methoxy-6,7,2',3'-indolomorphinan, 17-cyclopropylmethyl-6,7-didehydro-4,5α-epoxy-3-hydroxy-14β-methoxy-1',7'-(2",3"-benzotrimethylene)-5'-methoxy-6,7,2',3'-indolomorphinan, 17-allyl-6,7-didehydro-4,5α-epoxy-3-hydroxy-14β-methoxy-1',7'-(2",3"-benzotrimethylene)-5'-methoxy-6,7,2',3'-indolomorphinan, 17-cyclopropylmethyl-6,7-didehydro-4,5α-epoxy-3-methoxy-14β-hydroxy-1',7'-(2",3"-benzotrimethylene)-5'-methoxy-6,7,2',3'-indolomorphinan, 17-allyl-6,7-didehydro-4,5α-epoxy-3-methoxy-14β-hydroxy-1',7'-(2",3"-benzotrimethylene)-5'-methoxy-6,7,2',3'-indolomorphinan, 17-cyclopropylmethyl-6,7-didehydro-4,5α-epoxy-3,14β-dihydroxy-1',7'-(2",3"-benzotrimethylene)-5'-methoxy-6,7,2',3'-indolomorphinan, 17-allyl-6,7-didehydro-4,5α-epoxy-3,14β-dihydroxy-1',7'-(2",3"-benzotrimethylene)-5'-methoxy-6,7,2',3'-indolomorphinan, 17-cyclopropylmethyl-6,7-didehydro-4,5α-epoxy-3,14β-dihydroxy-1',7'-(2",3"-benzotrimethylene)-5'-nitro-6,7,2',3'-indolomorphinan, 17-allyl-6,7-didehydro-4,5α-epoxy-3,14β-dihydroxy-1',7'-(2",3"-benzotrimethylene)-5'-nitro-6,7,2',3'-indolomorphinan, 17-cyclopropylmethyl-6,7-didehydro- 4,5α-epoxy-3-hydroxy-14β-methoxy-1',7'-(2",3"-benzotrimethylene)-5'-nitro-6,7,2',3'-indolomorphinan, 17-allyl-6,7-didehydro-4,5α-epoxy-3-hydroxy-14β-methoxy-1',7'-(2",3"-benzotrimethylene)-5'-nitro-6,7,2',3'-indolomorphinan, 17-cyclopropylmethyl-6,7-didehydro-4,5α-epoxy-3-methoxy-14β-hydroxy-1',7'-(2",3"-benzotrimethylene)-5'-nitro-6,7,2',3'-indolomorphinan, 17-allyl-6,7-didehydro-4,5α-epoxy-3-methoxy-14β-hydroxy-1',7'-(2",3"-benzotrimethylene)-5'-nitro-6,7,2',3'-indolomorphinan, 17-cyclopropylmethyl-6,7-didehydro-4,5α-epoxy-3,14β-dihydroxy-1',7'-(2",3"-benzotrimethylene)-5'-nitro-6,7,2',3'-indolomorphinan, 17-allyl-6,7-didehydro-4,5α-epoxy-3,14β-dihydroxy-1',7'-(2",3"-benzotrimethylene)-5'-nitro-6,7,2',3'-indolomorphinan.

Practically, the compounds of the present invention represented by the general formula (I) can be obtained according to the process shown in Chart 1 below.

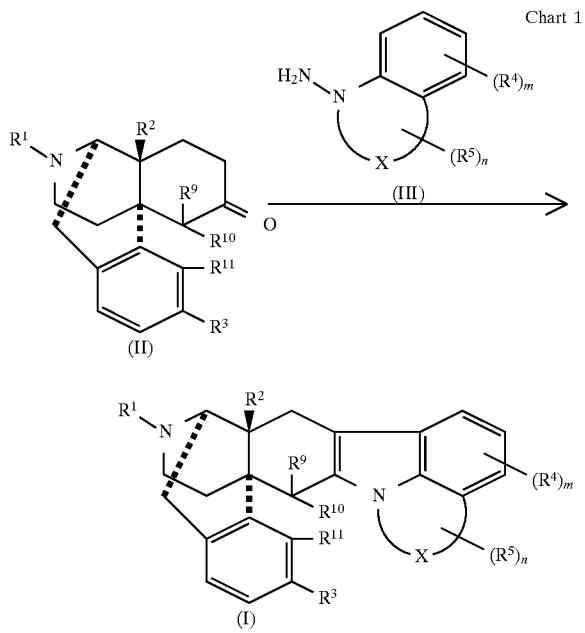

Chart 1

Specifically, a morphinan derivative represented by the above general formula (II) (in the formula, definitions of $R^1$, $R^2$, $R^3$, $R^9$, $R^{10}$, and $R^{11}$ are the same as the aforementioned definitions) is reacted with a hydrazine derivative represented by the above general formula (III) (in the formula, definitions of —X—, m, n, $R^4$, and $R^5$ are the same as the aforementioned definitions) in a solvent in the presence of an acid catalyst.

Examples of solvents which can be used herein include alcoholic solvents such as methanol, ethanol, 1-propanol, and 2-propanol; aprotic dipolar solvents such as DMF and DMSO; aromatic hydrocarbon solvents such as benzene, toluene, and xylene; ether solvents such as diethyl ether, THF, and DME; halogeno carbon solvents such as dichloroethane, chloroform, carbon tetrachloride, and 1,2-dichloroethane; and organic acids capable of being used as solvents such as acetic acid and propionic acid. Among these solvents, preferred are alcoholic solvents such as methanol, ethanol, 1-propanol, and 2-propanol; aprotic dipolar solvents such as DMF and DMSO; and organic acids capable of being used as solvents such as acetic acid and propionic acid. In particular, methanol, ethanol, DMF, and acetic acid are especially preferred.

Examples of the acid catalyst which can be used in the present invention include inorganic acids such as hydrochloric acid, sulfuric acid, nitric acid, hydrobromic acid, and hydroeodic acid; sulfonic acids such as methanesulfonic acid, ethanesulfonic acid, benzenesulfonic acid, p-toluenesulfonic acid, and camphorsulfonic acid; carboxylic acids such as acetic acid, lactic acid, citric acid, oxalic acid, glutaric acid, malic acid, tartaric acid, fumaric acid, mandelic acid, maleic acid, benzoic acid, and phthalic acid (incidentally, although the reaction may not smoothly progress with calboxylic acid alone, a strong acid may optionally be added as a cocatalyst in such a case); and acidic ion-exchange resin. Among these acid catalysts, hydrochloric acid, sulfuric acid, methanesulfonic acid, p-toluenesulfonic acid, and acidic ion-exchange resin are preferably used. Further, the amount of the acid catalyst to be added is 1 to 30 equivalent amounts, and preferably, 1 to 10 equivalent amounts relative to the total amount of base present in the reaction system. The acid catalyst may be added after converting the base component into salt, or may be added into the reaction mixture in a desired amount. The reaction temperature is 0° to 300° C., preferably 25° to 170° C., and more preferably 60° to 120° C.

As a result of pharmacological evaluations in vitro and in vivo, the compounds of the present invention expressed by the general formula (I) were found to be compounds which act on δ opioid receptors and have a strong antitussive and analgesic activity, as shown with practical examples described below. Accordingly, the compounds of the present invention are expected to serve as effective antitussives and analgesics.

Actually, in the pharmaceutical field, they are useful as remedies for various respiratory diseases such as cold syndrome, acute bronchitis, chronic bronchitis, bronchiectasis, pneumonia, silicosis and silicotuberculosis, lung cancer, upper respiratory inflammation (such as pharyngitis, laryngitis and gravedo), asthmatic bronchitis, bronchial asthma, infantile asthma, (chronic) pulmonary emphysema, pneumoconiosis, pulmonary fibrosis, pneumosilicosis, lung abscess, pleurisy, tonsillitis, cough urticaria, and whooping cough; as cough inhibitors such as for bronchography and bronchial examinations; and as analgesics such as against postoperative pain, cancer pain, and other ordinary pain.

On clinical application of the antitussive/analgesic agent according to the present invention, the compound may be a free base or a salt thereof, or may be used in combination with suitable excipients such as stabilizers, buffers, diluents, isotonizing agents, and antiseptics. Further, the antitussive/analgesic agent of the present invention may be orally administered in the form of a tablet, a capsule, a granule, a powder, or a syrup; may be parenterally administered in the form of an injection solution, a suppository, or a liquid; or may be locally administered in the form of an ointment, a cream, or a stupe. Preferably, the antitussive/analgesic agent of the present invention contains 0.00001 to 90% by weight of the above-described active principle, and more preferably, 0.0001 to 70% by weight. The dosage is optionally determined according to the disease condition, age and body weight of the patient, and the administration method. For an adult, in terms of the active principle, the dosage for injection is 0.1 μg to 1 g per day, and the dosage for oral administration is 1 μg to 10 g. In each case, either single administration or multiple administration can be employed.

EXAMPLES

The present invention will be further illustrated in detail with reference to the following examples to which the present invention is not limited.

[Example 1]
17-Cyclopropylmethyl-6,7-didehydro-4,5α-epoxy-3,14β-dihydroxy-1',7'-ethylene-6,7,2',3'-indolomorphinan 1 Hydrochloride

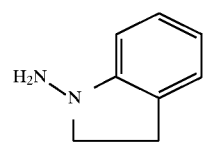

1a

-continued

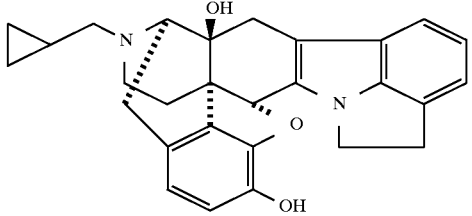

Naltolexone hydrochloride (383 mg), N-aminoindoline 1a methanesulfonate (375 mg, 1.1 equivalent amounts), and methanesulfonic acid (0.14 ml, 2 equivalent amounts) were mixed in ethanol (8 ml), and refluxed for 8.5 hours. After being allowed to cool, the resultant was poured into a 5% sodium hydroxide solution (20 ml), subjected to extraction with chloroform (20 ml×3), dried over anhydrous magnesium sulfate, and concentrated.

The crude product thus obtained was then purified through silica gel column chromatography (Silica 7734 manufactured by Merck Ltd. 75 g; chloroform/methanol= 50/1→30/1) to obtain a free base substance of the object product. This free base substance was converted into a hydrochloric acid salt in methanol, and the resultant precipitate was collected by filtration to obtain the object product.

[Examples 2 to 10]

According to the same manner as in Example 1, the following object products:

17-cyclopropylmethyl-6,7-didehydro-4,5α-epoxy-3,14β-dihydroxy-1',3"-ethylene-6',7'-benzo-6,7,2',3'-indolomorphinan 2 methanesulfonate;

17-cyclopropylmethyl-6,7-didehydro-4,5α-epoxy-3,14β-dihydroxy-1',7'-(2",3"-benzotrimethylene)- 6,7,2',3'-indolomorphinan 3 methanesulfonate;

17-cyclopropylmethyl-6,7-didehydro-4,5α-epoxy-3,14β-dihydroxy-1',7'-trimethylene-6,7,2',3'-indolomorphinan 4 methanesulfonate;

17-cyclopropylmethyl-6,7-didehydro-4,5α-epoxy-3,14β-dihydroxy-1',7'-trimethylene-4'-methyl-6,7,2',3'-indolomorphinan 5 methanesulfonate;

17-cyclopropylmethyl-6,7-didehydro-4,5α-epoxy-3,14β-dihydroxy-1',7'-trimethylene-6'-methoxy-6,7,2',3'-indolomorphinan 6 methanesulfonate;

17-cyclopropylmethyl-6,7-didehydro-4,5α-epoxy-3,14β-dihydroxy-1',7'-trimethylene-5'-methyl-6,7,2',3'-indolomorphinan 7 methanesulfonate;

17-cyclopropylmethyl-6,7-didehydro-4,5α-epoxy-3,14β-dihydroxy-1',7'-trimethylene-5'-chloro-6,7,2',3'-indolomorphinan 8 hydrochloride;

17-cyclopropylmethyl-6,7-didehydro-4,5α-epoxy-3,14β-dihydroxy-1',7'-tetramethylene-6,7,2',3'-indolomorphinan 9 methanesulfonate; and 17-cyclopropylmethyl-6,7-didehydro-4,5α-epoxy-3,14β-dihydroxy-1',7'-trimethylene-5'-fluoro-6,7,2',3'-indolomorphinan 10 methanesulfonate were obtained using the following compounds instead of N-aminoindoline, respectively:

N-amino-1-aza-2,3-dihydrophenalene 2a;
N-amino-5,6-dihydrophenanthridine 3a;
N-amino-1,2,3,4-tetrahydroquinoline 4a;
N-amino-7-methyl-1,2,3,4-tetrahydroquinoline 5a;
N-amino-5-methoxy-1,2,3,4-tetrahydroquinoline 6a;
N-amino-6-methyl-1,2,3,4-tetrahydroquinoline 7a;
N-amino-6-chloro-1,2,3,4-tetrahydroquinoline 8a;
N-amino-2,3,4,5-tetrahydro-1H-1-benzazepine 9a; and
N-amino-6-fluoro-1,2,3,4-tetrahydroquinoline 10a.

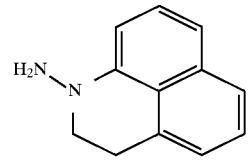

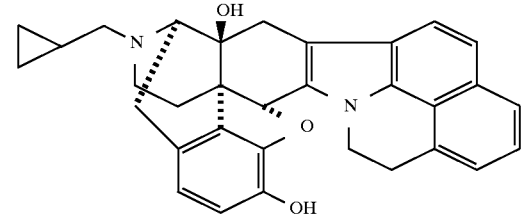

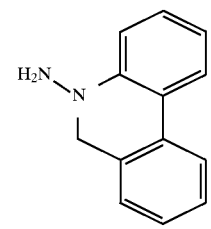

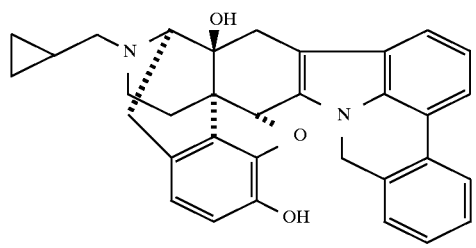

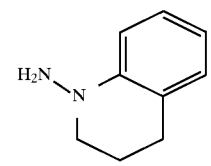

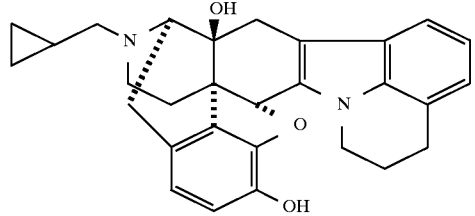

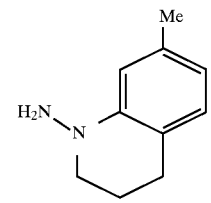

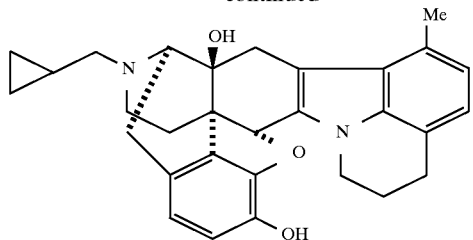

5

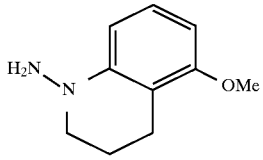

6a

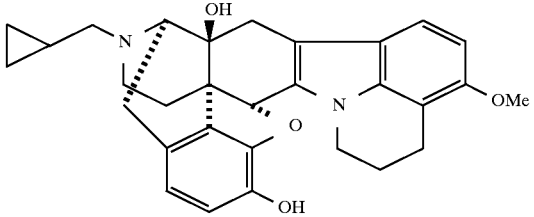

6

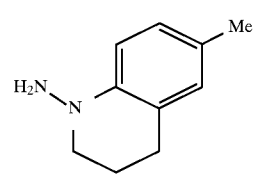

7a

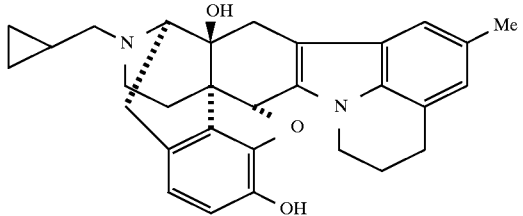

7

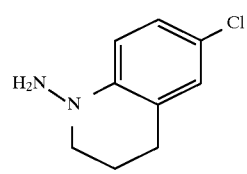

8a

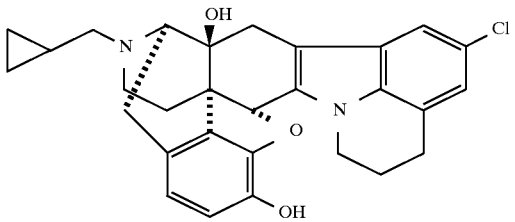

8

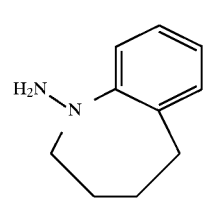

9a

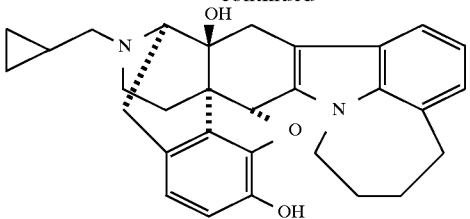

9

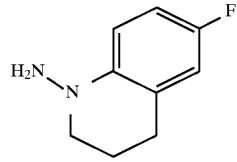

10a

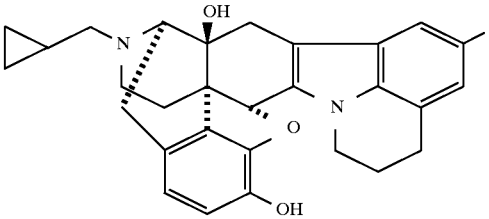

10

[Example 11]

17-Cyclopropylmethyl-6,7-didehydro-4,5α-epoxy-3-methoxy-14β-hydroxy-1',7'-trimethylene-6,7,2',3'-indolomorphinan 11 Methanesulfonate

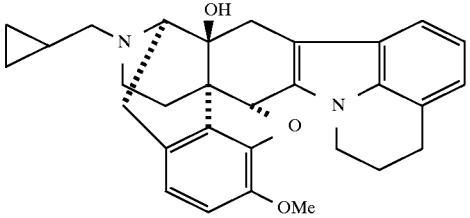

11

17-Cyclopropylmethyl-6,7-didehydro-4,5α-epoxy-3,14β-dihydroxy-1',7'-trimethylene-6,7,2',3'-indolomorphinan 4 methanesulfonate (153.9 mg) obtained in Example 4 was dissolved in anhydrous DMF (3 ml). To this solution, anhydrous potassium carbonate (110 mg, 3 equivalent amounts) and methyl iodide (33.3 μl+13.3 μl, total 2.8 equivalent amounts) were added and reacted at room temperature for 5 hours.

The resultant was then poured into a mixture of water (10 ml) and ethyl acetate (12 ml) for separation. The aqueous phase was subjected to re-extraction with ethyl acetate (7 ml), and the obtained organic phases were mixed and washed with a saturated sodium chloride solution (10 ml). The resultant was then dried over anhydrous sodium sulfate, and concentrated to obtain a crude product. This crude product was purified by silica gel column chromatography (9385 manufactured by Merck Ltd. 50 g; chloroform) to obtain a free base substance of the object product. This free base substance was dissolved in a mixture of methanol (3 ml) and chloroform (3 ml) with the addition of 1 equivalent amount of methanesulfonic acid. Subsequently, the solvent was distilled off, and the resultant was suspended in ether and collected by filtration to obtain the above-titled compound.

[Examples 12 to 18]

According to the same manner as in Example 11, the following object products:

17-cyclopropylmethyl-6,7-didehydro-4,5α-epoxy-3,6'-dimethoxy-14β-hydroxy-1',7'-trimethylene-6,7,2',3'-indolomorphinan 12 methanesulfonate;

17-cyclopropylmethyl-6,7-didehydro-4,5α-epoxy-3-methoxy-14β-hydroxy-1',7'-trimethylene-5'-methyl-6,7,2',3'-indolomorphinan 13 methanesulfonate;

17-cyclopropylmethyl-6,7-didehydro-4,5α-epoxy-3-methoxy-14β-hydroxy-1',7'-trimethylene-4'-methyl-6,7,2',3'-indolomorphinan 14 methanesulfonate;

17-cyclopropylmethyl-6,7-didehydro-4,5α-epoxy-3-methoxy-14β-hydroxy-1',7'-tetramethylene-6,7,2',3'-indolomorphinan 15 methanesulfonate;

17-cyclopropylmethyl-6,7-didehydro-4,5α-epoxy-3-methoxy-14β-hydroxy-1',7'-trimethylene-5'-fluoro-6,7,2',3'-indolomorphinan 16 methanesulfonate;

17-cyclopropylmethyl-6,7-didehydro-4,5α-epoxy-3-methoxy-14β-hydroxy-1',7'-(2",3"-benzotrimethylene)-6,7,2',3'-indolomorphinan 17 methanesulfonate; and 17-cyclopropylmethyl-6,7-didehydro-4,5α-epoxy-3-methoxy-14β-hydroxy-1',7'-trimethylene-5'-chloro-6,7,2',3'-indolomorphinan 18 hydrochloride were obtained using the following compounds instead of 17-cyclopropylmethyl-6,7-didehydro-4,5α-epoxy-3,14β-dihydroxy-1',7'-trimethylene-6,7,2',3'-indolomorphinan 4, respectively:

17-cyclopropylmethyl-6,7-didehydro-4,5α-epoxy-3,14β-dihydroxy-1',7'-trimethylene-6'-methoxy-6,7,2',3'-indolomorphinan 6;

17-cyclopropylmethyl-6,7-didehydro-4,5α-epoxy-3,14β-dihydroxy-1',7'-trimethylene-5'-methyl-6,7,2',3'-indolomorphinan 7;

17-cyclopropylmethyl-6,7-didehydro-4,5α-epoxy-3,14β-dihydroxy-1',7'-trimethylene-4'-methyl-6,7,2',3'-indolomorphinan 5;

17-cyclopropylmethyl-6,7-didehydro-4,5α-epoxy-3,14β-dihydroxy-1',7'-tetramethylene-6,7,2',3'-indolomorphinan 9;

17-cyclopropylmethyl-6,7-didehydro-4,5α-epoxy-3,14β-dihydroxy-1',7'-trimethylene-5'-fluoro-6,7,2',3'-indolomorphinan 10;

17-cyclopropylmethyl-6,7-didehydro-4,5α-epoxy-3,14β-dihydroxy-1',7'-(2",3"-benzotrimethylene)-6,7,2',3'-indolomorphinan 3; and 17-cyclopropylmethyl-6,7-didehydro-4,5α-epoxy-3,14β-dihydroxy-1',7'-trimethylene-5'-chloro-6,7,2',3'-indolomorphinan 8.

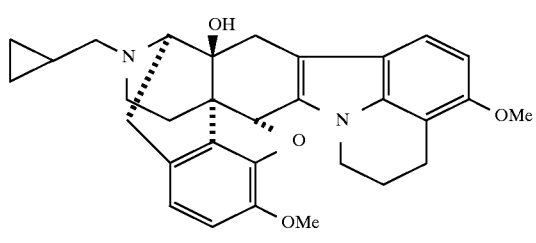

12

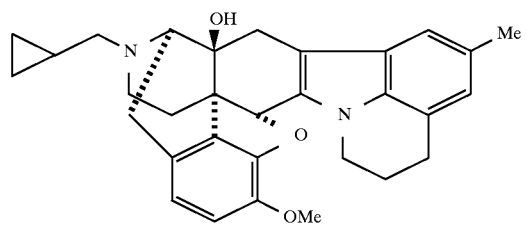

13

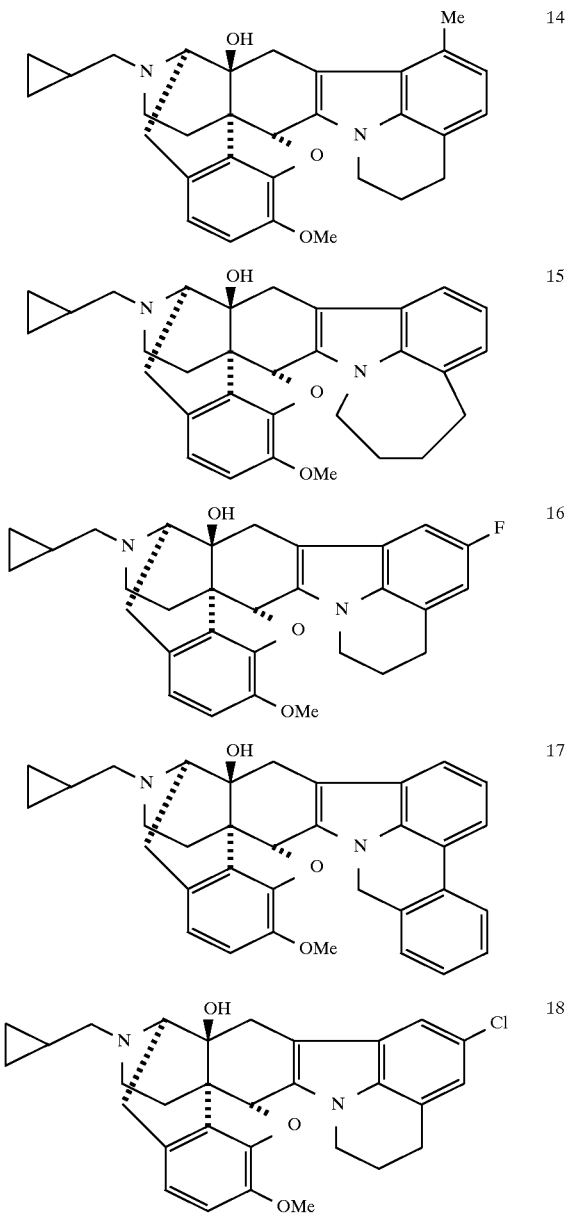

[Examples 19 to 27]

According to the same manner as in Example 1, the following object products:

17-cyclopropylmethyl-6,7-didehydro-4,5α-epoxy-3,14β-dihydroxy-1',7'-trimethylene-5'-methoxy-6,7,2',3'-indolomorphinan 19 methanesulfonate;

17-cyclopropylmethyl-6,7-didehydro-4,5α-epoxy-3,14β-dihydroxy-1',7'-trimethylene-5'-bromo-6,7,2',3'-indolomorphinan 20 methanesulfonate;

17-cyclopropylmethyl-6,7-didehydro-4,5α-epoxy-3,14β-dihydroxy-1',7'-pentamethylene-6,7,2',3'-indolomorphinan 21 methanesulfonate;

17-cyclopropylmethyl-6,7-didehydro-4,5α-epoxy-3,14β-dihydroxy-7',1'-epithioethano-6,7,2',3'-indolomorphinan 22 methanesulfonate;

17-cyclopropylmethyl-6,7-didehydro-4,5α-epoxy-3,14β-dihydroxy-7',1'-epoxyethano-6,7,2',3'-indolomorphinan 23 methanesulfonate;

17-cyclopropylmethyl-6,7-didehydro-4,5α-epoxy-3,14β-dihydroxy-1',7'-trimethylene-4'-trifluoromethyl-6,7,2',3'-indolomorphinan 24 methanesulfonate;

17-cyclopropylmethyl-6,7-didehydro-4,5α-epoxy-3,14β-dihydroxy-1',7'-(1,1-dimethylpropano)-6,7,2',3'-indolomorphinan 25 methanesulfonate;

17-cyclopropylmethyl-6,7-didehydro-4,5α-epoxy-3,14β-dihydroxy-1',7'-(2,2-dimethylpropano)-6,7,2',3'-indolomorphinan 26 methanesulfonate; and 17-cyclopropylmethyl-6,7-didehydro-4,5α-epoxy-3,14β-dihydroxy-1',7'-trimethylene-4'-methoxy-6,7,2',3'-indolomorphinan 27 methanesulfonate were obtained using the following compounds instead of N-aminoindoline, respectively:

N-amino-6-methoxy-1,2,3,4-tetrahydroquinoline 19a;
N-amino-6-bromo-1,2,3,4-tetrahydroquinoline 20a;
N-amino-1,2,3,4,5,6-hexahydro-1-benzazocine 21a;
N-amino-2,3-dihydro-1,4-benzothiazine 22a;
N-amino-2,3-dihydro-1,4-benzoxazine 23a;
N-amino-7-trifluoromethyl-1,2,3,4-tetrahydroquinoline 24a;
N-amino-4,4-dimethyl-1,2,3,4-tetrahydroquinoline 25a;
N-amino-3,3-dimethyl-1,2,3,4-tetrahydroquinoline 26a; and
N-amino-7-methoxy-1,2,3,4-tetrahydroquinoline 27a.

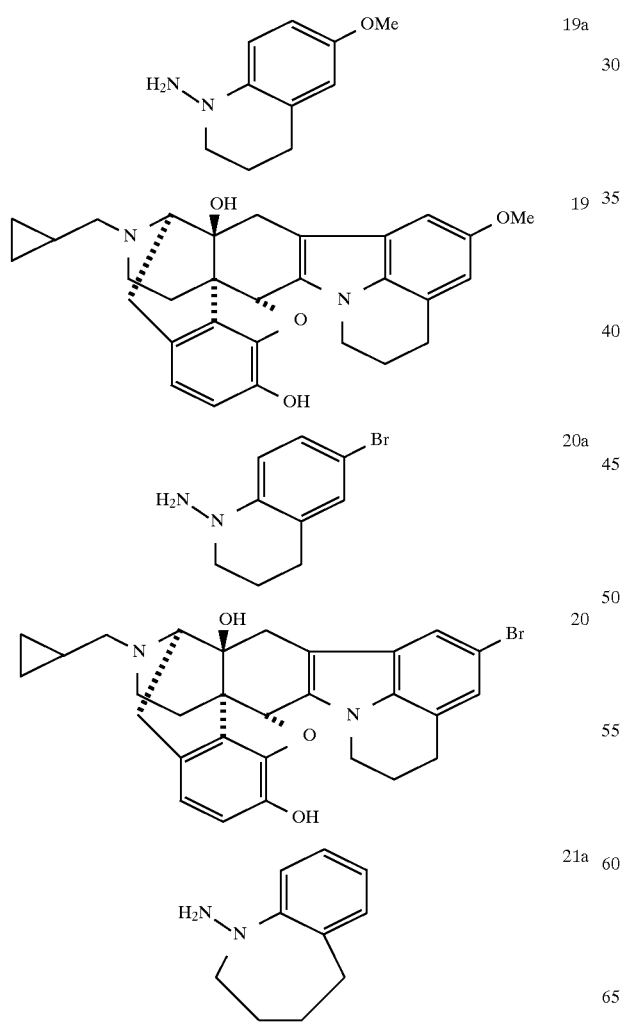

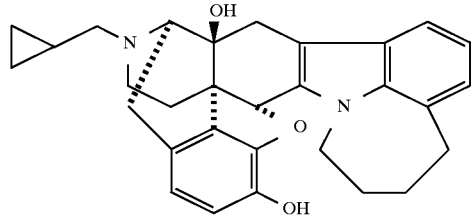

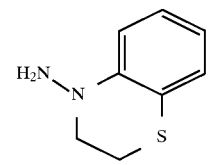

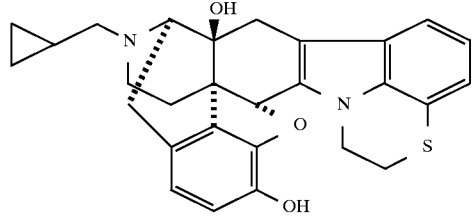

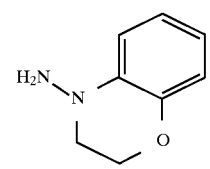

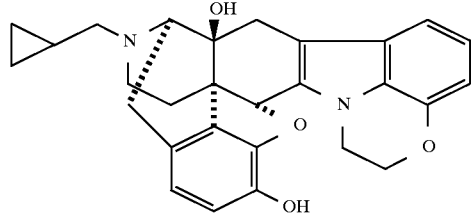

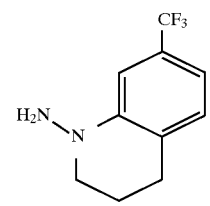

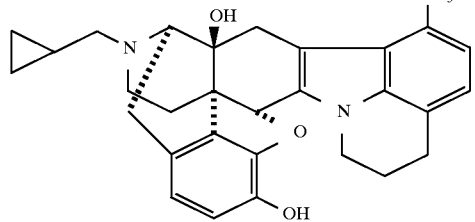

25a
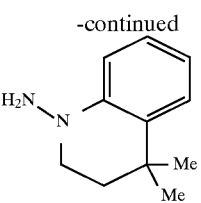

25
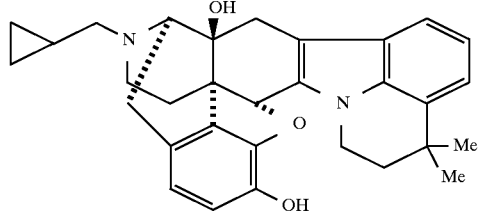

26a
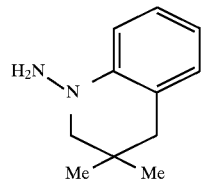

26
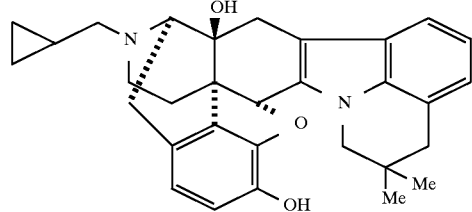

27a
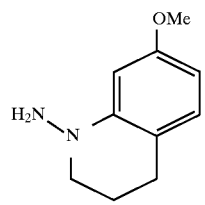

27
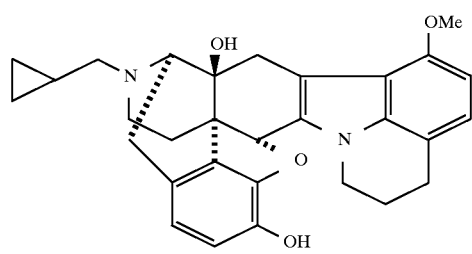

[Examples 28 to 30]

According to the same manner as in Example 1, the following object products:

17-(3-butenyl)-6,7-didehydro-4,5α-epoxy-3,14β-dihydroxy-1',7'-trimethylene-6,7,2',3'-indolomorphinan 28 methanesulfonate;

6,7-didehydro-4,5α-epoxy-3-methoxy-14β-hydroxy-1',7'-trimethylene-6,7,2',3'-indolomorphinan 29 methanesulfonate; and 17-allyl-6,7-didehydro-4,5α-epoxy-3,14β-dihydroxy-1',7'-trimethylene-6,7,2',3'-indolomorphinan 30 methanesulfonate were obtained using N-amino-1,2,3,4-tetrahydroquinoline instead of N-aminoindoline, and the following compounds instead of naltolexone, respectively:

17-(3-butenyl)-4,5α-epoxy-3,14β dihydroxy-6-ketomorphinan 28b;

4,5α-epoxy-14β-hydroxy-6-keto-3-methoxymorphinan 29b; and naloxone 30b.

28b
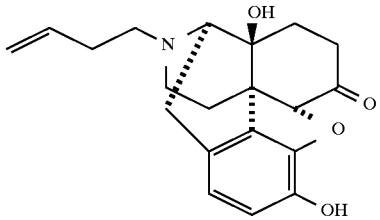

28
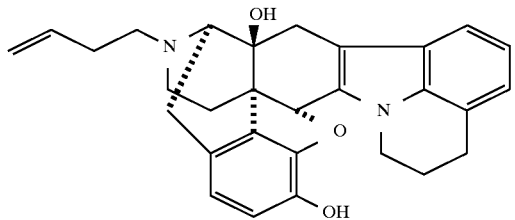

29b
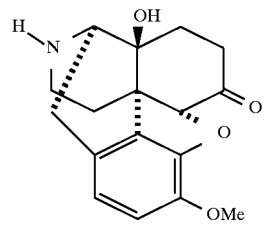

29
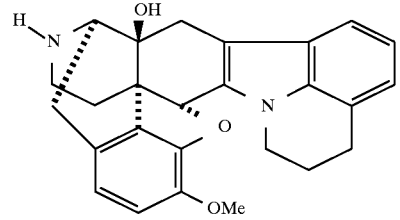

30b
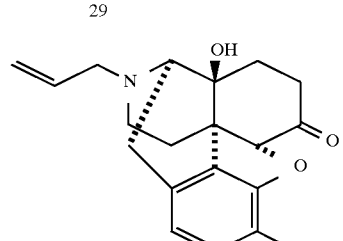

30
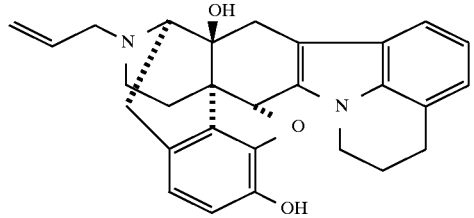

[Example 31]

17-Cyclopropylmethyl-6,7-didehydro-4,5α-epoxy-3,14β-dimethoxy-1',7'-trimethylene-6,7,2',3'-indolomorphinan 31 Methanesulfonate

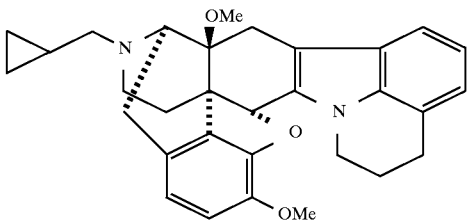

17-Cyclopropylmethyl-6,7-didehydro-4,5α-epoxy-3-methoxy-14β-hydroxy-1',7'-trimethylene-6,7,2',3'-indolomorphinan 11 (500 mg) obtained in Example 11 was dissolved in anhydrous THF (20 ml). To this solution, sodium hydride (52 mg, 1.1 equivalent amounts) and methyl iodide (500 μl, 5 equivalent amounts) were added and reacted for 3 hours while refluxing.

The resultant was then poured into a mixture of water (50 ml) and chloroform (50 ml) for separation. The resultant was then dried over anhydrous sodium sulfate, and concentrated to obtain a crude product. This crude product was purified by silica gel chromatography (7734 manufactured by Merck Ltd. 33 g; chloroform/methanol=85/1) to obtain a free base substance of the object product. This free base substance was dissolved in methanol (5 ml) with the addition of 1 equivalent amount of methanesulfonic acid. Subsequently, the solvent was distilled off, and the resultant was suspended in ether and collected by filtration to obtain the above-titled compound.

[Examples 32 to 44]

According to the same manner as in Example 11, the following object products:

- 17-(3-butenyl)-6,7-didehydro-4,5α-epoxy-3-methoxy-14β-hydroxy-1',7'-trimethylene-6,7,2',3'-indolomorphinan 32;
- 17-cyclopropylmethyl-6,7-didehydro-4,5α-epoxy-3,5'-dimethoxy-14β-hydroxy-1',7'-trimethylene-6,7,2',3'-indolomorphinan 33;
- 17-allyl-6,7-didehydro-4,5α-epoxy-3-methoxy-14β-hydroxy-1',7'-trimethylene-6,7,2',3'-indolomorphinan 34;
- 17-cyclopropylmethyl-6,7-didehydro-4,5α-epoxy-3-methoxy- 14β-hydroxy-1',7'-trimethylene-5'-bromo-6,7,2',3'-indolomorphinan 35;
- 17-cyclopropylmethyl-6,7-didehydro-4,5α-epoxy-3-methoxy-14β-hydroxy-7',1'-epithioethano-6,7,2',3'-indolomorphinan 36;
- 17-cyclopropylmethyl-6,7-didehydro-4,5α-epoxy-3-methoxy-14β-hydroxy-1',7'-pentamethylene-6,7,2',3'-indolomorphinan 37;
- 17-cyclopropylmethyl-6,7-didehydro-4,5α-epoxy-3-methoxy-14β-hydroxy-7',1'-epoxyethano-6,7,2',3'-indolomorphinan 38;
- 17-cyclopropylmethyl-6,7-didehydro-4,5α-epoxy-3-methoxy-14β-hydroxy-1',7'-trimethylene-4'-trifluoromethyl-6,7,2',3'-indolomorphinan 39;
- 17-cyclopropylmethyl-6,7-didehydro-4,5α-epoxy-3-methoxy-14β-hydroxy-1',7'-(1,1-dimethylpropano)-6,7,2',3'-indolomorphinan 40;
- 17-cyclopropylmethyl-6,7-didehydro-4,5α-epoxy-3-methoxy-14β-hydroxy-1',7'-ethylene-6,7,2',3'-indolomorphinan 41;
- 17-cyclopropylmethyl-6,7-didehydro-4,5α-epoxy-3-methoxy-14β-hydroxy-1',3''-ethylene-6',7'-benzo-6,7,2',3'-indolomorphinan 42;
- 17-cyclopropylmethyl-6,7-didehydro-4,5α-epoxy-3-methoxy-14β-hydroxy-1',7'-(2,2-dimethylpropano)-6,7,2',3'-indolomorphinan 43; and
- 17-cyclopropylmethyl-6,7-didehydro-4,5α-epoxy-3,4'-dimethoxy-14β-hydroxy-1',7'-trimethylene- 6,7,2',3'-indolomorphinan 44 were obtained using the following compounds instead of 17-cyclopropylmethyl-6,7-didehydro-4,5α-epoxy-3,14β-dihydroxy-1',7'-trimethylene-6,7,2',3'-indolomorphinan 4, respectively:

- 17-(3-butenyl)-6,7-didehydro-4,5α-epoxy-3,14β-dihydroxy-1',7'-trimethylene-6,7,2',3'-indolomorphinan 28;
- 17-cyclopropylmethyl-6,7-didehydro-4,5α-epoxy-3,14β-dihydroxy-1',7'-trimethylene-5'-methoxy-6,7,2',3'-indolomorphinan 19;
- 17-allyl-6,7-didehydro-4,5α-epoxy-3,14β-dihydroxy-1',7'-trimethylene-6,7,2',3'-indolomorphinan 30;
- 17-cyclopropylmethyl-6,7-didehydro-4,5α-epoxy-3,14β-dihydroxy-1',7'-trimethylene-5'-bromo-6,7,2',3'-indolomorphinan 20;
- 17-cyclopropylmethyl-6,7-didehydro-4,5α-epoxy-3,14β-dihydroxy-7',1'-epithioethano-6,7,2',3'-indolomorphinan 22;
- 17-cyclopropylmethyl-6,7-didehydro-4,5α-epoxy-3,14β-dihydroxy-1',7'-pentamethylene-6,7,2',3'-indolomorphinan 21;
- 17-cyclopropylmethyl-6,7-didehydro-4,5α-epoxy-3,14β-dihydroxy-7',1'-epoxyethano-6,7,2',3'-indolomorphinan 23;
- 17-cyclopropylmethyl-6,7-didehydro-4,5α-epoxy-3,14β-dihydroxy-1',7'-trimethylene-4'-trifluoromethyl-6,7,2',3'-indolomorphinan 24;
- 17-cyclopropylmethyl-6,7-didehydro-4,5α-epoxy-3,14β-dihydroxy-1',7'-(1,1-dimethylpropano)- 6,7,2',3'-indolomorphinan 25;
- 17-cyclopropylmethyl-6,7-didehydro-4,5α-epoxy-3,14β-dihydroxy-1',7'-ethylene-6,7,2',3'-indolomorphinan 1;
- 17-cyclopropylmethyl-6,7-didehydro-4,5α-epoxy-3,14β-dihydroxy-1',3''-ethylene-6',7'-benzo-6,7,2',3'-indolomorphinan 2;
- 17-cyclopropylmethyl-6,7-didehydro-4,5α-epoxy-3,14β-dihydroxy-1',7'-(2,2-dimethylpropano)-6,7,2',3'-indolomorphinan 26; and
- 17-cyclopropylmethyl-6,7-didehydro-4,5α-epoxy-3,14β-dihydroxy-1',7'-trimethylene-4'-methoxy-6,7,2',3'-indolomorphinan 27.

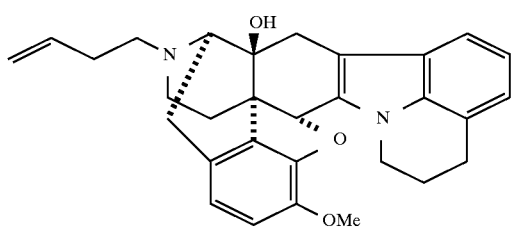

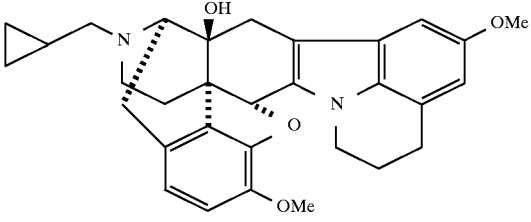

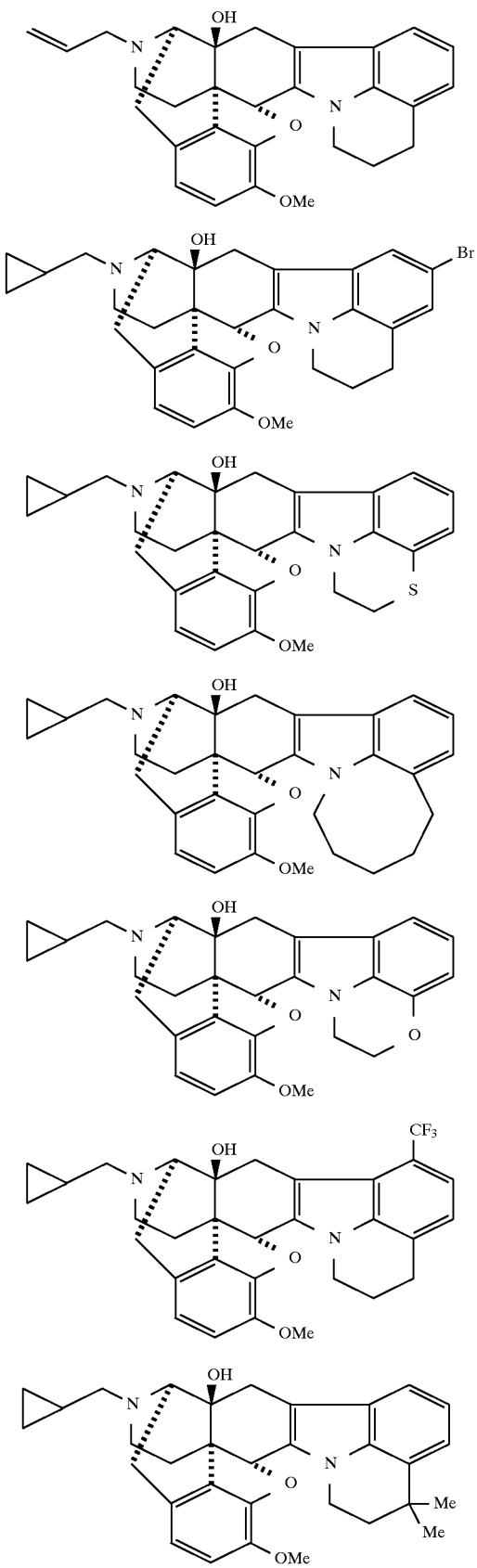
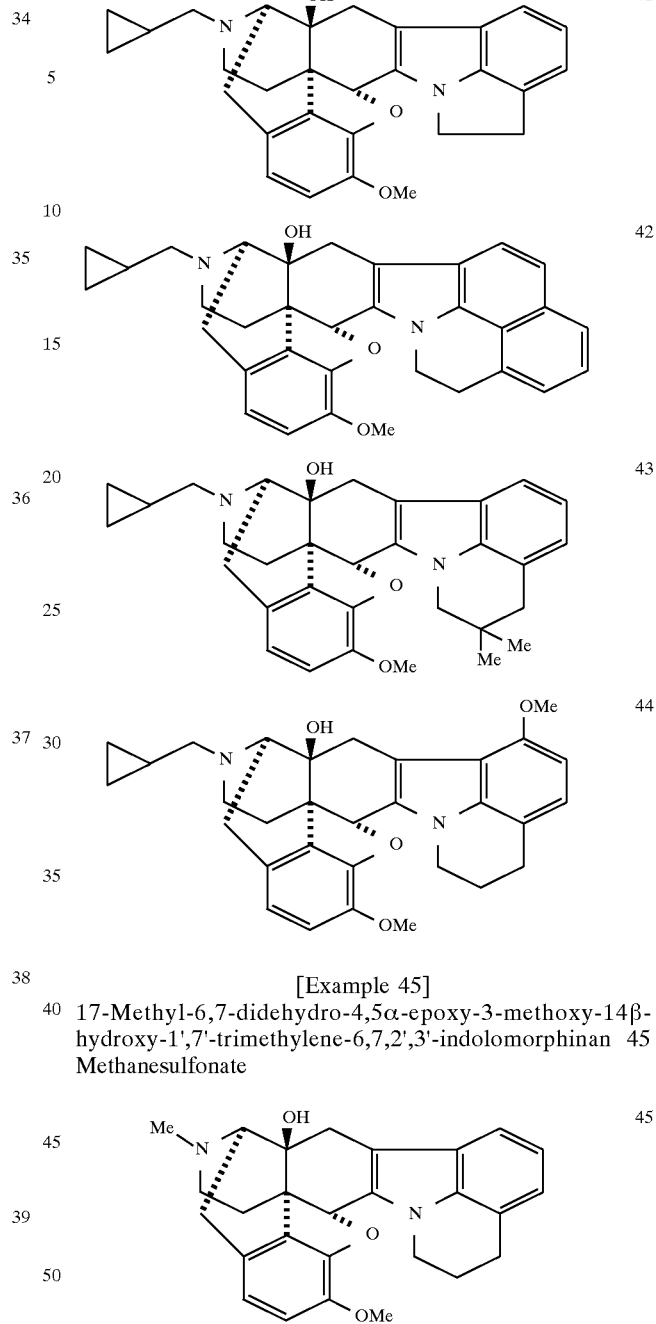

[Example 45]

17-Methyl-6,7-didehydro-4,5α-epoxy-3-methoxy-14β-hydroxy-1',7'-trimethylene-6,7,2',3'-indolomorphinan Methanesulfonate 6,7-Didehydro-4,5α-epoxy-3-methoxy-14β-hydroxy-1',7'-trimethylene-6,7,2',3'-indolomorphinan 29 (400 mg) obtained in Example 29 was dissolved in anhydrous DMF (5 ml). To this solution, anhydrous potassium carbonate (216 mg, 1.5 equivalent amounts) and methyl iodide (65 μl, 1 equivalent amount) were added and reacted at room temperature for 1.5 hours.

The resultant was then poured into a mixture of water (50 ml) and ether (50 ml) for separation. The aqueous phase was subjected to re-extraction with ether (20 ml×3), and the obtained organic phases were mixed, dried over anhydrous sodium sulfate, and concentrated. The crude product thus obtained was purified by silica gel column chromatography (9385 manufactured by Merck Ltd. 35 g; chloroform/ammonia-saturated chloroform=20/1→5/1) to obtain a free base substance of the object product. This free base substance was dissolved in methanol (5 ml) with the addition of 1 equivalent amount of methanesulfonic acid. Subsequently, the solvent was distilled off, and the resultant was suspended in ether and collected by filtration to obtain the above-titled compound. [Examples 46 to 54]

The following compounds were obtained in the same manner as in Example 45 through the alkylation of the secondary nitrogen in 6,7-didehydro-4,5α-epoxy-3-methoxy-14β-hydroxy-1',7'-trimethylene-6,7,2',3'-indolomorphinan 29:

- 17-cyclobutylmethyl-6,7-didehydro-4,5α-epoxy-3-methoxy-14β-hydroxy-1',7'-trimethylene-6,7,2',3'-indolomorphinan 46 methanesulfonate;
- 17-phenethyl-6,7-didehydro-4,5α-epoxy-3-methoxy-14β-hydroxy-1',7'-trimethylene-6,7,2',3'-indolomorphinan 47 phosphate;
- 17-benzyl-6,7-didehydro-4,5α-epoxy-3-methoxy-14β-hydroxy-1',7'-trimethylene-6,7,2',3'-indolomorphinan 48 hydrochloride;
- 17-prenyl-6,7-didehydro-4,5α-epoxy-3-methoxy-14β-hydroxy-1',7'-trimethylene-6,7,2',3'-indolomorphinan 49 methanesulfonate;
- 17-cinnamyl-6,7-didehydro-4,5α-epoxy-3-methoxy-14β-hydroxy-1',7'-trimethylene-6,7,2',3'-indolomorphinan 50 hydrochloride;
- 17-butyl-6,7-didehydro-4,5α-epoxy-3-methoxy-14β-hydroxy-1',7'-trimethylene-6,7,2',3'-indolomorphinan 51 hydrochloride;
- 17-(furan-2-ylmethyl)-6,7-didehydro-4,5α-epoxy-3-methoxy-14β-hydroxy-1',7'-trimethylene-6,7,2',3'-indolomorphinan 52 methanesulfonate;
- 17-cyclohexyl-6,7-didehydro-4,5α-epoxy-3-methoxy-14β-hydroxy-1',7'-trimethylene-6,7,2',3'-indolomorphinan 53 hydrochloride; and
- 17-(thiophene-2-ylethyl)-6,7-didehydro-4,5α-epoxy-3-methoxy-14β-hydroxy-1',7'-trimethylene-6,7,2',3'-indolomorphinan 54 hydrochloride.

46

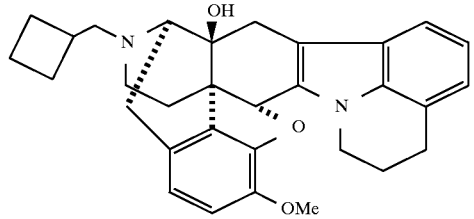

47

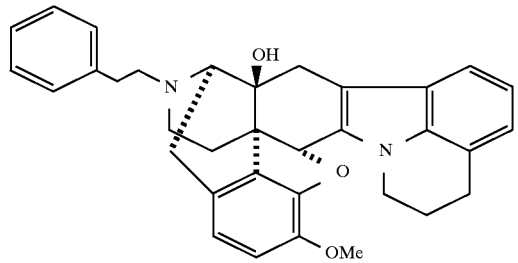

48

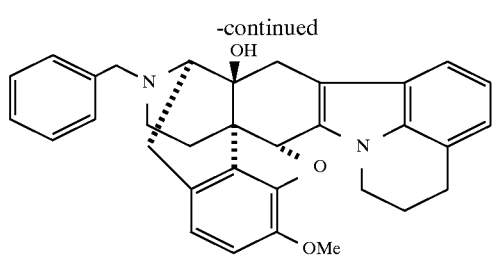

49

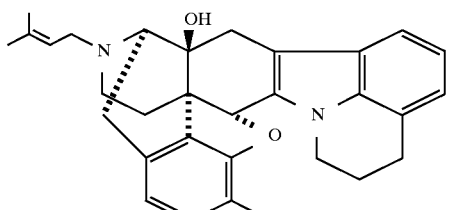

50

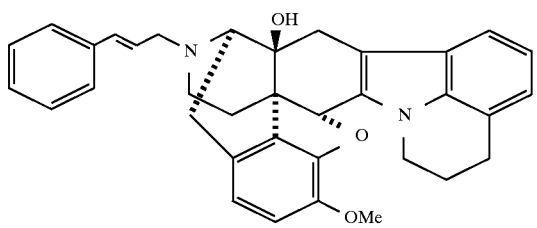

51

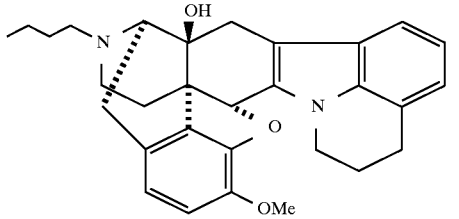

52

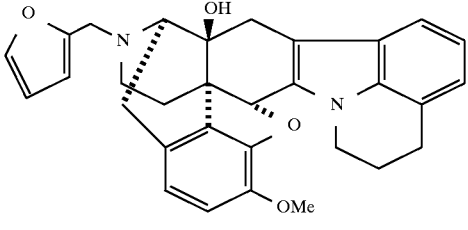

53

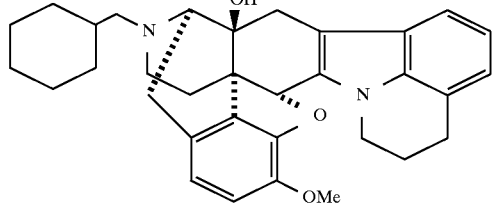

54

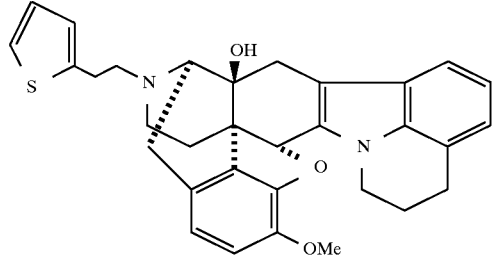

[Example 55]

17-Methyl-6,7-didehydro-4,5α-epoxy-3,14β-dihydroxy-1',7'-trimethylene-6,7,2',3'-indolomorphinan 55 Methanesulfonate

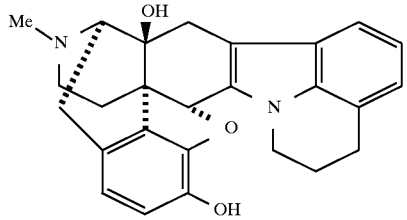

17-Methyl-6,7-didehydro-4,5α(-epoxy-3-methoxy-14β-hydroxy-1',7'-trimethylene-6,7,2',3'-indolomorphinan 45 (170 mg) obtained in Example 45 was dissolved in methylene chloride (8 ml). After a methylene chloride solution of boron tribromide (1.0M, 2.60 ml, 6 equivalent amounts) was added at 0° C., the resulting mixture was warmed to room temperature, and stirred at this temperature for 40 min.

The reaction mixture was then diluted with methylene chloride (30 ml), a saturated sodium hydrogencarbonate solution (30 ml) was added and stirred, and the mixture was subjected to separation. The aqueous phase was subjected to re-extraction with chloroform, and the obtained organic phases were mixed, dried over anhydrous sodium sulfate, and concentrated to obtain a crude product. This crude product was purified by silica gel column chromatography (9385 manufactured by Merck Ltd.; 25 g, chloroform/ammonia-saturated chloroform=8/1→3/1 for a first purification; and 25 g, chloroform/methanol=40/1→25/1 for a second purification) to obtain a free base substance of the object product. This free base substance was dissolved in methanol (3 ml) with the addition of methanesulfonic acid, suspended in ether, and collected by filtration to obtain the object product.

[Examples 56 to 66]

According to the same manner as in Example 55, the following object products:

17-cyclobutylmethyl-6,7-didehydro-4,5α-epoxy-3,14β-dihydroxy-1',7'-trimethylene-6,7,2',3'-indolomorphinan 56 methanesulfonate;

17-phenethyl-6,7-didehydro-4,5α-epoxy-3,14β-dihydroxy-1',7'-trimethylene-6,7,2',3'-indolomorphinan 57 methanesulfonate;

6,7-didehydro-4,5α-epoxy-3,14β-dihydroxy-1',7'-trimethylene-6,7,2',3'-indolomorphinan 58 methanesulfonate;

17-benzyl-6,7-didehydro-4,5α-epoxy-3,14β-dihydroxy-1',7'-trimethylene-6,7,2',3'-indolomorphinan 59 phosphate;

17-prenyl-6,7-didehydro-4,5α-epoxy-3,14β-dihydroxy-1',7'-trimethylene-6,7,2',3'-indolomorphinan 60 methanesulfonate;

17-cinnamyl-6,7-didehydro-4,5α-epoxy-3,14β-dihydroxy- 1',7'-trimethylene-6,7,2',3'-indolomorphinan 61 hydrochloride;

17-butyl-6,7-didehydro-4,5α-epoxy-3,14β-dihydroxy-1',7'-trimethylene-6,7,2',3'-indolomorphinan 62 methanesulfonate;

17-(furan-2-ylmethyl)-6,7-didehydro-4,5α-epoxy-3,14β-dihydroxy-1',7'-trimethylene-6,7,2',3'-indolomorphinan 63 methanesulfonate;

17-cyclohexyl-6,7-didehydro-4,5α-epoxy-3,14β-dihydroxy-1',7'-trimethylene-6,7,2',3'-indolomorphinan 64 hydrochloride;

17-(thiophene-2-ylethyl)-6,7-didehydro-4,5α-epoxy-3,14β-dihydroxy-1',7'-trimethylene-6,7,2',3'-indolomorphinan 65 hydrochloride; and 17-cyclopropylmethyl-6,7-didehydro-4,5α-epoxy-3-hydroxy-14β-methoxy-1',7'-trimethylene-6,7,2',3'-indolomorphinan 66 methanesulfonate were obtained using the following compounds instead of 17-methyl-6,7-didehydro-4,5α-epoxy-3-methoxy-14β-hydroxy-1',7'-trimethylene-6,7,2',3'-indolomorphinan 45, respectively:

17-cyclobutylmethyl-6,7-didehydro-4,5α-epoxy-3-methoxy-14β-hydroxy-1',7'-trimethylene-6,7,2',3'-indolomorphinan 46;

17-phenethyl-6,7-didehydro-4,5α-epoxy-3-methoxy-14β-hydroxy-1',7'-trimethylene-6,7,2',3'-indolomorphinan 47;

6,7-didehydro-4,5α-epoxy-3-methoxy-14β-hydroxy-1',7'-trimethylene-6,7,2',3'-indolomorphinan 29;

17-benzyl-6,7-didehydro-4,5α-epoxy-3-methoxy-14β-hydroxy-1',7'-trimethylene-6,7,2',3'-indolomorphinan 48;

17-prenyl-6,7-didehydro-4,5α-epoxy-3-methoxy-14β-hydroxy-1',7'-trimethylene-6,7,2',3'-indolomorphinan 49;

17-cinnamyl-6,7-didehydro-4,5α-epoxy-3-methoxy-14β-hydroxy-1',7'-trimethylene-6,7,2',3'-indolomorphinan 50;

17-butyl-6,7-didehydro-4,5α-epoxy-3-methoxy-14β-hydroxy-1',7'-trimethylene-6,7,2',3'-indolomorphinan 51;

17-(furan-2-ylmethyl)-6,7-didehydro-4,5α-epoxy-3-methoxy-14β-hydroxy-1',7'-trimethylene-6,7,2',3'-indolomorphinan 52;

17-cyclohexyl-6,7-didehydro-4,5α-epoxy-3-methoxy-14β-hydroxy-1',7'-trimethylene-6,7,2',3'-indolomorphinan 53;

17-(thiophene-2-ylethyl)-6,7-didehydro-4,5α-epoxy-3-methoxy-14β-hydroxy-1',7'-trimethylene-6,7,2',3'-indolomorphinan 54; and 17-cyclopropylmethyl-6,7-didehydro-4,5α-epoxy-3,14β-dimethoxy-1',7'-trimethylene-6,7,2',3'-indolomorphinan 31.

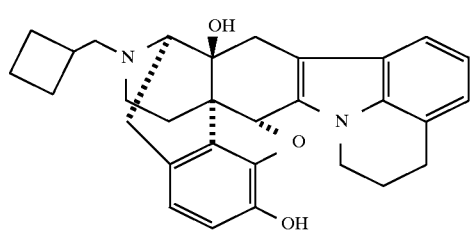

53
-continued
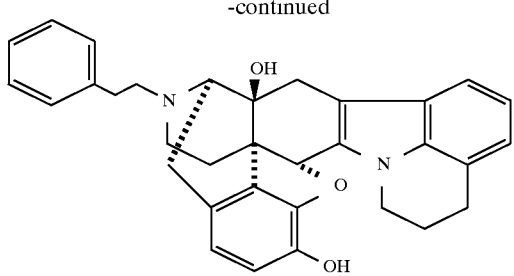
57
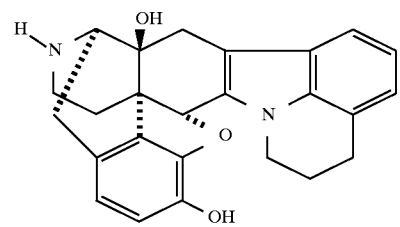
58
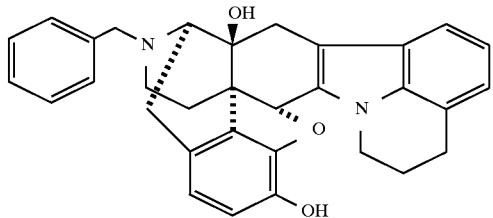
59
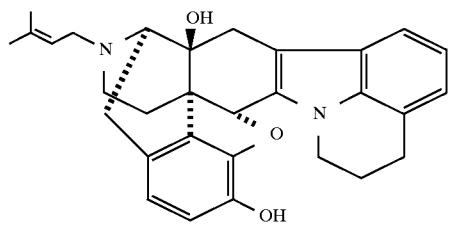
60
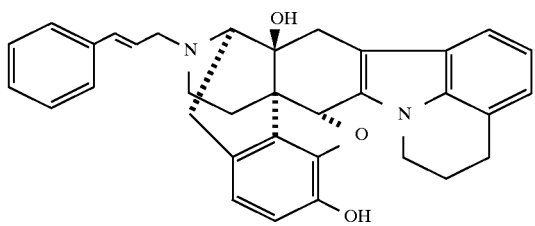
61
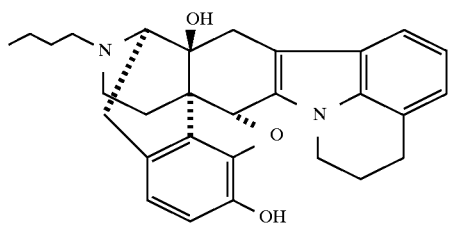
62
54
-continued
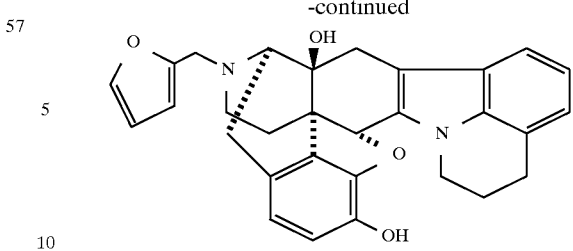
63
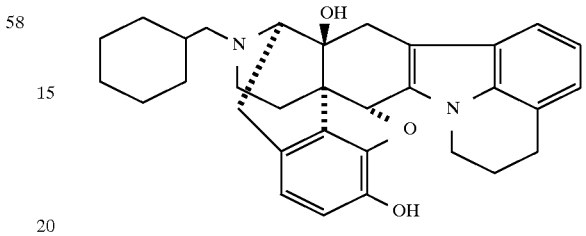
64
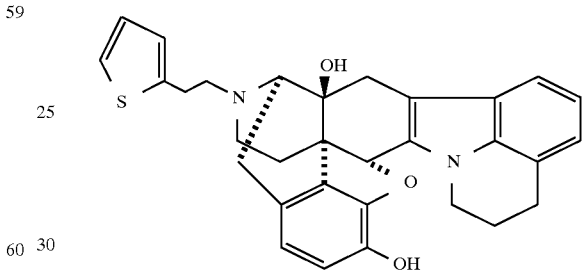
65
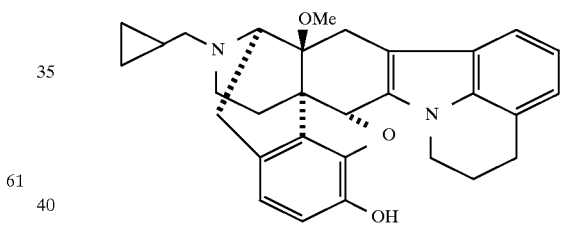
66
Physical properties of the compounds obtained in Examples 1 to 66 are shown in Table 1 below.

TABLE 2

Physical Properties of Example Compounds

| Comp. | % y | mp(°C.) | NMR (δ, ppm) | IR(cm⁻¹) | MS | Elemental anal. |
|---|---|---|---|---|---|---|
| 1 | 49 | 235 (dec) | 0.39–0.53(2H, m), 0.58–0.67(1H, m), 0.68–0.77(1H, m), 1.03–1.13(1H, m), 1.82(1H, br d, J=10.7Hz), 2.29(3H, s), 2.52–2.77(2H, m), 2.60(1H, d, J=16.1Hz), 2.92(1H, br s), 2.95(1H, d, J=15.6Hz), 3.10(1H, br d, J=11.7Hz), 3.20–3.43(2H, m), 3.42(1H, t, J=19.5Hz), 3.76(2H, t, J=6.8Hz), 4.04(1H, d, J=6.4Hz), 4.45–4.54(1H, m), 4.57–4.66(1H, m), 5.81(1H, s), 6.32(2H, s), 6.60(1H, d, J=8.3Hz), 6.62(1H, d, J=8.3Hz), 6.83–6.90(2H, m), 7.09(1H, d, J=6.8Hz), 8.92(1H, br s), 9.20(1H, s) | 3420, 3230, 1620, 1508, 1460, 1195, 1114, 1038, 770 | 441 ((M + H)⁺) FAB | C₂₈H₂₈N₂O₃·CH₃SO₃H·0.4H₂O calc.: C, 64.05; H, 6.08; N, 5.15; S, 5.90. obs.: C, 63.92; H, 6.15; N, 5.32; S, 5.99. |
| 2 | 22 | 237–240 (dec) | 0.40–0.57(2H, m), 0.57–0.70(1H, m), 0.70–0.79(1H, m), 1.04–1.17(1H, m), 1.88(1H, d, J=11.7Hz), 2.34(3.75H, s), 2.56–2.81(3H, m), 2.88–3.00(1H, m), 3.07(1H, d, J=16.1Hz), 3.08–3.17(1H, m), 3.23–3.36(1H, m), 3.36–3.46(2H, m) 3.46–3.59(H, m), 4.10(1H, d, J=6.8Hz), 4.26–4.34(1H, m), 4.54–4.61 (1H, m), 5.99(1H, s), 6.38(1H, br s), 6.60(1H, d, J=8.3Hz), 6.63(1H, d, J=8.3 Hz), 7.40–7.43(3H, m), 7.50(1H, m), 7.747.78(1H, m), 8.96(1.25H, br s), 9.18(1H, s) | 3400, 2878, 1702, 1655, 1636, 1560, 1543, 1510, 1460, 1421, 1402, 1292, 1197, 1118, 1048, 826, 789, 667 | 491 ((M + H)⁺) FAB | C₃₁H₃₀N₂O₃·1.25CH₃SO₃H· 0.9H₂O calc.: C, 63.70; H, 5.92; N, 4.47; S, 6.39. obs.: C, 63.53; H, 5.97; N, 4.67; S, 6.36. |
| 3 | 33 | 260 | 0.41–0.54(2H, m), 0.61–0.67(1H, m), 0.71–0.77(1H, m), 1.06–1.15(1H, m), 1.88(1H, d, J=10.7Hz), 2.31(3.75H, s), 2.59–2.78(3H, m), 2.93–3.02(2H, m), 3.13–3.16(1H, m), 3.24–3.33(1H, m), 3.36–3.48(2H, m), 4.09(1H, d, J=6.3 Hz) 5 66(1H, d, J=16.6Hz), 5.77(1H, d, J=16.6Hz), 5.95(1H, s), 6.38(1H, br s), 6.61–6.65(2H, m), 7.02(1H, dd, J=7.8, 7.3Hz), 7.28(1H, d, J=7.8Hz), 7.35–7.44(3H, m), 7.6(1H, m), 8.02–8.05(1H, m), 8.97(1.25H, br s), 9.20(1H, br s) | 3400, 1736, 1719, 1702, 1686, 1649, 1638, 1620, 1562, 1543, 1510, 1460, 1321, 1116, 1033, 946, 793, 754 | 503 ((M + H)⁺) FAB | C₃₃H₃₀N₂O₃·1.25CH₃SO₃H· 0.6H₂O calc.: C, 64.93; H, 5.76; N, 4.42; S, 6.33. obs.: C, 64.86; H, 5.77; N, 4.59, S, 6.19. |
| 4 | 45 | 210 | 0.39–0.54(2H, m), 0.58–0.67(1H, m), 0.68–0.78(1H, m), 1.03–1.14(1H, m), 1.84(1H, d, J=11.2Hz), 2.09–2.25(2H, m), 2.30(3.6H, s), 2.56(1H, d, J=16.1Hz), 2.56–2.78(2H, m), 2.87–3.00(4H, m), 3.12(1H, br d, J=10.3Hz), 3.26(1H, dd, J=6.6, 19.6Hz), 3.34–3.43(1H, m), 3.43(1H, d, J=19.5Hz), 4.07(1H, d, J=6.4Hz), 4.14–4.23(1H, m), 4.26–4.35(1H, m), 5.90(1H, s), 6.31(1H, br s), 6.60(1H, d, J=8.3Hz), 6.62(1H, d, J=8.3Hz), 6.846.93(2H, m), 7.17(1H, dd, J=2.0, 6.8Hz), 8.93(1H, br s), 9.17(1H, br s) | 3420, 2934, 1649, 1638, 1626, 1620, 1508, 1475, 1460, 1437, 1371, 1325, 1207, 1116, 1044, 777, 551 | 455 ((M + H)⁺) FAB | C₂₉H₃₀N₂O₃·1.2CH₃SO₃H· 0.3H₂O calc.: C, 63.05; H, 6.20; N, 4.87; S, 6.69. obs.: C, 63.12; H, 6.36; N, 4.75; S, 6.62. |
| 5 | 76 | 248 (dec) | 0.40–0.57(2H, m), 0.58–0.79(2H, m), 1.04–1.16(1H, m), 1.84(1H, d, J=12.3 Hz), 2.07–2.22(2H, m), 2.32(3.3H, s), 2.46(3H, s), 2.53–2.67(3H, m), 2.78 (1H, d,J=16.5Hz), 2.84–2.97(2H, m), 3.07–3.16(-1H, m), 3.21–3.32(2H, m), 3.37–3.49(2H, m), 4.06(1H, d, J=6.0Hz), 4. 1 2–4.33(2H, m), 5.88(1H, s), 6.30(1H, br s), 6.58–6.65(3H, m), 6.72(1H, d, J=7.1Hz), 8.97(1.1H, br s), 9.17(1H, br s) | 3400, 2926, 1657, 1562, 1510, 1460, 1433, 1296, 1195, 1116, 1052, 849, 785 | 469 ((M + H)⁺) FAB | C₃₀H₃₂N₂O₃·1.1CH₃SO₃H· 0.65H₂O calc.: C, 63.74; H, 6.48;N, 4.78; S, 6.02. obs.: C, 63.51; H, 6.58; N, 5.06; S, 6.06. |
| 6 | 68 | >230 (dec) | 0.39–0.54(2H, m), 0.58–0.77(2H, m), 1.08(1H, m), 1.83(1H, d, J=12.4Hz), 2.03–2.21(2H, m), 2.29(3H, s), 2.42–2.98(7H, m), 3.10(1H, m), 3.20–3.46 (3H, m), 3.77(3H, s), 4.0–4.13(2H, m), 4.19–4.27(1H, m), 5.85(1H, s), 6.31 (1H, br s), 6.60(2H, m), 6.74(1H, d, J=8.8Hz), 7.14(1H, d, J=8.8Hz), 8.92 (1H, br s), 9.19(1H, br s) | 3400, 1628, 1508, 1247, 1195, 1116, 1052, 785, 561 (KBr) | 485 ((M + H)⁺) FAB | C₃₀H₃₂N₂O₄·CH₃SO₃H·0.8H₂O calc.: C, 62.57; H, 6.37; N, 4.71; S, 5.39. obs.: C, 63.37; H, 6.41; N, 4.86; S, 5.67. |
| 7 | 48 | 205 (dec) | 0.38–0.55(2H, m), 0.57–0.79(2H, m), 1.02–1.16(1H, m), 1.83(1H, d, J=11.3Hz), 2.06–2.24(2H, m), 2.30(3H, s), 2.32(3H, br s), 2.53–2.79(3H, m), 2.84–2.99(4H, m), 3.12(1H, br d, J=10.2Hz), 3.24(1H, m), 3.44(1H, dd, J=6.4, *19.9Hz), 3.32–3.48(1H, m), 3.44(1H, d, J=19.8Hz), 4.06(1H, d, J=6.0Hz), 4.09–4.21(1H, m), 4.22–4.33(1H, m), 5.87(1H, s), 6.3 1(1H, s), 6.60(1H, d, J=8.2Hz), 6.62(1H, d, J=8.2Hz), 6.72(1H, br s), 8.92(1H, br s), 9.21(1H, br s) | 3424, 3226, 2928, 1638, 1620, 1508, 1460, 1435, 1328, 1210, 1195, 1116, 1060, 1044, 864, 785 | 469 ((M + H)⁺) FAB | C₃₀H₃₂N₂O₃·SOH·0.7H₂O calc.: C, 64.50; H, 6.53; N, 4.85; S, 5.55. obs.: C, 64.30; H, 6.59; N, 5.16; S, 5.77. |
| 8 | 78 | 198–202 (dec) | 0.53–0.56(2H, m), 0.75–0.91(2H, m), 1.11–1.15(1H, m), 1.97(1H, dd, J=3.0, 13.5Hz), 2.24–2.29(2H, m), 2.73–2.80(3H, m), 2.89–3.02(4H, m), 3.17(1H, | 3378, 2938, 1640, 1620, 1504, 1435, 1435, | 489 ((M + H)⁺) | C₂₉H₂₉Cl₁N₂O₂·HCl·0.9H₂O calc.: C, 64.30; H, 5.92; Cl, |

TABLE 2-continued

Physical Properties of Example Compounds

| Comp. | % y | mp(°C.) | NMR (δ, ppm) | IR(cm⁻¹) | MS | Elemental anal. |
|---|---|---|---|---|---|---|
| | | | dd, J=4.4, 13.0Hz), 3.30–3.43(3H, m), 4.18–4.86(3H, m), 4.86(2H, br s), 5.84 (1H, s) 6.65–6.70(2H, m), 6.85(1H, s), 7.20(1H, s), 7.32(1H, s) | 1462, 1317, 1296, 1253, 1116, 1060, 1036, 915, 864, 801 (KBr) | FAB | 1309; N, 5.17. obs.: C, 64.56; H, 6.19; Cl, 12.64; N, 5.21. |
| 9 | 67 | 180 (dec) | 0.39–0.55(2H, m), 0.58–0.79(2H, m), 1.01–1.16(1H, m), 1.84(1H, d, J=11.8Hz), 1.92–2.04(2H, m), 2.08–2.19(2H, m), 2.30(3H, s), 2.52–2.80(3H, m), 2.88–2.99(1H, m), 2.94(1H, d, J=16.2Hz), 3.03–3.17(3H, m), 3.26(1H, dd, J=6.9, 19.8Hz), 3.13–3.50(2H, m), 4.08(1H, d, J=6.0Hz), 4, 29(2H, br t, J=5.2Hz), 5.90(1H, s), 6.30(1H, br s), 6.60(1H, d, J=8.2Hz), 6.62(1H, d, J=8.0Hz), 6.85–6.96(2H, m), 7)7(1H, dd, J=1.8, 7.3Hz), 8.93(1H, br s), 9.22(1H, br s) | 3450, 2930, 2862, 1641, 1624, 1507, 1467, 1428 1327, 1193, 1115, 1046 845, 780, 747 | 469 ((M + H)⁺) FAB | C₃₀H₃₂N₂O₃.CH₃SO₃H.0.4H₂O calc.: C, 65.10; H, 6.49; N, 4.90; S, 5.61. obs.: C, 64.95; H, 6.72; N, 5.03; S, 5.71. |
| 10 | 87 | 190–223 (dec) | 0.39–0.54(2H, m), 0.58–0.77(2H, m), 1.09(1H, m), 1.84(1H, d, J=12.6Hz), 2.08–2.24(2H, m), 2.31(4.2H, s), 2.53–2.78(3H, r11), 2.89–2.98(4H, m), 3.11 (1H, m), 3.19–3.28(1H, m), 3.35–3.47(2H, m), 4.06(1H, m), 4.12–4.21(1H, m), 4.26–4.35(1H, m), 5.90(1H, s), 6.32(1H, br s), 6.58–6.65(2H, m), 6.78 (1H, m), 6.19(1H, dd, J=10.2, 2.2Hz), 8.94(1.4H, br s), 9.21(1H, br s) | 3400, 1626, 1493, 1460 1437, 1193, 1046, 557 (KBr) | 473 ((M + H)⁺) FAB | C₂₉H₃₀FN₂O₃.1.4CH₃SO₃H. 0.4H₂O calc.: C, 59.44; H, 5.81; F, 3.09; N, 4.56; S, 7.31. obs.: C, 59.29; H, 5.93; F, 3.01; N, 4.84; S, 7.22. |
| 11 | 82 | 185–205 (dec) | 0.4–0.6(2H, m), 0.62(1H, m), 0.78(1H, m), 1.10(1H, m), 1.86(1H, d, J=10.9 Hz), 2.1–2.3(2H, m), 2.31(3H, s), 2.5–2.8(3H, m), 2.9–3.1(4H, m), 3.13(1H, d, J=10.9Hz), 3.3–3.5(3H, m), 3.70(3H, s), 4.11(1H, m), 4.15(1H, m), 4.35 (1H, m), 5.97(1H, s), 6.37(1H, br), 6.73(1H, d, J=8.4Hz), 6.81(1H, d, J=84 Hz), 6.87(1H, dd, J=6.8, 2.2Hz), 6.91(1H, t, J=6.8Hz), 7.18(1H, dd, J=6.8, 2.2Hz), 8.98(1H, br) | 3400, 1630, 1611, 1508, 1439, 1193, 1123, 1052, 897 (KBr) | 468 (M⁺) (EI) free base | C₃₀H₃₂N₂O₃.CH₃SO₃H.0.7H₂O calc.: C, 64.50; H, 6.63; N, 4.85; S, 5.55. obs.: C, 64.42; H, 6.33; N, 4.91; S, 5.74. |
| 12 | 88 | 198–205 (dec) | 0.40–0.54(2H, m), 0.58–0.78(2H, m), 1.09(1H, m), 1.85(1H, d, J=11.3Hz), 2.03–2.20(2H, m), 2.30(3.3H, s), 2.53–2.99(7H, m), 3.37–3.45(1H, m), 3.25–3.45(3H, m), 3.70(3H, s), 3.77(3H, s), 3.98–4.10(2H, m), 4.20–4.28(1H, m), 5.92(1H, s), 6.35(1H, br), 6.71–6.82(2H, m), 6.75(1H, d, J=8.5Hz), 7.14 (1H, d, J=8.5Hz), 8.96(1, 1H, br s) | 3486, 2926, 1657, 1638, 1510, 1499, 1460, 1439, 1195, 1123, 1050, 895, 783 | 499 (M⁺) (FAB) | C₃₁H₃₄N₂O₄.1.1CH₃SO₃H.H₂O calc.: C, 61.95; H, 6.54; N, 4.50; S, 5.67. obs.: C, 61.61; H, 6.61; N, 4.70; S, 5.97. |
| 13 | 37 | 185 (dec) | 0.39–0.56(2H, m), 0.56–0.80(2H, m), 1.02–1.17(1H, m), 1.85(1H, d, J=11.5Hz), 2.04–2.24(2H, m), 2.30(3.3H, s), 2.32(3H, br s), 2.53–2.79(3H, m), 2.83–3.01(4H, m), 3.12(1H, br d, J=10.4Hz), 3.29(1H, dd, J=6.3, 19.8Hz), 3.30–3.48(1H, m), 3.49(1H, m), 3.70(3H, s), 4.02–4.15(2H, m), 4.23–4.35(1H, m), 5.94(1H, s), 6.35(1H, br s), 6.72(1H, s), 6.73(1H, d, J=8.2Hz), 6.81(1H, d, J=8.2Hz), 6.94(1H, s), 8.95(1H, br s) | 3400, 2930, 1638, 1562, 1510, 1433, 1288, 1197, 1123, 785 | 483 ((M = H)⁺) (FAB) | C₃₁H₃₄N₂O₃.1.1CH₃SO₃H. 0.8H₂O calc.: C, 63.97; H, 6.69; N, 4.65; S, 5.85. obs.: C, 63.09; H, 6.75; N, 4.92; S, 5.94. |
| 14 | 59 | 204–207 (dec) | 0.42–0.55(1H, m), 0.60–0.68(1H, m), 0.70–0.78(1H, m), 1.05–1.16(1H, m), 1.86(1H, d, J=11.3Hz), 2.05–2.19(2H, m), 2.31(3.6H, s), 2.46(3H, s), 2.60–2.98(5H, m), 3.12(1H, d, J=12.1Hz), 3.25–3.45(4H, m), 3.70(3H, br s), 4.05–4.15(3H, m), 4.26–4.34(1H, m), 5.94(1H, s), 6.33(1H, br s), 6.60(1H, d, J=7.4Hz), 6.72(1H, d, J=7.4Hz), 6.74(1H, d, J=8.5Hz), 6.8 1(1H, d, J=8.5 Hz), 8.97(1.2H, br s) | 3486, 3434, 2932, 1637, 1508, 1454, 1427, 1179, 1123, 1050, 894, 784 | 483 ((M = H)⁺) (FAB) | C₃₁H₃₄N₂O₃.1.2CH₃SO₃H. 0.7H₂O calc.: C, 63.34; H, 6.64; N, 4.59; S, 6.30. obs.: C, 63.09; H, 6.75; N, 4.91; S, 6.42. |
| 15 | 56 | 190 (dec) | 0.39–0.56(2H, m), 0.58–6.79(2H, m), 1.01–1.16(1H, m), 1.86(1H, d, J=11.3Hz), 1.92–2.04(2H, m), 2.0–2.19(2H, m), 2.30(3H, s), 2.53–2.79(3H, m), 2.89–3.01(1H, m), 2.95(1H, d, J=16.2Hz), 3.03–3.18(3H, m), 3.31(1H, dd, J=6.5, 19.9Hz), 3.34–3.57(2H, m), 3.70(3H, s), 4.11(1H, d, J=6.0Hz), 4.20–4.38(2H, m), 5.96(1H, s), 6.34(1H, br s), 6.74(1H, d, J=8.2Hz), 6.81(1H, d, J=8.2Hz), 6.85–6.96(2H, m), 7.18(1H, dd, J=1.6, 7.1Hz), 8.97(1H, br s) | 3356, 1628, 1508, 1441, 1209, 1193, 1125, 1052, 785, 561, 536 (KBr) | 483 ((M = H)⁺) (FAB) | C₃₁H₃₄N₂O₃.CH₃SO₃H. 1.5H₂O calc.: C, 63.45; H, 6.82; N, 4.62; S, 5.29. obs.: C, 63.11; H, 6.52; N, 4.72; S, 5.66. |
| 16 | 83 | 185–196 (dec) | 0.40–0.54(2H, m), 0.59–0.78(2H, m), 1.09(1H, m), 1.86(1H, d, J=1 1.8Hz), 2.06–2.23(2H, m), 2.31(3.6H, s), 2.52–2.78(3H, m), 2.91–3.00(4H, m), 3.12 (1H, m), 3.24–3.53(3H, m), 3.70(3H, s), 4.05–4.15(2H, m), 4.28–4.37(1H, m), 5.96(1H, s), 6.38(1H, m), 6.72–6.83(3H, m), 6.93(1H, dd, J=10.2, 2.2 | 3356, 1628, 1508, 1441, 1209, 1193, 1125, 1052, 785, 561, 536 (KBr) | 487 ((M = H)⁺) (FAB) | C₃₀H₃₁FN₂O₃.1.2CH₃SO₃H. 0.8H₂O calc.: C, 60.80; H, 6.12; F, 3.08; N, 4.55; S, 6.24. |

TABLE 2-continued

Physical Properties of Example Compounds

| Comp. | % y | mp(°C.) | NMR (δ, ppm) | IR(cm⁻¹) | MS | Elemental anal. |
|---|---|---|---|---|---|---|
| 17 | 58 | 240 (dec) | 0.42–0.54(2H, m), 0.60–0.70(1H, m), 0.70–0.80(1H, m), 1.04–1.16(1H, m), 1.91(1H, d, J=11.8Hz), 2.31(3.57H, s), 2.58–2.81(3H, m), 2.92–3.03(2H, m), 3.11–3.16(1H, m), 3.28–3.48(3H, m), 3.69(3H, m), 4.12(1H, d, J=5.5Hz), 5.56(1H, d, J=16.8Hz), 5.79(1H, d, J=17.0Hz), 6.01(1H, s), 6.41(1H, br s), 6.76(1H, d, J=8.2Hz), 6.83(1H, d, J=8.5Hz), 7.00–7.05(1H, m), 7.28(1H, d, J=8.0Hz), 7.36–7.45(3H, m), 7.62(1H, d, J=7.1Hz), 8.02–8.05(1H, m), 9.00 (1.19H, m), Hz), 8.97(1.2H, br s) | 3400, 1613, 1502, 1452 1336, 1288, 1178, 1123, 1050, 882, 748 | 516 ((M⁺) (EI) free base | obs.: C, 60.71; H, 6.06; F, 3.06; N, 4.60; S, 6.47. C₃₄H₃₂N₂O₃·1.19CH₃SO₃H·0.8H₂O calc.: C, 65.49; H, 5.99; N, 4.34; S, 5.21. obs.: C, 65.23; H, 5.99; N, 4.64; S, 5.98. |
| 18 | 66 | 186–199 | 0.53(2H, m), 0.75–0.91(2H, m), 1.15(1H, m), 1.95–1.99(1H, m), 2.24(2H, m), 2.66–2.79(3H, m), 2.92–2.97(4H, m), 3.16–3.20(1H, n1), 3.3–3.46(3H, m), 3.77(3H, s), 4.21–4.32(3H, m), 5.86(1H. s), 6.77(1H, d, J=8.52Hz), 6.83 (1H, d, J=8.52Hz), 6.85(1H, s), 7.20(1H, s), | 3390, 2938, 2842, 1632, 1613, 1507, 1435, 1439, 1371, 1334, 1313, 1286, 1235, 1205, 1166, 1122, 1504, 905, 893, 864 (KBr) | 503 ((M + H)⁺) (FAB) | C₃₃H₃₁N₂O₃·0.85HCl·0.4H₂O calc.: C, 66.58; H, 6.08; Cl, 12.12; N, 5.18. obs.: C, 66.53; H, 6.23; Cl, 11.94; N, 5.01. |
| 19 | 75 | 218 (dec) | 0.40–0.53(2H, m), 0.60–0.66(1H, m), 0.69–0.77(1H, m), 1.04–1.12(1H, m), 1.83(1H, d, J=11.2Hz), 2.08–2.22(2H, m), 2.30(3.9H, s), 2.50–2.76(3H, m), 2.86–2.98(4H, m), 3.11(1H, dd, J=20.0, 6.8Hz), 3.17(1H, dd, J=11.7Hz), 3.33–3.47(2H, m), 3.68(3H, s), 4.05(1H, d, J=6.3Hz), 4.11–4.17(1H, m), 4.23–4.30 (1H, m), 5.86(1H, s), 6.30(1H, s), 6.57(1H, m), 6.61(1H, d, J=5.4Hz), 6.65 (1H, d, J=5.4Hz), 6.66–6.68(1H, m), 8.93(1.3H, br s), 9.19(1H, br s). | 3400, 2834, 1620, 1495, 1460, 1437, 1241, 1195, 1116, 1052, 926, 785. | 485 ((M + H)⁺) FAB | C₃₀H₃₂N₂O₄·1.3CH₃SO₃H·0.6H₂O calc.: C, 60.60; H, 6.24; N, 4.52 S, 6.72. obs.: C, 60.60; H, 6.44; N, 4.70; S, 6.52. |
| 20 | 63 | 234 (dec) | 0.42–0.52(2H, m), 0.58–0.78(2H, m), 1.02–1.17(1H, m), 1.84(1H, d, J=12.1Hz), 2.06–2.24(2H, m), 2.31(3.75H, s), 2.51–2.80(3H, m), 2.90–2.99 (4H, m), 3.10–3.17(1H, m), 3.22(1H, dd, J=19.4, 6.6Hz), 3.35–3.48(2H, m), 4.05(1H, d, J=6.9Hz), 4.10–4.23(2H, m), 4.25–4.37(1H, m), 5.91(1H, s), 6.34 (1H, br s), 6.59–6.67(2H, m) 7.03(1H, s), 7.36(1H, s), 8.95(1.25H, br s), 9.23 (1H, br), | 3400, 2928, 1618, 1508, 1485, 1462, 1433, 1367, 1328, 1195, 1116, 1054, 948, 915, 888, 866, 785. | 534 ((M)⁺) EII free | C₂₉H₃₂BrN₂O₃·1.25CH₃SO₃H·0.1H₂O calc.: C, 55.44; H, 5.26; N, 4.27; S, 6.12; Br, 12.19. obs.: C, 55.70; H, 5.49; N, 4.19; S, 5.94; Br, 11.85. |
| 21 | 66 | 225 (dec) | 0.42–0.53(2H, m), 0.60–0.67(1H, m), 0.70–0.76(1H, m), 1.09–1.17(2H, m), 1.26–1.37(1H, m), 1.77–1.98(4H, m), 2.11–2.21(1H, m), 2.30(3.6H, s), 2.56 (1H, d, J=16.1Hz), 2.60–2.75(1H, m), 2.90–3.00(2H, m), 3.07–3.18(2H, m), 3.26(1H, dd, J=13.2, 6.8Hz), 3.35–3.49(4H, m), 4.07(1H, d, J=6.8Hz), 4.50–4.60(1H, m), 4.63–4.74(1H, m), 5.88(1H, s), 6.30(1H, br s), 6.57–6.63(2H, m), 6.82(1H, d, J=6.4Hz), 6.87(1H, dd, J=7.3, 7.3Hz), 7.19(1H, d, J=6.8Hz), 8.92(1.2H, br s), 9.15(1H, br). | 3400, 2900, 1626, 1508, 1458, 1425, 1381, 1328, 1185, 1116, 1044, 930, 913, 868, 835, 781, 746 S, 6.38. | 482 ((M)⁺) EI free | C₃₁H₃₄N₂O₃·1.20CH₃SO₃H·0.4H₂O calc.: C, 63.91; H, 6.60; N, 4.63; S, 6.36. obs.: C, 63.82; H, 6.83; N, 4.70; S, 6.38. |
| 22 | 90 | 212 (dec) | 0.42–0.53(2H, m), 0.60–0.66(1H, m), 0.70–0.76(1H, m), 1.06–1.11(1H, m), 1.86(1H, d, J=11.2Hz), 2.31(3.6H, s), 2.55(1H, d, J=16.1Hz), 2.62(1H, dd, J=13.2, 4.4Hz), 2.67–2.78(1H, m), 2.92–2.98(1H, m), 2.97(1H, d, J=16.1Hz), 3.12(1H, d, J=12.2Hz), 3.26(1H, m, dd, J=19.5, 6.8Hz), 3.31–3.47(4H, m), 4.08 (1H, d, J=6.3Hz), 4.37–4.45(1H, m), 4.60–4.66(1H, m), 5.93(1H, s), 6.34(1H br s), 6.60(1H, d, J=8.3Hz), 6.63(1H, d, J=8.3Hz), 6.92–6.97(2H, m), 7.15–7.18(1H, m), 8.94(1.2H, br s), 9.20(1H, br). | 3400, 2926, 1626, 1508, 1468, 1425, 1373, 1328, 1276, 1181, 1116, 1060, 948, 901, 859, 777, 743 | 472 ((M)⁺) EI free | C₂₈H₂₈N₂O₃S·1.20CH₃SO₃H·0.5H₂O calc.: C, 58.75; H, 5.71; N, 4.69; S, 11.82. obs.: C, 58.69; H, 5.91; N, 4.63; S, 11.72. |
| 23 | 79 | 240 (dec) | 0.41–0.54(2H, m), 0.57–0.79(2H, m), 1.03–1.15(1H, m), 1.86(1H, d, J=11.5Hz), 2.31(3.6H, s), 2.51–2.79(3H, m), 2.91–3.00(2H, m), 3.12(1H, d, J=11.8Hz), 3.21–3.30(1H, m), 3.34–3.48(3H, m), 4.08(1H, d, J=6.9Hz), 4.23–4.30(1H, m), 4.44–4.49(1H, m), 4.52–4.60(1H, m), 5.90(1H, s), 6.37(1H, br s), 6.56–6.65(3H, m), 6.83–6.89(1H, m), 6.95(1H, d, J=7.9Hz), 8.96(1.2H, br s), 9.20(1H, br). | 3400, 1636, 1584, 1506, 1460, 1435, 1383, 1325, 1270, 1245, 1197, 1116, 1060, 1009, 948, 913, 888, 872, 839, 785, 733 | 456 ((M)⁺) EI free | C₂₈H₂₈N₂O₄·1.20CH₃SO₃H·0.1H₂O calc.: C, 61.14; H, 5.80; N, 4.88; S, 6.71. obs.: C, 61.15; H, 5.97; N, 4.97 S, 6.41. |
| 24 | 93 | 253 | 0.40–0.57(2H, m), 0.60–0.78(2H, m), 1.08–1.19(1H, m), 1.86(1H, d, | 3400, 2928, 1620, | 522 | C₃₀H₂₉F₃N₂O₃·1.20CH₃SO₃H |

TABLE 2-continued

Physical Properties of Example Compounds

| Comp. | % y | mp(°C.) | NMR (δ, ppm) | IR (cm$^{-1}$) | MS | Elemental anal. |
|---|---|---|---|---|---|---|
| 25 | 99 | 242 (dec) | 0.40–0.55(2H, m), 0.59–0.79(2H, m), 1.02–1.13(1H, m), 1.32(3H, s), 1.34 (3H, s), 1.85(1H, d, J=11.3Hz), 1.97–2.00(2H, m), 2.30(3.6 H, s), 2.53–2.80 (3H, m), 2.88–2.98(2H, m), 3.09–3.14(1H, m), 3.21–3.48(3H, m), 4.07(1H, d J=6.9Hz), 4.22–4.30(2H, m), 5.9(1H, s), 6.32(1H, br s), 6.58–6.64(2H, m), 6.92–6.97(1H, m), 7.05(1H, d, J=6.6Hz), 7.18(1H, d, J=7.7Hz), 8.94(1.2H, br s), 9.22(1H, br). | 3400, 2930, 1626, 1508, 1464, 1433, 1365, 1296, 1178, 1116, 1052, 1013, 948, 915, 857, 833, 785, 745. | 482 (((M)$^+$) EI free | $C_{31}H_{44}N_2O_3 \cdot 1.2CH_3SO_3H$ $0.2H_2O$ calc.: C, 64.29; H, 6.57; N, 4.66; S, 6.40. obs.: C, 64.41; H, 6.61; N, 4.84 S, 6.23. |
| 26 | 82 | 231–234 (dec) | 0.40–0.57(2H, m), 0.59–0.80(2H, m), 1.04(3H, s), 1.05(3H, s), 1.06–1.15(1H, m), 1.84(1H, d, J=11.8Hz), 2.31(3.45H, s), 2.53–2.73(5H, m), 2.92–3.02(2H, m), 3.10–3.18(1H, m), 3.21–3.47(3H, m), 3.90–3.99(2H, m), 4.80(1H, d J=5.2Hz), 5.89(1H, s), 6.33(1H, br s), 6.56–6.63(2H, m), 6.86–6.93(2H, m), 7.18(1H, dd, J=7.1, 1.4Hz), 8.94(1.15H, br s), 9.14(1H, br). | 3400, 2964, 1638, 1460, 1433, 1371, 1197, 1116, 1050, 864, 845, 772, 748 | 482 (((M)$^+$) EI free | $C_{31}H_{44}N_2O_3 \cdot 1.15CH_3SO_3H$. $0.4H_2O$ calc.: C, 64.32; H, 6.61; N, 4.67; S, 6.14. obs.: C, 64.11; H, 6.89; N, 4.68; S, 6.15. |
| 27 | 92 | 230 (dec) | 0.41–0.55(2H, m), 0.58–0.78(2H, m), 1.04–1.16(1H, m), 1.82(1H, d, J=11.5Hz), 2.02–2.23(2H, m), 2.32(3.9H, s), 2.54–2.76(3H, m), 2.82–2.95 (3H, m), 3.09(1H, d, J=12.4Hz), 3.20–3.45(4H, m), 3.75(3H, s), 4.06(1H, d J=6.0Hz), 4.11–4.19(1H, m), 4.21–4.30(1H, m), 5.86(1H, d, J=8.2Hz), 6.25(1H, br), 6.33(1H, d, J=7.7Hz), 6.59(1H, d, J=8.2Hz), 6.63(1H, d, J=8.2Hz), 6.75(1H, d, J=7.9Hz), 8.90(1.3H, br s), 9.20(1H, br). | 3400, 1620, 1514, 1462, 1433, 1373, 1296, 1257, 1178, 1116, 1048, 909, 845, 783 | 484 (((M)$^+$) EI free | $C_{30}H_{32}N_2O_4 \cdot 1.30CH_3SO_3H$. $0.15H_2O$ calc.: C, 61.41; H, 6.17; N, 4.58 S, 6.81. obs.: C, 61.15; H, 6.41; N, 4.82; S, 6.86. |
| 28 | 53 | 197 (dec) | 1.84(m, 1H), 2.08–2.26(m, 2H), 2.27–2.45(m, 1H), 2.33(s, 3.30H), 2.45–2.71 (m, 4H), 2.79(ddd, J=3.7, 13, 13Hz, 1H), 2.86–2.99(m, 3H), 3.08–3.30(m, 3H), 3.35–3.50(m, 1H), 3.86(d, J=6.8Hz, 1H), 4.13–4.24(m, 1H), 4.24–4.34 (m, 1H), 5.18(m, 1H), 5.27(dd, J=1.2, 17Hz, 1H), 5.76–5.89(m, 1H), 5.89(s, 1H), 6.59–6.66(m, 2H), 6.85–6.94(m, 2H), 7.17(dd, J=1.5, 6.8Hz, 1H). | 3398, 2938, 1642, 1508, 1477, 1460, 1437, 1371, 1328, 1301, 1207, 1116, 1046, 785, 748, 561, 545, 532, 4143. | 455 ((M + H)$^+$) FAB free | $C_{29}H_{30}N_2O_3 \cdot 1.10CH_3SO_3H$ $0.50H_2O$ calc.: C 63.51; H 6.27; N 4.92; S 6.20. obs.: C 63.33; H 6.34; N 4.82; S 6.37. |
| 29 | 67 | 170 (dec) | 1.81(m, 1H), 2.08–2.24(m, 2H), 2.34(s, 3.72H), 2.49(d, J=16Hz, 1H), 2.56 (ddd, J=5.1, 13, 13Hz, 1H), 2.73(ddd, J=4.3, 13, 13Hz, 1H), 2.89–2.94(m, 3H), 3.12(dd, J=4.7, 13Hz, 1H), 3.19(d, J=20Hz, 1H), 3.41(dd, J=6.9, 20Hz 1H), 3.70(s, 3H), 3.83(d, J=6.7Hz, 1H), 4.09–4.15(m, 1H), 4.27–4.33(m, 1H), 5.91(s, 1H), 6.76(d, J=8.2Hz, 1H), 6.80(d, J=8.2Hz, 1H), 6.86–6.92(m, 2H), 7.16–7.19(m, 1H). | 3388, 2944, 1636, 1609, 1508, 1454, 1199, 1127, 785, 563. | 415 ((M + H)$^+$) FAB free | $C_{26}H_{26}N_2O_3 \cdot 1.24CH_3SO_3H$ $0.20H_2O$ calc.: C 60.90; H 5.88; N 5.21; S 7.40. obs.: C 60.68; H 5.98; N 5.26; S 7.55. |
| 30 | 77 | 190 (dec) | 1.87(m, 1H), 2.10–2.24(m, 2H), 2.34(s, 3.42H), 2.48–2.49(m, 1H), 2.60(ddd, J=4.8, 13, 13Hz, 1H), 2.77(ddd, J=3.8, 13, 13Hz, 1H), 2.90(d, J=16Hz, 1H), 2.90–2.96(m, 3H), 3.13–3.23(m, 1H), 3.40–3.52(m, 1H), 3.71(d, J=6.8Hz, 1H), 3.80(dd, J=5.1, 13Hz, 1H), 3.79–4.04(m, 1H), 3.96–4.03(m, 1H), 4.15– 4.21(m, 1H), 4.26–4.33(m, 1H), 5.58(m, 1H), 5.65(m (m 1H), 5.87–5.97(m, 1H), 5.90(s, 1H), 6.62(d, J=8.1Hz, 1H), 6.64(d, J=8.3Hz, 1H), 6.85–6.92(m, 2H). | 3390, 2942, 1642, 1620, 1508, 1460, 1437, 1203, 1164, 1114, 1064, 1015, 775, 750. | 441 ((M + H)$^+$) FAB free | $C_{28}H_{28}N_2O_3 \cdot 1.14CH_3SO_3H$ $0.70H_2O$ calc.: C 62.20; H 6.08; N 4.98; S 6.50. obs.: C 61.94; H 6.07; N 5.01; S 6.68. |
| 31 | 52 | 209–211 (dec) | 0.44–0.49(1H, m), 0.53–0.59(1H, m), 0.61–0.68(1H, m), 0.75–0.79(1H, m), 1.06–1.15(1H, m), 1.88(1H, d, J=11.2Hz), 2.13–2.20(2H, m), 2.30(3H, s), 2.39(1H, d, J=16.6Hz), 2.45–2.63(2H, m), 2.71–2.79(1H, m), 2.78–2.95(3H, m) 3.16(3H, s), 3.23–3.32(2H, m), 3.49–3.59(2H, m), 3.70(3H, s), 4.08–4.14 (1H, m), 4.30–4.36(1H, m), 4.54(1H, d, J=6.4Hz), 6.09(1H, s), 6.76(1H, d, J=8.3Hz), 6.83(1H, d, J=8.3Hz), 6.87–6.93(2H, m), 7.19–7.22(1H, m), 8.61 (1H, br s). | 3400, 2940, 2840, 1636, 1510, 1454, 1371, 1319, 1286, 1210, 1052, 982, 895, 861, 783, 748. | 482 (((M)$^+$) EI free | $C_{31}H_{34}N_2O_3 \cdot CH_3SO_3H \cdot H_2O$ calc.: C, 64.41; H, 6.76; N, 4.69; S, 5.37. obs.: C, 64.44; H, 6.67; N, 4.64; S, 5.53. |

TABLE 2-continued

Physical Properties of Example Compounds

| Comp. | % y | mp(°C.) | NMR (δ, ppm) | IR(cm⁻¹) | MS | Elemental anal. |
|---|---|---|---|---|---|---|
| 32 | 92 | 170 (dec) | 1.86(m, 1H), 2.07–2.27(m, 2H), 2.27–2.46(m, 1H), 2.33(s, 3.60H), 2.46–2.71 (m, 2H), 2.77(ddd, J=3.6, 13, 13Hz, 1H), 2.86–2.98(m, 3H), 3.08–3.22(m, 3H), 3.40–3.51(m, 2H), 3.70(s, 3H), 3.88(d, J=6.0Hz, 1H), 4.06–0.17(m, 1H), 4.26–4.36(m, 1H), 5.18(dd, J=1.5, 10Hz, 1H), 5.27(dd, J=1.4, 17Hz, 1H), 5.76–5.88(m, 1H), 5.95(s, 1H), 6.75(d, J=8.3Hz, 1H), 6.81(d, J=8.3Hz, 1H), 6.85–6.94(m, 2H), 7.17(dd, J=2.0, 6.8Hz, 1H). | 3444, 3410, 2936, 1638, 1618, 1508, 1452, 1286, 1207, 1123, 1050, 785, 561, 536, 441, 431, 418, 402 | 469 ((M+H)⁺) FAB free | C₃₀H₃₂N₂O₃·1.1CH₃SO₃H 1.0H₂O calc.: C 62.26; H 6.50; N 4.65; S 6.39. obs.: C 62.40; H 6.41; N 4.56; S 6.42. |
| 33 | 77 | 195–197 (dec) | 0.42–0.53(2H, m), 0.60–0.67(1H, m), 0.70–0.77(1H, m), 1.05–1.13(1H, m), 1.85(1H, d, J=12.7Hz), 2.09–2.21(2H, m), 2.31(3.6H, s), 2.54–2.75(3H, m), 2.88–2.99(4H, m), 3.12(1H, d, J=11.7Hz), 3.25–3.43(2H, m), 3.49(1H, d, J=19.5Hz), 3.68(3H, s), 3.70(3H, s), 4.05–4.11(2H, m), 4.25–4.31(1H, m), 5.93(1H, s), 6.34(1H, br s), 6.57(1H, d, J=1.96Hz), 6.65(1H, d, J=1.96Hz), 6.73(1H, d, J=8.3Hz), 6.81(1H, d, J=8.3Hz). | 3400, 2936, 1624, 1497, 1439, 1288, 1203, 1123, 1050, 978, 930, 893, 864, 774, 750. | 498 ((M)⁺) EI free | C₃₁H₃₄N₂O₄·1.2CH₃SO₃H 1.9H₂O calc.: C, 59.67; H, 6.62; N, 4.32; S, 5.94. obs.: C, 59.75; H, 6.31; N, 4.21; S, 6.01. |
| 34 | 86 | 190 (dec) | 1.89(m, 1H), 2.08–2.24(m, 2H), 2.33(s, 3.15H), 2.48–2.56(m, 1H), 2.61(ddd J=4.9, 13, 13Hz, 1H), 2.75(ddd, J=3.6, 13, 13Hz, 1H), 2.88–2.98(m, 3H), 3.15–3.28(m, 2H), 3.53(d, J=20Hz, 1H), 3.70(s, 3H), 3.73(d, J=6.8Hz, 1H), 3.81(dd, J=4.9, 13Hz, 1H), 3.79–4.04(m, 1H), 4.09–4.15(m, 1H), 4.28–4.34 (m, 1H), 5.59(m, 1H), 5.66(m 1H), 5.88–5.98(m, 1H), 5.96(s, 1H), 6.75(d, J=8.1Hz, 1H), 6.82(d, J=8.3Hz, 1H), 6.86–6.92(m, 2H), 7.16(d, J=7.1Hz, 1H). | 3400, 2936, 1636, 1613, 1508, 1441, 1174, 1120, 1044, 897, 777, 748, 557. | 455 ((M+H)⁺) FAB free | C₂₉H₃₀N₂O₃·1.05CH₃SO₃H 0.20H₂O calc.: C 64.56; H 6.24; N 5.01; S 6.02. obs.: C 64.62; H 6.33; N 5.12; S 5.90. |
| 35 | 73 | 220–222 (dec) | 0.41–0.54(2H, m), 0.60–0.67(1H, m), 0.70–0.77(1H, m), 1.07–1.18(1H, m), 1.87(1H, d, J=12.7Hz), 2.08–2.26(2H, m), 2.29(3H, s), 2.52–2.76(3H, m), 2.90–2.99(4H, m), 3.13(1H, d, J=12.2Hz), 3.24–3.31(1H, m), 3.38–3.45(1H, m), 3.50(1H, d, J=20.0Hz), 3.35(3H, s), 4.06–4.14(2H, m), 4.30–4.36(1H, m), 5.97(1H, s), 6.36(1H, br s), 6.74(1H, d, J=8.3Hz), 6.82(1H, d, J=8.3Hz), 7.04 (1H, d, J=1.5Hz), 7.35(1H, d, J=1.5Hz), 8.96(1H, br s). | 3400, 2934, 1636, 1613, 1510, 1485, 1437, 1367, 1315, 1286, 1199, 1122, 1044, 978, 903, 864, 785. | 547 ((M+H)⁺) FAB | C₃₁H₃₁BrN₂O₃·CH₃SO₃H 0.3H₂O calc.: C, 57.37; H, 5.53; N, 4.32; S, 4.94; Br; 12.31. obs.: C, 57.23; H, 5.63; N, 4.23; S, 5.04; Br; 12.42. |
| 36 | 72 | 218–220 (dec) | 0.41–0.55(2H, m), 0.60–0.79(2H, m), 1.04–1.16(1H, m), 1.88(1H, d, J=12.1Hz), 2.31(3.3H, s), 2.58–2.78(3H, m), 2.92–3.02(2H, m), 3.01–3.17 (1H, m), 3.26–3.44(4H, m), 3.50(1H, d, J=19.8Hz), 3.70(3H, s), 4.11(1H, d, J=6.3Hz), 4.28–4.38(1H, m), 4.62–4.71(1H, m), 6.00(1H, s), 6.40(1H, br s), 6.74(1H, d, J=8.2Hz), 6.82(1H, d, J=8.5Hz), 6.94–6.98(2H, m), 7.17(1H, dd, J=6.6, 2.5Hz), 9.00(1H, br s). | 3400, 2918, 1636, 1611, 1508, 1437, 1377, 1330, 1284, 1180, 1122, 1042, 946, 893, 857, 775, 739 | 486 ((M)⁺) EI free | C₂₉H₃₀N₂O₃S·1.1CH₃SO₃H 0.4H₂O calc.: C, 60.30; H, 5.92; N, 4.67; S, 11.23. obs.: C, 60.55; H, 5.98; N, 4.70; S, 10.94. |
| 37 | 82 | 222–225 | 0.40–0.56(2H, m), 0.60–0.79(2H, m), 1.05–1.20(2H, m), 1.22–1.38(1H, m), 1.75–1.89(3H, m), 1.90–2.18(2H, m), 2.58–2.75(3H, m), 2.94–3.07(2H, m), 3.08–3.20(2H, m), 3.25–3.40(3H, m), 3.49(1H, d, J=20.0Hz), 3.68(3H, s), 4.12–4.18(1H, m), 4.52–4.72(2H, m), 5.95(1H, s), 6.45(1H, br s), 6.72(1H, d, J=8.5Hz), 6.79–6.90(3H, m), 7.18(1H, dd, J=7.4, 1.4Hz), 9.04(1H, br). | 3400, 2922, 1609, 1508, 1456, 1340, 1284, 1183, 1122, 1054, 895, 866, 832, 783, 746 | 496 ((M)⁺) EI free | C₃₀H₃₆N₂O₃·HCl.0.3H₂O calc.: C, 71.37; H, 7.04; N, 5.20; Cl, 6.58. obs.: C, 71.26; H, 7.19; N, 5.29; Cl, 6.53. |
| 38 | 76 | 214–216 (dec) | 0.41–0.56(2H, m), 0.59–0.79(2H, m), 1.03–1.15(1H, m), 1.87(1H, d, J=11.3Hz), 2.31(3.45H, s), 2.53–2.78(3H, m), 2.92–3.01(2H, m), 3.09–3.18 (1H, m), 3.26–3.42(2H, m), 3.50(1H, d, J=19.8Hz), 3.70(3H, s), 4.10(1H, d, J=6.3Hz), 4.16–4.24(1H, m), 4.42–4.51(2H, m), 4.55–4.61(1H, m), 5.96(1H, s), 6.40(1H, br s), 6.58(1H, d, J=7.4Hz), 6.74(1H, d, J=8.2Hz), 6.82(1H, d, J=8.2Hz), 6.87(1H, d, J=7.4, 7.4Hz), 6.95(1H, d, J=7.4Hz), 8.98(1.15H, br s). | 3400, 1636, 1586, 1506, 1444, 1383, 1286, 1245, 1193, 1122, 1052, 1000, 944, 901, 835, 785, 733 | 470 ((M)⁺) EI free | C₂₉H₃₀N₂O₄·1.15CH₃SO₃H 0.7H₂O calc.: C, 61.00; H, 6.11; N, 4.72; S, 6.21. obs.: C, 61.04; H, 6.10; N, 4.67; S, 6.14. |
| 39 | 59 | 207–210 (dec) | 0.42–0.56(2H, m), 0.61–0.80(2H, m), 1.10–1.20(1H, m), 1.88(1H, d, J=11.3Hz), 2.20–2.28(2H, m), 2.30(3H, s), 2.52–2.78(3H, m), 2.78–2.95(1H, m), 3.00–3.19(5H, m), 3.30(1H, dd, J=20.0, 6.3Hz), 3.42–3.47(1H, m), 3.70 (3H, s), 4.13(1H, d, J=6.3Hz), 4.15–4.22(1H, m), 4.39–4.47(1H, m), 6.04(1H, s), 6.42(1H, br s), 6.76(1H, d, J=8.2Hz), 6.83(1H, d, J=8.2Hz), 7.04(1H d, J=7.7Hz), 7.31(1H, d, J=7.7Hz), 8.94(1H, br s). | 3400, 2936, 1638, 1510, 1437, 1388, 1330, 1299, 1195, 1118, 1052, 901, 843, 812, 785, 748. | 536 ((M)⁺) EI free | C₃₁H₃₁F₃N₂O₃·CH₃SO₃H 0.6H₂O calc.: C, 59.73, H, 5.67; F, 8.86; N, 4.35; S, 4.98. obs.: C, 59.29; H, 5.93; F, 8.59; N, 4.55; S, 5.15. |

TABLE 2-continued

Physical Properties of Example Compounds

| Comp. | % y | mp(°C.) | NMR (δ, ppm) | IR (cm⁻¹) | MS | Elemental anal. |
|---|---|---|---|---|---|---|
| 40 | 85 | 207–211 (dec) | 0.41–0.55(2H, m), 0.60–0.80(2H, m), 1.05–1.16(1H, m), 1.31(3H, s), 1.34 (3H, s), 1.87(1H, d, J=10.7Hz), 1.96–2.01(2H, m), 2.31(3.45H, s), 2.53–2.78 (3H, m), 2.91–3.00(2H, m), 3.12(1H, d, J=9.3Hz), 3.26–3.42(2H, m), 3.50 (1H, d, J=19.8Hz), 3.70(3H, s), 4.10(1H, d, J=7.9Hz), 4.17–4.23(1H, m), 4.27–4.35(1H, m), 5.98(1H, br s), 6.36(1H, d, J=8.2Hz), 6.74(1H, d, J=8.2Hz), 6.81(1H, d, J=8.5Hz), 6.92–6.97(1H, m), 7.06(1H, d, J=6.6Hz), 7.18(1H, d, J=7.7Hz), 8.98 (1.15H, br s). | 3400, 2920, 1636, 1611, 1508, 1454, 1363, 1286, 1195, 1123, 1054, 948, 893, 857, 785, 748. | 496 ((M)⁺) EI free | $C_{32}H_{36}N_2O_3 \cdot 1.15CH_3SO_3H \cdot 0.4H_2O$ calc.: C, 64.81; H, 6.79; N, 4.56; S, 6.00. obs.: C, 64.50; H, 6.96; N, 4.57; S, 6.15. |
| 41 | 44 | 199–203 (dec) | 0.41–0.54(2H, m), 0.60–0.78(2H, m), 1.04–1.13(1H, m), 1.84(1H, d, J=11.8Hz), 2.30(3H, s), 2.55–2.77(3H, m), 2.91–3.00(2H, m), 3.11(1H, d, J=10.7Hz), 3.25–3.52(3H, m), 3.70(3H, s), 3.73–3.78(2H, m), 4.07(1H, d, J=6.6Hz), 4.43–4.51(1H, m), 4.58–4.67(1H, m), 5.87(1H, s), 6.38(1H, br s), 6.73(1H, d, J=8.5Hz), 6.82(1H, d, J=8.5Hz), 6.86–6.90(2H, m), 7.08(1H, dd, J=6.6, 1.9Hz), 8.96(1H, br s). | 3400, 2916, 1638, 1508, 1444, 1379, 1332, 1284, 1195, 1122, 1052, 953, 893, 843, 770. | 454 ((M)⁺) EI free | $C_{27}H_{30}N_2O_3 \cdot CH_3SO_3H \cdot 0.5H_2O$ calc.: C, 64.38; H, 6.30; N, 5.01; S, 5.73. obs.: C, 64.30; H, 6.43; N, 4.99; S, 5.92. |
| 42 | 36 | 250 (dec) | 0.40–0.55(2H, m), 0.59–0.77(2H, m), 1.05–1.17(1H, m), 1.87(1H, d, J=10.7Hz), 2.57–2.73(3H, m), 2.91–3.01(1H, m), 3.07–3.13(1H, m), 3.26–3.43 (2H, m), 3.46–3.55(3H, m), 3.66(3H, s), 4.13–4.27(2H, m), 4.53–4.62(1H, m), 6.03(1H, s), 6.49(1H, s), 6.72(1H, d, J=8.5Hz), 6.79(1H, d, J=8.5Hz), 7.37–7.41(3H, m), 7.48(1H, d, J=8.5Hz), 7.72–7.76(1H, m), 9.03(0.9H, br s). | 3400, 2906, 1636, 1508, 1406, 1336, 1284, 1191, 1122, 1050, 967, 948, 891, 859, 822, 797. | 504 ((M)⁺) EI free | $C_{33}H_{32}N_2O_3 \cdot 0.9HCl \cdot 0.4H_2O$ calc.: C, 72.77; H, 6.24; N, 5.14; Cl, 5.86. obs.: C, 72.72; H, 6.38; N, 5.26; Cl, 5.83. |
| 43 | 78 | 192–195 (dec) | 0.41–0.58(2H, m), 0.60–0.79(2H, m), 1.03(3H, s), 1.05(3H, s), 1.05–1.16 (1H, m), 1.86(1H, d, J=10.7Hz), 2.32(3.75H, s), 2.55–2.79(5H, m), 2.94–3.05 (2H, m), 3.10–3.19(1H, m), 3.26–3.45(2H, m), 3.49(1H, d, J=20Hz), 3.69(3H, s), 3.86(1H, d, J=11.5Hz), 3.97(1H, d, J=12.0Hz), 4.10(1H, d, J=5.5Hz), 5.95 (1H, s), 6.35(1H, br s), 6.72(1H, d, J=8.2Hz), 6.80(1H, d, J=8.2Hz), 6.86–6.94 (2H, m), 7.18(1H, d, J=7.4Hz), 8.99(1.25H, br s). | 3400, 2936, 1636, 1508, 1444, 1284, 1191, 1123, 1050, 895, 868, 841, 770, 748. | 496 ((M)⁺) EI free | $C_{32}H_{36}N_2O_3 \cdot 1.25CH_3SO_3H \cdot 0.4H_2O$ calc.: C, 64.00; H, 6.75; N, 4.49; S, 6.42. obs.: C, 63.91; H, 6.83; N, 4.58; S, 6.53. |
| 44 | 68 | 220–222 (dec) | 0.40–0.55(2H, m), 0.56–0.79(2H, m), 1.03–1.17(1H, m), 1.83(1H, d, J=10.7Hz), 2.05–2.19(2H, m), 2.29(3H, s), 2.55–2.72(3H, m), 2.81–2.95(3H, m), 3.08(1H, d, J=9.9Hz), 3.23(1H, d, J=17.0Hz), 3.30–3.49(3H, m), 3.69 (3H, s), 3.74(3H, s), 4.01–4.09(2H, m), 4.22–4.31(1H, m), 5.91(1H, s), 6.31 (1H, s), 6.33(1H, d, J=8.0Hz), 6.71(1H, d, J=8.2Hz), 6.74(1H, d, J=8.2Hz) 6.79(1H, d, J=8.5Hz), 8.92(1H, br s). | 3400, 2912, 1636, 1514, 1437, 1375, 1286, 1257, 1155 1122, 1050, 978, 953, 895, 843, 783 | 498 ((M)⁺) EI free | $C_{31}H_{34}N_2O_4 \cdot CH_3SO_3H \cdot 0.4H_2O$ calc.: C, 63.85; H, 6.50; N, 4.65; S, 5.33. obs.: C, 63.71; H, 6.54; N, 4.80; S, 5.31. |
| 45 | 77 | 130 (dec) | 1.81–1.89(m, 1H), 2.02–2.26(m, 2H), 2.34(s, 3.90H), 2.43–2.66(m, 2H), 2.69–2.81(m, 1H), 2.85–2.96(m, 6H), 3.11–3.19(m, 1H), 3.27(dd, J=6.6, 20 Hz, 1H), 3.40–3.60(m, 1H), 3.70(s, 3H), 3.80(d, J=6.7Hz, 1H), 4.07–4.16(m, H), 4.27–4.35(m, 1H), 5.94(s, 1H), 6.76(d, J=8.2Hz, 1H), 6.81(d, J=8.2Hz, 1H), 6.85–6.93(m, 2H), 7.19(dd, J=1.8, 7.0Hz, 1H). | 3410, 2936, 1638, 1508, 1454, 1197, 1060, 899. | 428 ((M)⁺) EI free | $C_{27}H_{36}N_2O_3 \cdot 1.30CH_3SO_3H \cdot 0.80H_2O$ calc.: C 59.86; H 6.18; N 4.93; S 7.34. obs.: C 59.94; H 6.13; N 5.01; S 7.37. |
| 46 | 59 | 147 (dec) | 1.78–2.00(m, 5H), 2.00–2.25(m, 4H), 2.34(s, 4.5 H), 2.23–2.55(m, 4H), 2.61 (ddd, J=4,4, 14, 14.1Hz, 1H), 2.66–2.79(m, 2H), 2.88–2.95(m, 3H), 3.05–3.16 (m, 2H), 3, 27(ddd, J=7.0, 20Hz, 1H), 3.37–3.53(m, 2H), 3.63(d, J=6.4Hz, 1H), 3.70(s, 3H), 4.07–4.16(m, 1H), 4.26–4.36(m, 1H), 5.94(s, 1H), 6.75(d, J=8.4Hz, 1H), 6.81(d, J=8.8Hz, 1H), 6.85–6.93(m, 2H), 7.17(dd, J=1.8, 6.1 Hz, 1H). | 3446, 2938, 1636, 1613, 1508, 1454, 1212, 1122, 1060, 895, 563. | 482 ((M)⁺) EI free | $C_{31}H_{34}N_2O_3 \cdot 1.50CH_3SO_3H \cdot 0.40H_2O$ calc: C 61.57; H 6.49; N 4.42; S 7.59. obs.: C 61.50; H 6.53; N 4.49; S 7.70. |
| 47 | 45 | 180 (dec) | 1.66–1.72(m, 1H), 2.08–2.22(m, 2H), 2.32–2.45(m, 2H), 2.46(d, J=16Hz, 1H), 2.74(d, J=16Hz, 1H), 2.79–3.10(m, 8H), 3.25(d, J=19Hz, 1H), 3.32–3.43(m, 1H), 3.65(s, 3H), 4.06–4.13(m, 1H), 4.26–4.33(m, 1H), 5.53(s, 1H), 6.68(d, J=7.8Hz, 1H), 6.73(d, J=8.4Hz, 1H), 6.82–6.90(m, 2H), 7.16(d, J=7.2Hz, 1H), 7.19–7.24(m, 1H), 7.26–7.35(m, 4H). | 3410, 3246, 2934, 1636, 1508, 1454, 973, 748. | 519 ((M + H)⁺) FAB free | $C_{34}H_{34}N_2O_3 \cdot 1.60H_3PO_4 \cdot 1.25H_2O$ calc: C 58.51; H 5.96; N 4.01; P 7.10 obs: C 58.34; H 5.86; N 4.01; P 7.10. |

TABLE 2-continued

Physical Properties of Example Compounds

| Comp. | % y | mp(°C.) | NMR (δ, ppm) | IR(cm$^{-1}$) | MS | Elemental anal. |
|---|---|---|---|---|---|---|
| 48 | 78 | 185 (dec) | 1.94(m, 1H), 2.08–2.23(m, 2H), 2.41(d, J=16Hz, 1H), 2.66–2.73(m, 1H), 2.73(d, J=16Hz, 1H), 2.57–2.96(m, 3H), 3.15–3.20(m, 2H), 3.35(dd, J=4.3, 13Hz, 1H), 3.70(s, 3H), 3.76(d, J=19Hz, 1H), 4.08–4.14(m, 1H), 4.27–4.33(m, 1H), 4.45(d, J=13Hz, 1H), 4.56(d, J=13Hz, 1H), 5.96(s, 1H), 6.78(d, J=8.2Hz, 1H), 6.53(d, J=8.2Hz, 1H), 6.81–6.87(m, 2H), 7.08(m, 1H), 7.50–7.58(m, 3H), 7.66(d, 6.7Hz, 1H). | 3410, 2926, 1636, 1613, 1508, 1454, 1123, 1052, 748. | 505 ((M + H)$^+$) (FAB) free | C$_{31}$H$_{32}$N$_2$O$_3$.1.00HCl.0.20H$_2$O calc.: C 72.77; H 6.18; N 5.14; Cl 6.51. obs.: C 72.53; H 6.22; N 5.30; Cl 6.33. |
| 49 | 79 | 180 (dec) | 1.82(s, 3H), 1.84(s, 3H), 1.88(m, 1H), 2.06–2.26(m, 2H), 2.29(s, 3.15H), 2.40–2.56(m, 1H), 2.61(ddd, J=4.6, 14, 14Hz, 1H), 2.72–2.87(m, 1H), 2.87–3.00(m, 3H), 3.12–3.30(m, 2H), 3.53(d, J=13Hz, 1H), 3.48–3.75(m, 2H), 3.70(s, 3H), 4.04–4.18(m, 2H), 4.26–4.38(m, 1H), 5.28(m, 1H), 5.95(s, 1H), 6.25(br d, 1H), 6.74(d, J=8.3Hz, 1H), 6.81(d, J=8.4Hz, 1H), 6.85–6.93(m, 2H), 7.14(dd, J=1.9, 6.8Hz, 1H), 8.98(br d, 1.05H). | 3392, 2922, 1636, 1611, 1510, 1437, 1224, 1038, 897, 777, 748, 551. | 483 ((M + H)$^+$) (FAB) free | C$_{31}$H$_{34}$N$_2$O$_3$.1.05 CH$_3$SO$_3$H.1.00H$_2$O calc.: C 63.99; H 6.74; N 4.66; S 5.60. obs.: C 64.19; H 6.53; N 4.54; S 5.64. |
| 50 | 71 | 185–193 | 1.83(m, 1H), 2.05–2.25(m, 2H), 2.46–2.57(m, 2H), 2.58–2.70(m, 1H), 2.72–2.86(m, 1H), 2.86–3.30(m, 3H), 3.20–3.35(m, 2H), 3.61(d, J=20Hz, 1H), 3.70(s, 3H), 3.80–3.93(m, 1H), 3.93–4.05(m, 1H), 4.05–4.24(m, 2H), 4.25–4.37(m, 1H), 5.97(s, 1H), 6.31–6.43(m, 1H), 6.34(br s, 1H), 6.76(d, J=8.3Hz, 1H), 6.79–6.90(m, 3H), 6.82(d, J=8.3Hz, 1H), 7.11(dd, J=2.6, 6.3Hz, 1H), 7.32–7.47(m, 3H), 7.57(d, J=7.4Hz, 2H), 9.35(br s, 1H). | 3406, 2930, 1636, 1613, 1508, 1452, 1371, 1284, 1261, 1050, 748.0. | 531 ((M + H)$^+$) FAB free | C$_{35}$H$_{34}$N$_2$O$_3$.1.00HCl.0.28H$_2$O calc.: C 73.47; H 6.26; N 4.90; Cl 6.20. obs.: C 73.31; H 6.33; N 4.83; Cl 6.09. |
| 51 | 54 | 205–210 | 0.96(t, d=7.3Hz, 3H), 1.36(m, 1H), 1.51–1.61(m, 1H), 1.68–1.78(m, 1H), 1.81–1.87(m, 1H), 2.18–2.24(m, 2H), 2.47–2.55(m, 1H), 2.58–2.66(m, 1H), 2.69–2.78(m, 1H), 2.89–2.99(m, 3H), 2.99–3.08(m, 1H), 3.11–3.17(m, 1H), 3.24–3.41(m, 2H), 3.45(d, J=20Hz, 1H), 3.70(s, 3H), 3.84–3.90(m, 1H), 4.08–4.15(m, 1H), 4.28–4.36(m, 1H), 6.73(d, J=8.4Hz, 1H), 6.80(d, 1–8.1Hz, 1H), 6.85–6.92(m, 2H), 7.15(d, J=7.3Hz, 1H), 8.96(br s, 1H). | 3384, 2936, 1636, 1508, 1454, 1048, 899, 748. | 471 ((M + H)$^+$) FAB free | C$_{30}$H$_{34}$N$_2$O$_3$.1.00HCl.0.50H$_2$O calc.: C 69.82; H 7.03; N 5.43; Cl 6.87. obs.: C 69.93; H 7.09; N 5.43; Cl 6.77. |
| 52 | 77 | 190–195 | 1.91(m, 1H), 2.08–2.24(m, 2H), 2.30(s, 3.12H), 2.43–2.53(m, 1H), 2.53–2.63(m, 1H), 2.81(d, J=16Hz, 1H), 2.83–2.97(m, 3H), 3.18(m, 1H), 3.12–3.31(m, 3H), 3.70(s, 3H), 3.74(d, J=20Hz, 1H), 4.08–4.15(m, 1H), 4.78–4.84(m, 1H), 4.41–4.48(m, 1H), 4.76(dd, J=15, 20Hz, 1H), 5.95(s, 1H), 6.28(br s, 1H), 6.36(m, 1H), 6.77(d, J=8.3Hz, 1H), 6.79(d, J=2.9Hz, 1H), 6.82(d, J=8.3Hz, 1H), 6.84–6.90(m, 1H), 7.05–7.15(m, 1H), 7.89(d, J=1.0Hz, 1H), 9.46(br s, 1.04H). | 3412, 2938, 1636, 1508, 1479, 1205, 1050, 777, 748, 561 | 495 ((M + H)$^+$) FAB free | C$_{31}$H$_{30}$N$_2$O$_4$.1.04 CH$_3$SO$_3$H.0.55H$_2$O calc.: C 63.67; H 5.88; N 4.63; S 5.62. obs.: C 63.55; H 5.99; N 4.60; S 5.62. |
| 53 | 83 | 184–195 | 0.90–1.42(m, 5H), 1.57–1.91(m, 7H), 2.05–2.27(m, 2H), 2.42–2.57(m, 1H), 2.58–3.12(m, 7H), 3.22–3.39(m, 2H), 3.45(d, J=20Hz, 1H), 3.70(s, 3H), 3.83(d, J=5.7Hz, 1H), 4.05–4.18(m, 1H), 4.25–4.38(m, 1H), 5.96(s, 1H), 6.46(br s, 1H), 6.74(d, J=8.4Hz, 1H), 6.81(d, J=8.4Hz, 1H), 6.85–6.94(m, 2H), 7.16 (dd, J=2.4Hz, 6.9Hz, 1H). 8.75(br s, 1H). | 3402, 2930, 2858, 1636, 1611, 1508, 1452, 1371, 1284, 1253, 1205, 1123, 1046, 897. | 510 ((M)$^+$) EI free | C$_{33}$H$_{38}$N$_2$O$_3$.1.00HCl.0.40H$_2$O calc.: C 71.50; H 7.24; N 5.05; Cl 6.40. obs.: C 71.42; H 7.22; N 5.10; Cl 6.48. |
| 54 | 30 | 185–190 | 1.80–1.94(m, 4H), 2.06–2.30(m, 2H), 2.46–2.84(m, 3H), 2.86–3.04(m, 3H), 3.10–3.50(m, 4H), 3.58–3.76(m, 1H), 3.58–3.76(m, 3H), 3.70(s, 3H), 4.05(d, J=6.0Hz, 1H), 4.00–4.20(m, 1H), 4.25–4.40(m, 1H), 5.97(s, 1H), 6.44(br s, 1H), 6.74(d, J=8.2Hz, 1H), 6.81(d, J=8.2Hz, 1H), 6.84–6.95(m, 2H), 7.01–7.08(m, 2H), 7.13–7.20(m, 1H), 7.45(dd, J=1.6, 4.4Hz, 1H), 9.25(br s, 1H). | 3366, 2932, 1632, 1611, 1508, 1454, 1441, 1371, 1284, 1253, 1203, 1164, 1123, 1058, 748. | 525 ((M + H)$^+$) FAB free | C$_{32}$H$_{32}$N$_2$O$_3$S.1.00HCl.0.60H$_2$O calc.: C 67.20; H 6.03; N 4.90; Cl 6.20; S 5.61. obs.: C 67.04; H 6.08; N 4.88; Cl 6.24; S 5.55. |
| 55 | 81 | 260 (dec) | 1.83(m, 2H), 2.04–2.27(m, 2H), 2.34(s, 3.90H), 2.45–2.63(m, 2H), 2.70–2.82(m, 1H), 2.82–2.99(m, 6H), 3.15(dd, J=4.3, 13Hz, 1H), 3.22(dd, J=6.7, 20Hz, 1H), 3.40–3.55(m, 1H), 3.77(d, J=6.6Hz, 1H), 4.13–4.23(m, 1H), 4.24–4.34(m, 1H), 5.88(s, 1H), 6.63(m, 2H), 6.84–6.93(m, 2H), 7.19(dd, J=2.0, 6.8Hz, 1H). | 3652, 2934, 1638, 1508, 1460, 1437, 1371, 1382, 1195, 1060, 785. | 414 ((M)$^+$) EI free | C$_{26}$H$_{26}$N$_2$O$_3$.1.30 CH$_3$SO$_3$H.0.70H$_2$O calc.: C 59.40; H 5.95; N 5.07; S 7.56. obs.: C 59.29; H 5.98; N 5.21; S 7.75. |

TABLE 2-continued

Physical Properties of Example Compounds

| Comp. | % y | mp(°C.) | NMR (δ, ppm) | IR(cm⁻¹) | MS | Elemental anal. |
|---|---|---|---|---|---|---|
| 56 | 69 | 180 (dec) | 1.77–1.99(m, 5H), 2.01–2.25(m, 4H), 2.33(s, 3.75H), 2.40–2.65(m, 2H), 2.65–2.80(m, 2H), 2.87–2.97(m, 3H), 3.03–3.16(m, 2H), 3, 22(ddd, J=7.0, 20 Hz, 1H), 3.36–3.50(m, 2H), 3.60(d, J=6.7Hz, 1H), 4.13–4.22(m, 1H), 4.24–34 (m, 1H), 5.88(s, 1H), 6.58–6.60(m, 2H), 6.85–6.93(m, 2H), 7.17(dd, j=1.8, 7.0Hz, 1H). | 3448, 2940, 1638, 1508, 1460, 1435, 1371, 1328, 1193, 1060, 785, 561. | 468 ((M)⁺) EI free | $C_{30}H_{32}N_2O_3 \cdot 1.25\ CH_3SO_3H \cdot 0.40H_2O$ calc.: C 62.98; H 6.39, N 4.69; S 6.73 obs.: C 62.83; H 6.62; N 4.69; S 6.72. |
| 57 | 71 | 190 (dec) | 1.83–1.89(m, 1H), 2.11–2.25(m, 2H), 2.32(s, 3.45H), 2.63(ddd, J=4.7, 13, 13 Hz, 1H), 2.78–2.85(m, 1H), 2.85–2.98(m, 4H), 3.15(ddd, J=5.3, 12, 12Hz, 1H), 3.20–3.30(m, 3H), 3.54(d, J=19Hz, 1H), 3.61(dd(d, J=5.9, 12, 12Hz, 1H), 3.98(d, J=6.7Hz, 1H), 4.06–4.13(m, 1H), 4.16–4.22(m, 1H), 4.28–4.33 (m, 1H), 5.91(s, 1H), 6.61–6.66(m, 2H), 6.86–6.93(m, 2H), 7.18(d, J=7.3Hz, 1H). 7.30(t, J=7.2Hz, 1H), 7.32–7.41(m, 4H). | 3038, 2934, 1620, 1508, 1458, 1437, 1203, 1048. | 505 ((M + H)⁺) FAB free | $C_{32}H_{32}N_2O_3 \cdot 1.15\ CH_3SO_3H \cdot 0.70\ H_2O$ calc.: C 65.34; H 6.10; N 4.46; S 5.87. obs.: C 65.32; H 6.14; N 4.37; S 5.77. |
| 58 | 60 | 220 (dec) | 1.79(m, 1H), 2.10–2.24(m, 2H), 2.34(s, 3.45H), 2.45–2.59(m, 2H), 2.74(ddd, J=4.1, 13, 13Hz, 1H), 2.88(d, J=19Hz, 1H), 2.91–2.95(m, 2H), 3.09–3.14(m, 1H), 3.14(d, J=19Hz, 1H), 3.36(dd, J=6.6, 19Hz, 1H), 3.80(d, J=6.7Hz, 1H), 4.15–4.22(m, 1H), 4.25–4.31(m, 1H), 5.85(s, 1H), 6.62(m, 2H), 6.85–6.91 (m, 2H), 7.17(d, J=7.0Hz, 1H). | 3328, 1618, 1508, 1460, 1437, 1371, 1323, 1207, 1154, 1042, 779. | 401 ((M + H)⁺) FAB free | $C_{25}H_{24}N_2O_3 \cdot 1.15\ CH_3SO_3H \cdot 0.50\ H_2O$ calc.: C 60.40; H 5.74; N 5.39; S 7.09. obs.: C 60.47; H 5.90; N 5.29; S 6.83. |
| 59 | 27 | 200 (dec) | 1.77(m, 1H), 2.08–2.23(m, 2H), 2.36–2.70(m, 2H), 2.91(m, 3H), 3.07(d, J=4.6Hz, 1H), 3.25–3.73(m, 4H), 3.85–4.24(m, 3H), 4.28–4.34(m, 1H), 5.80 (s, 1H), 6.59(m, 2H), 6.80–6.87(m, 2H), 7.08–7.14(m, 1H), 7.34–7.58(m, 5H). | 3410, 2934, 1620, 1508, 1460, 1253, 1207, 1164, 1118, 1013, 961, 750. | 491 ((M + H)⁺) FAB free | $C_{32}H_{30}N_2O_3 \cdot 1.20\ H_3PO_4 \cdot 1.00\ H_2O$ calc.: C 61.38; H 5.73; N 4.79; P 5.94. obs.: C 61.21; H 5.77; Nn 4.63; P 5.71. |
| 60 | 78 | 165–183 | 1.83(s, 3H), 1.87(s, 3H), 1.74–1.92(m, 1H), 2.08–2.36(m, 2H), 2.32(s, 3H), 2.40–2.70(m, 2H), 2.72–3.02(m, 4H), 3.10–3.26(m, 1H), 3.47(d, J=20Hz, 1H), 3.56–3.72(m, 1H), 3.68(d, J=6.4Hz, 1H), 4.04–4.24(m, 2H), 4.24–4.36 (m, 1H), 5.20–5.30(m, 1H), 5.89(s, 1H), 6.21(s, 1H), 6.56–6.66(m, 2H), 6.82–6.94(m, 2H), 7.14(dd, J=2.0, 6.8Hz, 1H), 8.95(br s, 1H), 9.18(br s, 1H). | 3198, 1644, 1624, 1466, 1325, 1209, 1187, 1164, 1044, 915, 777, 559. | 469 ((M + H)⁺) FAB free | $C_{30}H_{32}N_2O_3 \cdot 1.00\ CH_3SO_3H \cdot 0.90H_2O$ calc.: C 64.10; H 6.56; N 4.82; S 5.59. obs.: C, 64.30; H, 6.59, N 5.16; S, 5.77. |
| 61 | 58 | 200 (dec) | 1.87(m, 1H), 2.06–2.26(m, 2H), 2.46–2.56(m, 1H), 2.56–2.70(m, 1H), 2.74–3.00(m, 4H), 3.16–3.34(m, 1H), 3.55(d, J=20Hz, 1H), 3.82–3.90(m, 1H), 3.90–4.02(m, 1H), 4.10–4.24(m, 2H), 4.24–4.34(m, 1H), 5.90(s, 1H), 6.29(br s, 1H), 6.25–6.43(m, 1H), 6.62(d, J=8.3Hz, 1H), 6.65(d, J=7.8Hz, 1H), 6.82–6.39(m, 3H), 7.07–7.15(m, 1H), 7.32–7.48(m, 3H), 7.56(d, J=7.3Hz, 2H). 9.21(br s, 1H), 9.32(br s, 1H). | 3412, 2930, 1638, 1620, 1508, 1458, 1437, 748. | 517 ((M + H)⁺) FAB free | $C_{34}H_{32}N_2O_3 \cdot 1.00\ HCl \cdot 0.70H_2O$ calc.: C 72.19; H 6.13; N 4.95; Cl 6.27. obs.: C, 64.56; H, 6.19; Cl, 12.64; S, 5.21. |
| 62 | 74 | (dec) | 0.96(t, d=7.2Hz, 3H), 1.33–1.40(m, 2H), 1.48–1.58(m, 1H), 1.68–1.76(m, 1H), 1.80–1.86(m, 1H), 2.10–2.25(m, 2H), 2.30(s, 3H), 2.54(d, J=16Hz, 1H), 2.56–2.60(m, 1H), 2.71–2.80(m, 1H), 2.88–2.96(m, 3H), 2.99–3.06(m, 1H), 3.11–3.17(m, 1H), 3.24(dd, J=6.9, 20Hz, 1H), 3.30–3.43(m, 2H), 3.81(m, 1H), 4.15–4.22(m, 1H), 4.27–4.34(m, 1H), 5.89(s, 1H), 6.23(br s, 1H), 6.61 (d, J=8.4Hz, 1H), 6.63(d, J=8.4Hz, 1H), 6.85–6.93(m, 2H), 7.16(d, J=7.2Hz, 1H), 8.90(br s, 1H), 9.20(br s, 1H). | 3500, 2936, 2876 1638, 1508, 1477, 1435, 1371, 1328, 1199, 1046, 777, 748, 561. | 457 ((M + H)⁺) FAB free | $C_{29}H_{32}N_2O_3 \cdot 1.00 CH_3SO_3H \cdot 0.50H_2O$ calc.: C 64.15; H 6.64; N 4.99; S 5.71. obs.: C 64.08; H 6.62; N 4.99; S 5.62. |
| 63 | 61 | 195 (dec) | 1.89(m, 1H), 2.09–2.24(m, 2H), 2.29(s, 3H), 2.43–2.53(m, 1H), 2.58–2.67 (m, 1H), 2.79(d, J=16Hz, 1H), 2.84–2.98(m, 3H), 3.12–3.24(m, 2H), 3.24–3.30(m, 1H), 3.69(d, J=19Hz, 1H), 4.14–4.21(m, 1H), 4.26–4.33(m, 1H), 4.39–4.51(m, 3H), 4.75(dd, J=8, 14Hz, 1H), 5.89(s, 1H), 6.24(br s, 1H), 6.60–6.66(m, 3H), 6.79(d, J=3.2Hz, 1H), 6.83–6.89(m, 2H), 7.09–7.15(m, | 3380, 2938, 1638, 1626, 1253, 1205, 1118, 1046, 750. | 481 ((M + H)⁺) (FAB) | $C_{30}H_{28}N_2O_2 \cdot 1.00\ CH_3SO_3H \cdot 0.50H_2O$ calc.: C 63.57; H 5.68; N 4.74; S 5.48. obs.: C 63.52, H 5.74; N 4.74; S |

TABLE 2-continued

Physical Properties of Example Compounds

| Comp. | % y | mp(°C.) | NMR (δ, ppm) | IR(cm$^{-1}$) | MS | Elemental anal. |
|---|---|---|---|---|---|---|
| 64 | 51 | 190 (dec) | 1H), 7.89(d, J=1.0Hz, 1H), 9.20(br s, 1H), 9.42(br s, 1H). 0.89–1.39(m, 5H), 1.61–1.88(m, 7H), 2.08–2.38(m, 2H), 2.44–2.57(m, 1H), 2.57–2.87(m, 3H), 2.87–3.12(m, 4H), 3.19–3.46(m, 3H), 3.80(d, J=6.0Hz, 1H), 4.12–4.23(m, 1H), 4.23–4.36(m, 1H), 5.89(s, 1H), 6.38(br s, 1H), 6.60 (d, J=8.1Hz, 1H), 6.65(d, J=8.1Hz, 1H), 6.84–6.94(m, 2H), 7.16(dd, J=2.1, 6.6Hz, 1H), 8.72(br s, 1H), 9.24(br s, 1H). | 3368, 2930, 2856, 2638, 1620, 1508, 1454, 1371, 1325, 1296, 1253, 1207, 1118, 911. | 496 ((M)$^+$) EI free | 5.74. C$_{31}$H$_{56}$N$_2$O$_3$·1.00 HCl·0.45H$_2$O calc.: C 71.02; H 7.06; N 5.18; Cl 6.55. obs.: C 70.82; H 7.05; N 5.27; Cl 6.81. |
| 65 | 69 | 190 (dec) | 1.80–1.91(m, 1H), 2.08–2.30(m, 2H), 2.40–3.02(m, 6H), 3.08–3.74(m, 8H), 4.00(d, J=6.9Hz, 1H), 4.12–4.25(m, 1H), 4.25–4.38(m, 1H), 5.90(s, 1H), 6.36(br s, 1H), 6.61(d, J=8.5Hz, 1H), 6.64(d, J=8.2Hz, 1H), 6.84–6.94(m, 2H), 7.01–7.08(m, 2H), 7.17(dd, J=20.Hz, 6.7Hz, 1H), 7.45(dd, J=2.2, 4.1 Hz, 1H), 9.22(br s, 1H). | 3350, 2926, 1638, 1506, 1460, 1437, 1371, 1325, 1301, 1371, 1205, 1116, 1058, 748. | 511 ((M + H)$^+$) FAB free | C$_{31}$H$_{30}$N$_2$O$_3$S 1.00 HCl 0.65 H$_2$O calc.: C 66.63; H 5.83; N 5.01; Cl 6.34; S 5.74. obs.: C 70.82; H 7.05; N 5.27; Cl 6.81. |
| 66 | 25 | 232 (dec) | 0.41–0.50(1H, m), 0.51–0.70(2H, m), 0.72–0.82(1H, m), 1.05–1.17(1H, m), 1.86(1H, d, J=11.8Hz), 2.13–2.23(2H, m), 2.32(3.6H, s), 2.39(1H, d J=16.8Hz), 2.51–2.65(1H, m), 2.70–2.82(1H, m), 2.85–2.98(3H, m), 3.11–3.21 (1H, m), 3.16(3H, s), 3.25–3.31(sH, m), 3.48–3.58(2H, m), 4.14–4.22(1H, m), 4.27–4.37(1H, m), 4.52(1H, d, J=6.3Hz), 6.03(1H, s), 6.61–6.67(2H, m), 6.87–6.93(2H, m), 7.20(1H, dd, J=6.9, 1.9Hz), 8.60(1.2H, br s), 9.24(1H, br). | 3400, 2946, 1620, 1562, 1502, 1435, 1371, 1328, 1294, 1197, 1114, 1052, 1004, 913, 866, 781, 752 | 468 ((M)$^+$) EI free | C$_{30}$H$_{32}$N$_2$O$_3$·1.20CH$_3$SO$_3$H 0.6H$_2$O calc.: C, 63.01; H, 6.44; N, 4.71; S, 6.47. obs.: C, 63.16; H, 6.66; N, 4.69; S, 6.22. |

[Example 67]

δ-Opioid Activity

Using mouse vas deferens (MVD), antagonistic compounds were examined for antagonism against a δ-opioid agonist DPDPE, and agonistic compounds were examined for inhibitory activity against MVD contraction by electric stimulation, and for antagonism by a δ-opioid antagonist NTI.

Male ddy strain mice were used in this experiment. Each of the vas deferens isolated from the mice was hung in a Magnus tube which was filled with a Krebes-Henseleit solution (NaCl 118 nM; KCl 4.7 mM; $CaCl_2$ 2.5 mM; $KH_2PO_4$ 1.1 mM; $NaHCO_3$ 25 mM; glucose 11 mM), and aerated with a gas of 5% carbon dioxide and 95% oxygen and maintained at 37° C. Electric stimulation was applied through upper and lower ring-shaped platinum electrodes at 0.1 Hz and 5.0 mS. Tissue contraction was recorded on a polygraph using an isometric transducer.

<Antagonist>

Initially, DPDPE was added in a cumulative manner to determine the $IC_{50}$ value (concentration for 50% inhibition of contraction induced by electric stimulation). Next, 100 nM of a sample compound was added to the system beforehand, and 20 minutes later, DPDPE was added in a cumulative manner. According to the above procedure, the ratio of the $IC_{50}$ value of DPDPE in the presence of the sample compound to that in the absence of it was determined, and the $pA_2$ value was calculated in accordance with the Schild, et al.'s method [Schild, H. O., Br. *J. Pharamacol. Chamother.* 4, 277 (1949)].

TABLE 2

δ-Opioid Activities of Antagonistic Compounds

| Compound | $pA_2$ |
|---|---|
| 1 | 9.2 |
| 2 | 8.7 |
| 3 | 8.6 |
| 4 | 9.4 |
| 5 | 8.3 |
| 6 | 8.5 |
| 7 | 8.3 |
| 8 | 8.3 |
| 9 | 8.5 |
| 10 | 8.8 |
| 11 | 8.2 |
| 19 | 9.0 |
| 20 | 8.4 |
| 21 | 8.0 |
| 22 | 9.1 |
| 23 | 9.8 |
| 24 | 8.0 |
| 26 | 8.5 |
| 27 | 7.9 |
| 30 | 7.9 |
| 66 | 9.5 |

<Agonist>

Initially, a sample compound was added in a cumulative manner to determine the $IC_{50}$ value (concentration for 50% inhibition of contraction induced by electric stimulation). Next, 10 NTI was added to the system beforehand, and 20 minutes later, the sample compound was added in a cumulative manner. According to the above procedure, the ratio of the $IC_{50}$ values of the sample compound in the presence of NTI to that in the absence of NTI was determined, and the Ke value was calculated in accordance with the following equation.

$$Ke = [\text{NTI Concentration}]/[(IC_{50} \text{ ratio}) - 1]$$

TABLE 3

δ-Opioid Activities of Agonistic Compounds

| Compound | $IC_{50}$ | Ke |
|---|---|---|
| 28 | 15.8 | 0.05 |
| 55 | 18.2 | 0.21 |
| 56 | 2.96 | 6.21 |
| 57 | 9.71 | 0.06 |
| 65 | 33.9 | 0.03 |

[Example 68]

Evaluation of Antitussive Action in Rat as a Model for Capsaicin-Induced Cough

<Inducement of Cough>

Cough was induced by forcing rats to inhale capsaicin (60 μM) which was nebulized by an ultrasonic nebulizer, and fed to caps over the rats' heads through silicone tubes by a respirator. Capsaicin was fed for inhalation at a rate of 70 times/min. and 10 ml each time.

<Experimental Schedule>

Two hundred and seventy minutes before the drug administration, capsaicin was inhaled for 5 minutes, and inducement of coughing was confirmed during this period. Thirty minutes after the drug administration, capsaicin was inhaled for 5 minutes, and the number of induced coughs during capsaicin inhalation was counted. Antitussive effect was evaluated by determining an inhibitory ratio, namely, the ratio of the number of coughs after the drug administration to that before the drug administration. Capsaicin was dissolved in saline. Each drug was dissolved in a 10% DMSO solution and intraperitoneally administered. The effect of the drug is expressed with an $ED_{50}$ value which is the dosage for 50% cough inhibition

TABLE 4

Antitussive Activities of Compounds

| Compound | $ED_{50}$ (μg/kg) |
|---|---|
| 1 | 9.14 |
| 2 | 1.71 |
| 3 | 4.37 |
| 4 | 8.58 |
| 5 | 20.79 |
| 6 | 9.43 |
| 7 | 16.3 |
| 9 | 12.25 |
| 10 | 15.70 |
| 11 | 3.43 |
| 12 | 2.50 |
| 13 | 5.33 |
| 14 | 23.8 |
| 15 | 9.68 |
| 16 | 4.73 |
| 17 | 5.02 |
| 18 | 13.4 |
| 34 | 1.10 |
| 35 | 21.2 |
| 40 | 2.46 |
| 42 | 21.05 |
| 44 | 10.9 |

[Example 69]

Evaluation of Analgesic Action by Acetic Acid Writhing Test in Mouse

Five-week-old ddY strain mice were subjected to this experiment. A 0.6% acetic acid solution was intraperitoneally administered at a volume of 0.1 ml/10 g·.body weight.

Analgesic activity was evaluated with an index which was the number of writhing reactions occurring over 10 minutes from 10 minutes after administration. The drug to be evaluated was dorsal-subcutaneously administered 15 minutes before the administration of acetic acid.

In this experiment, the compound 28 exhibited a strong analgesic activity with a $ED_{50}$ value of 16.7 mg/kg.

Industrial Applicability

The compounds of the present invention have been found to act on δ-opioid receptors to exhibit strong antitussive and analgesic actions. Accordingly, the compounds of the present invention have been found to be favorable in the pharmaceutical field as effective antitussives and analgesics.

We claim:

1. An indole derivative represented by the following general formula (I) or a pharmacologically acceptable acid addition salt thereof:

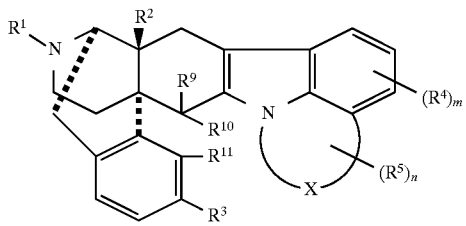

wherein:
- $R^1$ is hydrogen, an alkyl having 1 to 5 carbon atoms, a cycloalkylalkyl having 4 to 7 carbon atoms, a cycloalkenylalkyl having 5 to 7 carbon atoms, an aryl having 6 to 12 carbon atoms, an aralkyl having 7 to 13 carbon atoms, an alkenyl having 3 to 7 carbon atoms, a furan-2-yl-alkyl in which the alkyl has 1 to 5 carbon atoms, or a thiophene-2-yl-alkyl in which the alkyl has 1 to 5 carbon atoms;
- $R^2$ is hydrogen, hydroxy, an alkoxy having 1 to 5 carbon atoms, or an alkanoyloxy having 1 to 5 carbon atoms;
- $R^3$ is hydrogen, hydroxy, an alkoxy having 1 to 5 carbon atoms, an alkanoyloxy having 1 to 5 carbon atoms, or an aralkyloxy having 7 to 13 carbon atoms;
- —X— is a crosslinkage comprising 2 to 5 carbon atoms in which at least one of the carbon atoms may be replaced with a nitrogen atom, an oxygen atom, or a sulfur atom;
- m is an integer from 0 to 3;
- n is an integer from 0 to 10;
- each of m $R^4$ groups and n $R^5$ groups is individually fluoro, chloro, bromo, iodo, nitro, an alkyl having 1 to 5 carbon atoms, an alkoxy having 1 to 5 carbon atoms, trifluoromethyl, trifluoromethoxy, cyano, phenyl, a hydroxyalkyl having 1 to 3 carbon atoms, isothiocyanato, $SR^6$, $SOR^6$, $SO_2R^6$, $(CH_2)_pOR^6$, $(CH_2)_pCO_2R^6$, $SO_2NR^7R^8$, $CONR^7R^8$, $(CH_2)_pNR^7R^8$, or $(CH_2)_pN(R^7)COR^8$, in which p is an integer from 0 to 5; $R^6$ is an alkyl having 1 to 5 carbon atoms; each of $R^7$ and $R^8$ is individually hydrogen, an alkyl having 1 to 5 carbon atoms, or a cycloalkylalkyl having 4 to 7 carbon atoms; and among the above m $R^4$ groups and n $R^5$ groups, at least one pair of adjacent $R^4$ groups, adjacent $R^5$ groups, and one $R^4$ and one $R^5$ groups may be linked to form a benzene, pyridine, cyclopentane, cyclohexane, or cycloheptane condensed ring;
- $R^9$ is hydrogen, alkyl having 1 to 5 carbon atoms, an alkenyl having 1 to 5 carbon atoms, an aralkyl having 7 to 13 carbon atoms, a hydroxyalkyl having 1 to 3 carbon atoms, $(CH_2)_pOR^6$, or $(CH_2)_pCO_2R^6$, in which definitions of p and $R^6$ are the same as above;
- $R^{10}$ and $R^{11}$ are linked to form an —O—, —S—, or —CH$_2$— group; or $R^{10}$ is hydrogen while $R^{11}$ is independently hydrogen, hydroxy, an alkoxy having 1 to 5 carbon atoms, or an alkanoyloxy having 1 to 5 carbon atoms; and the compound expressed by the general formula (I) may be a (+) form, a (−) form, or a (±) form.

2. The indole derivative or the pharmacologically acceptable acid addition salt thereof according to claim 1, wherein said $R^{10}$ and $R^{11}$ are linked to form an —O— group.

3. The indole derivative or the pharmacologically acceptable acid addition salt thereof according to claim 1, wherein each of said $R^4$ and $R^5$ is individually fluoro, chloro, bromo, iodo, nitro, an alkyl having 1 to 5 carbon atoms, an alkoxy having 1 to 5 carbon atoms, trifluoromethyl, trifluoromethoxy, cyano, phenyl, a hydroxyalkyl having 1 to 3 carbon atoms, isothiocyanato, $SR^6$, $SOR^6$, $SO_2R^6$, $(CH_2)_pCO_2R^6$, $SO_2NR^7R^8$, $CONR^7R^8$, or $(CH_2)_pNR^7R^8$, in which p is an integer from 0 to 5; $R^6$ is an alkyl having 1 to 5 carbon atoms; each of $R^7$ and $R^8$ is individually hydrogen, an alkyl having 1 to 5 carbon atoms, or a cycloalkylalkyl having 4 to 7 carbon atoms.

4. The indole derivative or the pharmacologically acceptable acid addition salt thereof according to claim 1, wherein at least one pair of adjacent $R^4$ groups, adjacent $R^5$ groups, and one $R^4$ and one $R^5$ groups are linked to form a benzene, pyridine, cyclopentane, cyclohexane, or cycloheptane condensed ring.

5. The indole derivative or the pharmacologically acceptable acid addition salt thereof according to claim 4, wherein at least one pair of adjacent $R^4$ groups, adjacent $R^5$ groups, and one $R^4$ and one $R^5$ group are linked to form a benzene, cyclopentane, cyclohexane, or cycloheptane condensed ring.

6. The indole derivative or the pharmacologically acceptable acid addition salt thereof according to claim 4, wherein at least one pair of adjacent $R^4$ groups, adjacent $R^5$ groups, and one $R^4$ and one $R^5$ groups are linked to form a pyridine condensed ring.

7. A medicine comprising the indole derivative or the pharmacologically acceptable acid addition salt thereof according to claim 1.

8. A medical composition comprising an effective amount of the indole derivative or the pharmacologically acceptable acid addition salt thereof according to claim 1 contained in a pharmacologically acceptable carrier.

9. An antitussive comprising the indole derivative or the pharmacologically acceptable acid addition salt thereof according to claim 1.

10. An analgesic comprising the indole derivative or the pharmacologically acceptable acid addition salt thereof according to claim 1.

11. A method for suppressing coughing, comprising administering the indole derivative or the pharmacologically acceptable acid addition salt thereof according to claim 1.

12. A method for removing pain, comprising administering the indole derivative or the pharmacologically acceptable acid addition salt thereof according to claim 1.

13. A process for producing an indole derivative represented by the general formula (I) or the pharmacologically acceptable acid addition salt thereof, comprising reacting a morphinan derivative represented by the following general formula (II):

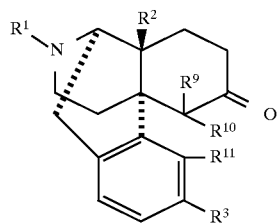 (II)
with a hydrazine derivative represented by the following formula (III):
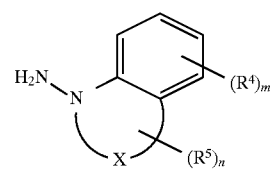 (III)
wherein the definitions of $R^1$, $R^2$, $R^3$, $R^9$, $R^{10}$ and $R^{11}$ in the general formula (II), and the definitions of —X—, m, n, $R^4$ and $R^5$ in the general formula (III) are the same as those in claim 1.
* * * * *

UNITED STATES PATENT AND TRADEMARK OFFICE
CERTIFICATE OF CORRECTION

PATENT NO. : 5,849,731
DATED : 12/15/98
INVENTOR(S) : Nagase et al.

It is certified that error appears in the above-identified patent and that said Letters Patent is hereby corrected as shown below:

Column 1, line 15, change "Nowadays, opioid" to --Opioid--.

Column 1, line 26, delete "surely"

Column 1, line 32, after "and" insert --which--.

Column 1, line 56, change "the" (first occurrence) to --an--.

Column 1, line 63, change "The Inventors" to --Accordingly, the Inventors Have--.

Signed and Sealed this

Twentieth Day of April, 1999

Attest:

Q. TODD DICKINSON

*Attesting Officer*  Acting Commissioner of Patents and Trademarks